United States Patent [19]

Freese, V et al.

[11] Patent Number: 5,604,441

[45] Date of Patent: Feb. 18, 1997

[54] IN-SITU OIL ANALYZER AND METHODS OF USING SAME, PARTICULARLY FOR CONTINUOUS ON-BOARD ANALYSIS OF DIESEL ENGINE LUBRICATION SYSTEMS

[75] Inventors: Charles E. Freese, V, Westland, Mich.; Michael J. Rostoskey, Knoxville; Raymond E. Garvey, III, Powell, both of Tenn.

[73] Assignee: Detroit Diesel Corporation, Detroit, Mich.

[21] Appl. No.: 403,638

[22] Filed: Mar. 14, 1995

[51] Int. Cl.$^6$ .................................................. G01R 27/26
[52] U.S. Cl. ........................................... 324/663; 324/667
[58] Field of Search ................................. 324/600, 676, 324/649, 658, 659, 660, 662, 663, 664, 667, 671, 672, 686, 690, 553, 204, 232, 678, 227, 228, 361; 73/53.05

[56] References Cited

U.S. PATENT DOCUMENTS

| | | | |
|---|---|---|---|
| 1,940,772 | 12/1933 | Schoenberg | 88/14 |
| 2,599,583 | 6/1952 | Robinson et al. | 175/183 |
| 2,889,736 | 6/1959 | Borg | 88/14 |
| 3,049,964 | 8/1962 | Miller et al. | 88/14 |
| 3,371,574 | 3/1968 | Dwyer | 88/14 |
| 3,526,127 | 9/1970 | Sarkis | 73/64 |
| 3,790,279 | 2/1974 | Skala | 356/70 |
| 3,829,217 | 8/1974 | Johnson et al. | 356/70 |
| 3,892,485 | 7/1975 | Merritt et al. | 356/103 |
| 3,981,584 | 9/1976 | Guymer | 356/70 |
| 4,003,661 | 1/1977 | Yamano | 356/201 |
| 4,029,554 | 6/1977 | Ellison | 204/1 T |
| 4,100,491 | 7/1978 | Newman, Jr. | 324/204 |
| 4,205,904 | 6/1980 | Skubich et al. | 340/631 |
| 4,219,805 | 8/1980 | Magee et al. | 340/631 |
| 4,302,754 | 11/1981 | Magee et al. | 340/631 |
| 4,323,843 | 4/1982 | Batham | 324/204 |
| 4,392,110 | 7/1983 | El-Menshawy | 324/453 |
| 4,443,754 | 4/1984 | King | 324/662 |
| 4,448,887 | 5/1984 | Kauffman et al. | 436/60 |
| 4,467,637 | 8/1984 | Rumberger | 73/61 R |
| 4,492,461 | 1/1985 | Jones et al. | 356/38 |
| 4,492,921 | 1/1985 | Sandulyak et al. | 324/204 |
| 4,497,200 | 2/1985 | Tournier | 73/64 |
| 4,500,839 | 2/1985 | Jones et al. | 324/204 |
| 4,561,777 | 12/1985 | Radziemski et al. | 356/318 |
| 4,563,644 | 1/1986 | Lenander et al. | 324/232 |
| 4,570,069 | 2/1986 | Gager | 250/343 |

(List continued on next page.)

OTHER PUBLICATIONS

The Hansen Report On Automotive Electronics, vol. 6, No. 6; Jul./Aug. 1993; pp. 2, 7–8; "Oil–Degradation Monitors—GM Could Be First".

Schwartz, S. E. and Smolenski, D. J.; "Development of an Automatic Engine Oil–Change Indicator System", Feb. 23, 1987; SAE Technical Paper #870403.

Saloka, G. S. and Meitzler, A. H.; "A Capacitive Oil Deterioraton Sensor", Feb. 25,–Mar. 1, 1991; SAE Technical Paper #910497.

Morishita, S., Suzuki, K., Ashida, T., Tasaka, K., and Nakada, M.; "Development of an On–Board Type Oil Deterioration Sensor", Oct. 21, 1993; SAE Technical Paper #932840.

*Primary Examiner*—Louis M. Arana
*Attorney, Agent, or Firm*—Brooks & Kushman P.C.

[57] ABSTRACT

A method and apparatus for detecting the degree of deterioration of a lubricating oil for an operating machine includes a grid-like capacitive sensor that uses the lubricating oil as a dielectric medium. A magnetic field is imposed upon the oil to attract ferromagnetic wear particles into the vicinity of the sensor. Preferably, the magnetic field is generated by at least two independently controlled electromagnet windings aligned such that the magnetic field produced by each winding acts upon the wear particles. A plurality of capacitance measurements are taken at periodic intervals at each of several magnet operational states for respective classification and analysis. All windings may be simultaneously de-energized for release of captured particles back in to an oil circulation stream and to clean the capacitative sensor grid of accumulated particulates.

32 Claims, 31 Drawing Sheets

U.S. PATENT DOCUMENTS

| | | | |
|---|---|---|---|
| 4,646,070 | 2/1987 | Yasuhara et al. | 340/603 |
| 4,675,596 | 6/1987 | Smith | 324/61 QS |
| 4,675,662 | 6/1987 | Kondo et al. | 340/631 |
| 4,677,425 | 6/1987 | Singleton et al. | 340/627 |
| 4,677,847 | 7/1987 | Sawatari et al. | 73/64 |
| 4,686,469 | 8/1987 | Lewis | 324/204 |
| 4,692,698 | 8/1987 | Lewis | 324/204 |
| 4,699,509 | 10/1987 | Kamiya et al. | 356/70 |
| 4,701,713 | 10/1987 | Eaton et al. | 324/442 |
| 4,731,578 | 3/1988 | Tsaprazis | 324/204 |
| 4,741,204 | 5/1988 | Luck et al. | 73/116 |
| 4,742,476 | 5/1988 | Schwartz et al. | 364/550 |
| 4,766,373 | 8/1988 | Chambers et al. | 324/204 |
| 4,773,556 | 3/1988 | Meitzler et al. | 73/64 |
| 4,785,287 | 11/1988 | Honma et al. | 340/631 |
| 4,791,374 | 12/1988 | Yodice et al. | 324/439 |
| 4,796,204 | 1/1989 | Inone | 364/550 |
| 4,823,625 | 4/1989 | Hamilton | 73/866.5 |
| 4,831,362 | 5/1989 | Tsaprazis | 340/515 |
| 4,839,831 | 6/1989 | Imajo | 364/550 |
| 4,841,244 | 6/1989 | Chambers | 324/204 |
| 4,847,768 | 7/1989 | Schwartz et al. | 364/424.03 |
| 4,857,829 | 8/1989 | Sagae et al. | 324/61 R |
| 4,878,019 | 10/1989 | Tsaprazis et al. | 324/204 |
| 5,001,424 | 3/1991 | Kellett et al. | 324/204 |
| 5,027,065 | 6/1991 | Bares et al. | 324/204 |
| 5,049,742 | 9/1991 | Hosonuma et al. | 250/301 |
| 5,060,156 | 10/1991 | Vajgart et al. | 364/424.03 |
| 5,076,397 | 12/1991 | Yamada | 184/108 |
| 5,132,225 | 7/1992 | Dickakian | 436/60 |
| 5,157,963 | 10/1992 | Muyskens et al. | 73/53.05 |
| 5,177,445 | 1/1993 | Cross | 324/637 |
| 5,179,346 | 1/1993 | McGee et al. | 324/693 |
| 5,262,732 | 11/1993 | Dickert et al. | 324/672 |

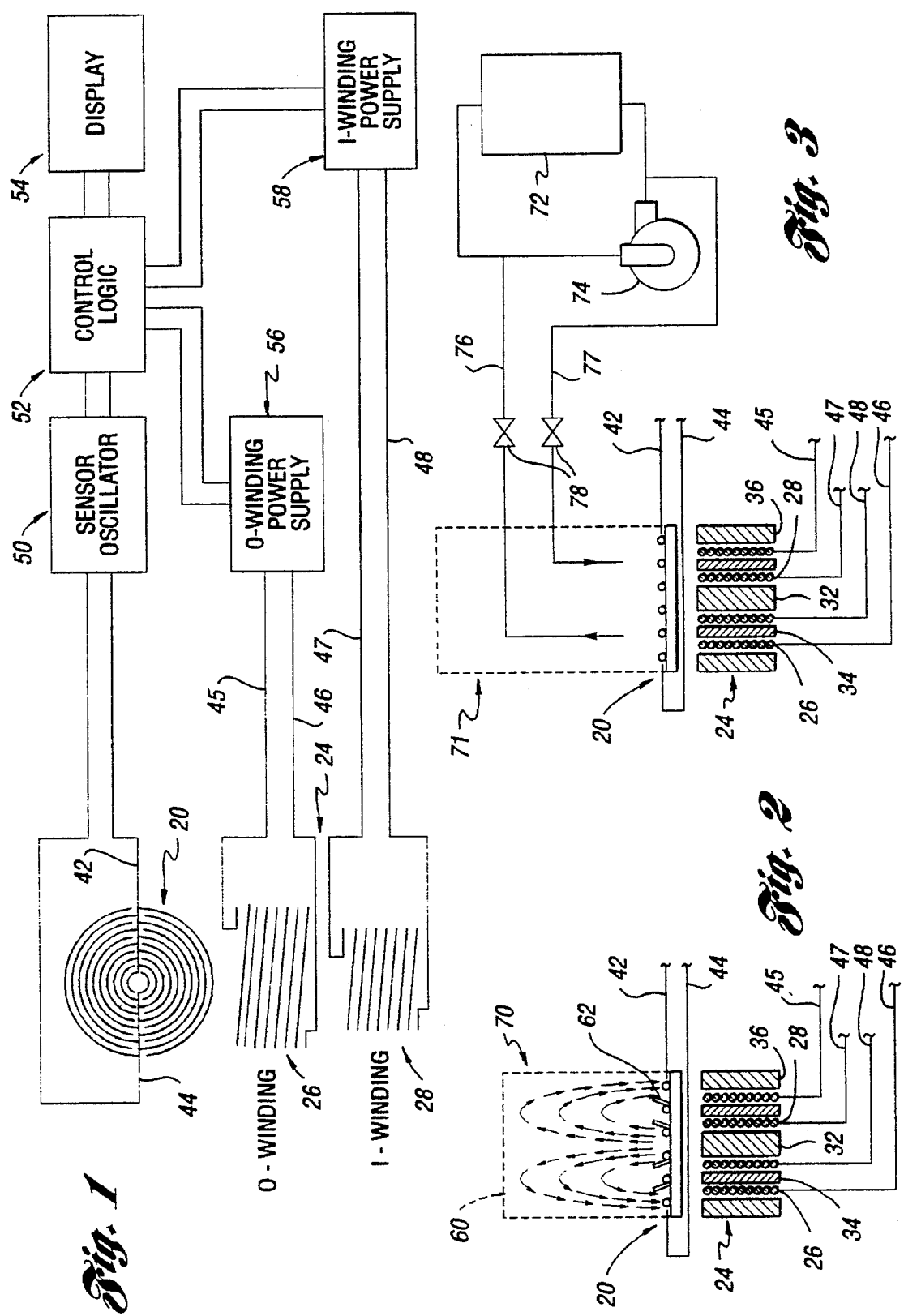

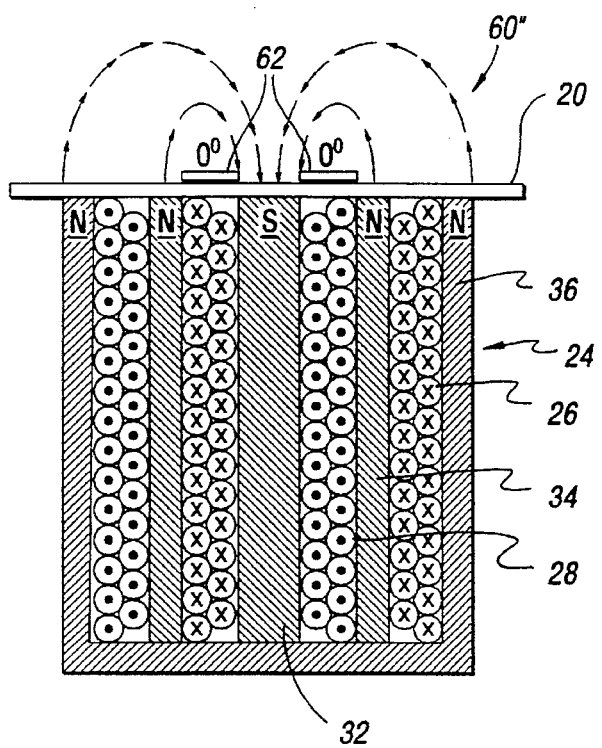
Fig. 10
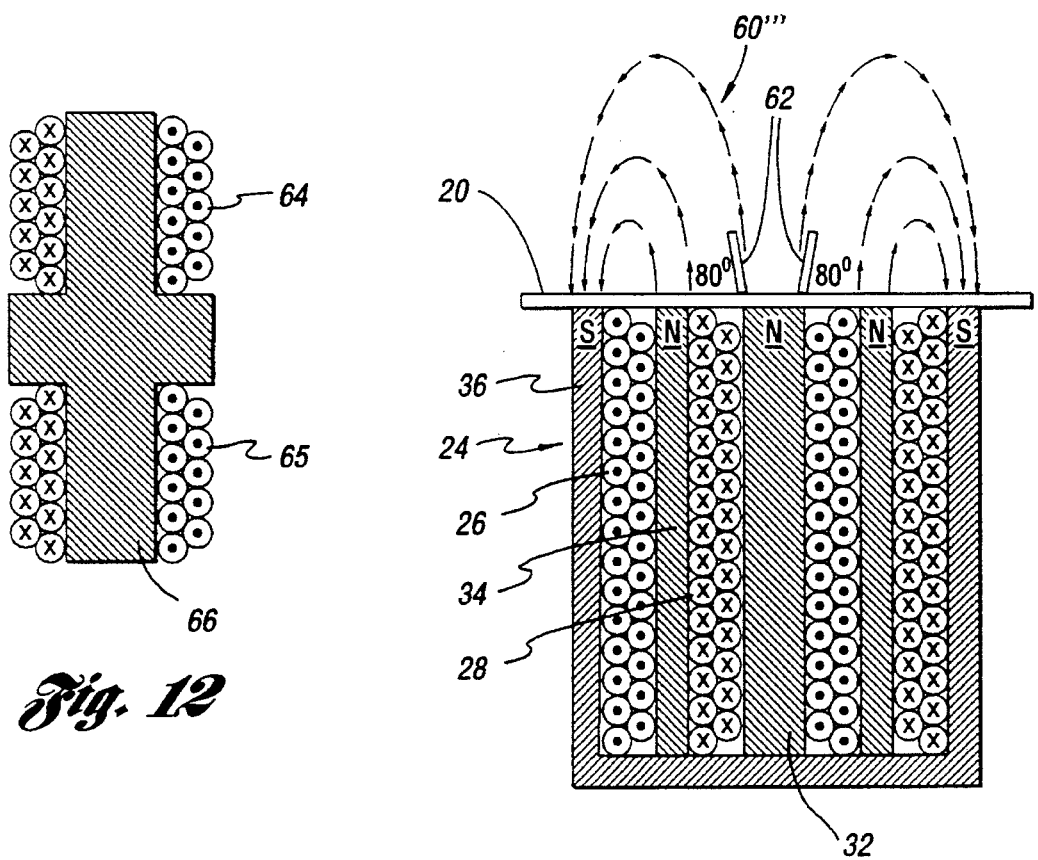
Fig. 12
Fig. 11

IN-SITU OIL ANALYZER AND METHODS OF USING SAME, PARTICULARLY FOR CONTINUOUS ON-BOARD ANALYSIS OF DIESEL ENGINE LUBRICATION SYSTEMS

TECHNICAL FIELD

This invention relates to apparatus and methods for detecting the degree of deterioration of lubricating oil and, more particularly, to such (i) apparatus and methods for detecting deterioration due to presence of the following: corrosive products caused by such conditions as oxidation, nitration, and the formation of acids; contaminants such as soot, water and glycol coolants; and ferromagnetic and non-ferrous metallic particles caused by system wear; and (ii) use of the foregoing as an in-situ oil analyzer for heavy-duty diesel engines.

BACKGROUND ART

The presence of corrosive products, contaminants and/or ferromagnetic particles, or non-ferrous metallic particles in a lubricating oil are threatening symptoms from the system in which the oil is used because of damage that has, or will occur to the system if deteriorating components are not replaced or repaired, or the oil is not promptly changed.

Many methods and devices have been developed to detect the contamination or breakdown, of oil. One such device, shown in U.S. Pat. No. 4,646,070 issued to Yasuhara, discloses a device for detecting deterioration in lubricating oil which comprises a pair of capacitor electrodes coated with insulating material and positioned in the lubricating oil. The device uses the oil as a dielectric between the sensors to develop a periodic voltage signal across the sensor capacitor, thus determining changes in the dielectric constant indicative of deterioration of the oil. A major weakness of this device and other similar devices is that they do not indicate the type or magnitude of deterioration (e.g., contamination or wear) in the system.

U.S. Pat. No. 5,262,732 issued to A. D. Dickert et al teaches a method and apparatus for simultaneously testing for, and identifying corrosive products, contamination, and ferromagnetic particles as well as non-ferrous wear particles in lubricating oil. Since the apparatus detects the type of products present in oil, a user is able to make a more knowledgeable determination of the conditions causing the deterioration of the oil. The Dickert et al instrument uses a permanent magnet in combination with an electromagnet to attract, orient, and hold ferrous particles against a capacitative surface. Because the Dickert et al instrument does not consume the test sample during the test sequence, multiple tests of the same oil sample may be conducted.

Use of this type of apparatus as might be applied to on-board, continual, real-time analysis of vehicle engine oil, particularly in heavy-duty diesel engines, is considered by the inventors of the present invention to be especially useful in light of the following additional background.

As is known, prolonged operation of a machine, such as an engine, with degraded lubricant can significantly decrease the longevity of the machine. Typically, engine manufacturers recommend engine oil change intervals in terms of either a predetermined calendar period, engine running hours, or distance travelled by a vehicle powered by the engine. These service intervals are usually based upon historical experience gleaned from similar applications. Laboratory oil analysis helps to improve oil drain recommendations, but is costly and the results are often received too late to allow effective corrective action. Thus, the practice of changing oil based on a predetermined recommended schedule may result in replacing oil which has not yet detrimentally degraded. Conversely, in some situations, this practice results in operating the engine with severely degraded lubricating oil. The practice is still often followed, however, due at least in part to the difficulty in establishing criteria for accurately evaluating the quality or condition of the oil. Although satisfactory for some applications, a predetermined oil change schedule is not acceptable for many vehicles because of the wide variations in operating conditions. For example, a predetermined schedule can not anticipate sporadic harsh operating conditions, such as excessive engine idling periods in cold ambient conditions using high sulfur fuel.

Further, extreme operating temperatures, load conditions, contaminants and mechanical failures, alone or in combination, accelerate oil degradation. Such degradation is often manifested as a change in oil color, a change in viscosity, and/or an increase in the presence of soot agglomeration, and water and wear particles, to name a few. Oil quality analysis is discussed in greater detail in *Development of an Automatic Engine Oil-Change Indicator System* by Shirley E. Swartz and Donaly J. Smolenski, published by the Society of Automotive Engineers, 1987, incorporated herein by reference. Swartz and Smolenski suggest an empirical mathematical model approach based upon current measured engine operating parameters such as engine hours, ambient temperatures, engine oil temperature, and the like, rather than detecting the condition of the oil directly.

A fresh, petroleum-based lubricating oil is primarily composed of hydrocarbon molecules with no net electrical charge which are weakly polar or have a non-polar charge distribution. Fresh mineral oils can be characterized as having a very high electrical resistance and a relatively low dielectric constant (permittivity). These electrical properties change as the oil degrades and becomes contaminated. Specifically, increases in insoluble content, the presence of moisture and acids, or the presence of conductive metallic and non-metallic debris may increase the dielectric constant of an oil, reduce its resistance, or both.

A combined measure of permittivity and resistivity can be made by measuring the AC impedance or effective capacitance (rate of charge divided by the applied potential) across two plates separated by a quantity of oil. An approximate model for the system is an ideal capacitor influenced primarily by permittivity, with a parallel resistance influenced primarily by ionic conduction. Charge mobility not involving conductive particles in a dielectric fluid involves mechanical motion of charged or dipole particles within the fluid. Therefore, system impedance is related to the parameters which describe the hydrodynamics of particles moving in a fluid. These parameters include the oil viscosity, the applied electric and magnetic forces, particle size, and particle shape.

SUMMARY OF THE INVENTION

As an operating principle, the present invention in one context includes measuring the time-rate-of-change of effective capacitance in the presence of time-varying magnetic and electric fields over a standard test period, for example 500 seconds. In a stagnant oil sample, these applied fields act along with gravity to attract ferromagnetic particles, polar insolubles, and conductive metal particles to a variable capacitance sensing element. Consequently, the time-rate-of-change values can be related specifically to the amount and species of contaminants which are extracted from the oil, as well as the general, bulk oil properties. When the oil sample is flowing over the sensing element, the electromagnets of the present invention can be turned on to collect ferrous particles, turned off to release them, or switched to control their angular orientation on the sensing element.

The present invention uniquely discriminates between ferromagnetic and other debris by comparing the time-rate-of-change of effective capacitance of multiple magnet states. In addition, the sensor also determines the absolute effective capacitance at the beginning of the test which may be used as a reference to compare the test oil to a sample of the fresh bulk oil when the results of the fresh oil calibration test have been stored. The comparison provides a non-specific indication of changes in the bulk oil chemistry. In the absence of a calibration sample, this value should still be monitored over time to detect sudden changes in bulk oil chemistry which typically accompany additive depletion (e.g. adding new oil to the sump) or gross contamination (i.e. due to a mechanical component failure).

The present invention includes an apparatus for monitoring the condition of lubricating oil circulating in an operating machine for the possible presence of corrosive products, contamination such as water infiltration, and ferromagnetic and non-ferrous metallic particles in the oil. To this extent, the present invention includes a chamber for presenting a controlled oil sample volume to a sensor capable of identifying certain contaminants within the sample. An electromagnetic device is provided to attract and/or orient magnetically responsive contaminant particles from suspension within the oil sample volume to a sensing surface of the sensor.

In a preferred embodiment of the invention, at least two electromagnets are arranged with coaxially effective flux fields. Power for the electromagnets is microprocessor controlled for selectively changing the power and/or polarity of each electromagnet. Normally, no permanent magnet or residual magnetic field is provided or established in the sample chamber. Consequently, when power to all electromagnets is terminated, normal oil circulation throughout the sample chamber and over the sensing surface tends to flush away all accumulated debris from the sensing surface in preparation for a subsequent test sequence.

Operationally, the electromagnets impose corresponding magnetic fields upon the lubricating oil in sequentially variable field flux patterns so as to attract any ferromagnetic particles within the oil to the sensing surface. Furthermore, in a preferred embodiment, the magnetic fields of the electromagnet are cyclically switched so as to vibrate and reorient the ferromagnetic particles by changing the electromagnetic flux orientation without repelling the particles from the sensor.

The sensor preferably includes a sensor element, a means for monitoring the output of the sensor element, and a means for processing the sensor output. The apparatus is assembled in a manner which allows circulating oil to be exposed to the sensor element which includes at least two conductors immersed in the oil which serves as an insulating dielectric medium. Thus, the sensor element acts as a capacitor with capacitance varying in relation to at least the area of the conductors, the distance between the conductors, and the dielectric constant and other properties of the oil. This relationship between the sensor element and the lubricating oil allows determination of various properties of the oil which is subjected to the magnetic field while the machine associated with the lubricating oil circulation system is operating.

In a preferred embodiment, control logic implemented by a programmed microprocessor determines the amount and type of deterioration of the oil by comparing changes in the sensor capacitance over a measured time interval. A higher capacitance in circulating machine oil (relative to the calibration oil) that remains relatively constant over time indicates the presence of corrosive products. A steady increase of the sensor capacitance over time while exposed to the circulating machine oil indicates the presence of contamination or lubrication deterioration. A change of the sensor capacitance which corresponds to the magnetic state of the sensor while the sensor is exposed to the circulating oil indicates the presence of ferromagnetic particles in the oil. The changing polarities of the electromagnets causes reorientation of the ferromagnetic particles resulting in a fluctuation in the sensor capacitance.

The invention takes advantage of the characteristic differences between various types of lubricating oil and characteristic contaminants. Mineral oil, for example, has a lower density than most contaminants, including water. As a result, gravity is likely to draw contaminants to the sensor grid during periods without flow. Also, most contaminants possess electrical characteristics that vary widely from those of oil. In addition, many solid contaminants which cause accelerated wear of engine components exhibit a magnetic response. Oils, however, normally do not have a magnetic response. Such differences make it possible for the present invention to discriminate between oil and virtually every likely contaminant.

It is, therefore, an object of the present invention to provide an improved in-situ oil quality sensor and methods of using the same.

It is an additional object of the present invention to provide an in-situ oil quality sensor capable of identifying oil drain intervals utilizing conventional and unconventional parameters, and detecting engine malfunction or incipient failure.

It is a further object of the present invention to provide an on-board, in-situ oil quality sensor in an oil lubrication system, such as a heavy-duty diesel engine powered vehicle, capable of identifying optimal engine oil drain intervals based at least upon engine cycle and condition, original oil quality, and direct real-time oil property measurements.

It is a further object of the present invention to provide an on-board, in-situ oil quality sensor capable of identifying engine failure modes based at least upon fuel dilution, coolant dilution, excessive wear, and abnormally high soot loading.

It is still a further object of the present invention to provide an on-board, in-situ oil quality analyzer capable of communicating warnings and recommended actions to operators and mechanics, and logging fault codes indicating abusive operating procedures and/or conditions.

Further, it is an object of the present invention to provide a "smart sensor system" capable of learning typical oil degradation patterns for a specific engine and using these engine-specific oil drain histories to optimize subsequent oil drain intervals.

The present invention is also directed toward detecting engine malfunctions or incipient failures by analyzing the oil for the following: ferrous wear metal concentration, non-ferrous wear metal concentration, coolant contamination, excessive soot concentrations, and fuel dilution.

Further, the invention, in one form, is directed toward continuous oil level detection including high oil level, low oil level, and oil level change resulting from, for example, make-up oil additions.

Stated otherwise, it is an object of the present invention to provide a durable, low cost, on-board oil quality sensor capable of: (i) identifying optimal engine oil drain intervals on an engine-specific basis, including engine cycle, engine condition, original oil quality, and direct oil property measurements in real-time; (ii) identifying engine failure modes, including fuel dilution, coolant dilution, excessive wear, and abnormally high soot loading; (iii) communicating warnings and recommended action to operators and mechanics; and (iv) logging fault codes for abusive operating and maintenance procedures.

In carrying out the above object and other objects and features of the present invention, a method is also provided for monitoring the quality of a heavy-duty diesel engine lubricant. The method includes continuously monitoring capacitance of a capacitive sensor to detect changes in dielectric constant of the engine lubricant, storing values representative of the capacitance in a memory, performing trend analyses of the stored values to characterize variation of the stored values, and estimating a recommended oil-change interval based on at least one of the trend analyses. Performing trend analyses may include examining variation in an oil parameter since a previous oil change, over total engine operating hours, or over a predetermined portion of the total engine operating hours. In one embodiment, trend analyses include comparing a current engine oil measurement and rate of change to previously stored values to determine the type of engine oil added to the lubrication system. In another embodiment, the method includes monitoring changes in engine oil viscosity and determining a recommended oil change interval based on changes in the viscosity and changes in the capacitance of the oil sensor.

In another embodiment of the present invention the method includes determining whether fuel dilution or coolant contamination may be present and alerting an operator in response thereto. In still another embodiment, a method of the present invention determines whether lubricating oil has been added to the lubrication system by detecting an improvement in oil quality coupled with a change in oil level. When oil addition is detected, stored calibration data is modified to adjust future calculations of recommended oil change intervals. The method also includes automatic detection of an oil change by detecting significant changes in at least one measured oil parameter.

The above objects and other objects, features, and advantages of the present invention will be readily appreciated by one of ordinary skill in the art from the following detailed description of the best mode for carrying out the invention when taken in connection with the accompanying drawings.

BRIEF DESCRIPTION OF THE DRAWINGS

FIG. 1 is a block diagram of a system constructed in accordance with the present invention;

FIG. 2 is a schematic view of one embodiment of the invention;

FIG. 3 is a schematic view of a second embodiment of the invention;

FIG. 10 is a sectional elevation of an electromagnet according to the present invention showing a 0° particle flux pattern;

FIG. 11 is a sectional elevation of an electromagnet according to the present invention showing an 80° particle flux pattern;

FIG. 12 is a sectional elevation of another embodiment of an electromagnet according to the present invention.

BEST MODE(S) FOR CARRYING OUT THE INVENTION

Figure 4:
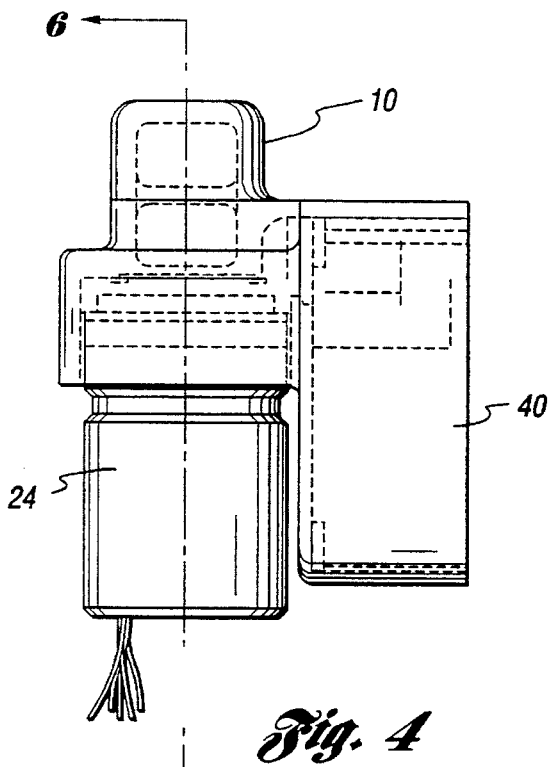
FIG. 4 is an elevational end view of a third embodiment of the invention.
Figure 5:
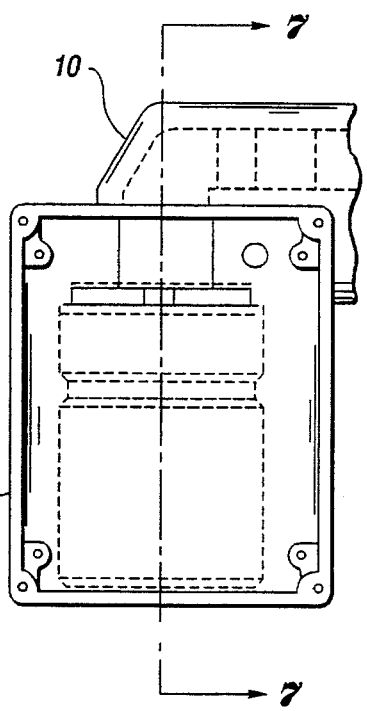
FIG. 5 is an elevational side view of the embodiment illustrated in FIG. 4.
Figure 6:
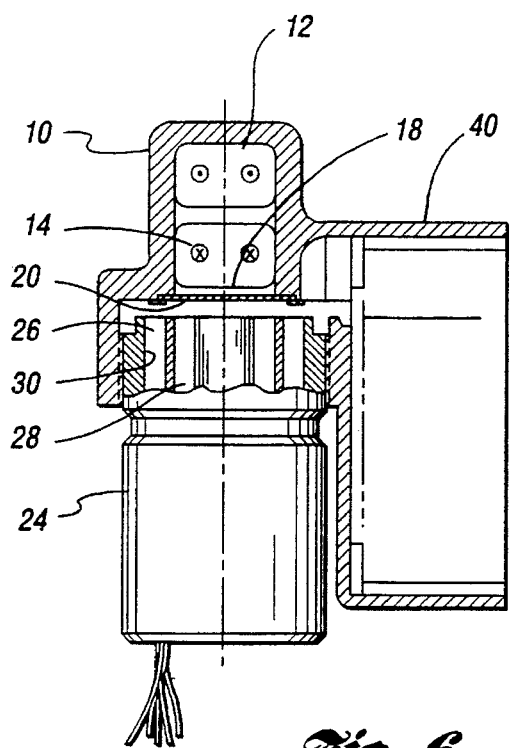
FIG. 6 is a sectional elevation of the embodiment of FIG. 4 taken along cutting plane 6—6.
Figure 7:
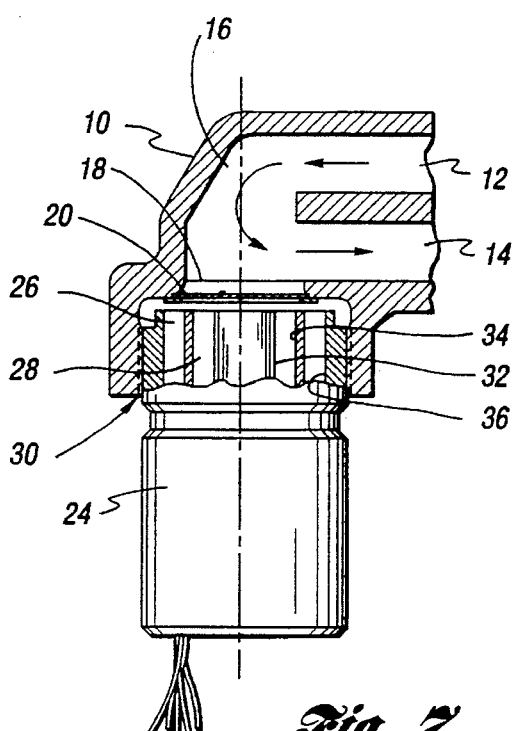
FIG. 7 is a sectional elevation of the embodiment of FIGS. 4 and 5 as viewed along cutting plane 7—7 of FIG. 5.

Relative to the drawings wherein like reference characters designate like or similar elements throughout the several FIGS. of the drawings, FIG. 1 schematically represents the basic elements of one embodiment of the invention.

Sensor element 20 of the combination comprises an open grid of two conductors 42 and 44 bonded to a non-conductive base (not shown). Each conductor has parallel circuit extensions arced as concentric half-circles. A sampling of the oil to be tested by the invention, whether by static batch or by operating circulation route, wets the surface of sensor element 20 and occupies lateral space between the conductor extensions. The oil present between the concentric semicircular conductors functions as an insulating dielectric. Thus, when an electric potential difference is placed across conductors 42 and 44, the conductors function as capacitor plates having a capacitance which is a function of the surface area of the adjacent conductors, the distance between adjacent conductors, and the dielectric strength of the oil interposed therebetween as related by Equation 1:

$$C = k \cdot E \, (A/d) \qquad (1)$$

where:

C is the capacitance of the sensor k is the dielectric constant of the oil

E is the electric potential

A is the surface area of the sensor, and d is the distance between conductors.

The dielectric strength of the oil will change during machine use due to contamination and, frequently, due to temperature increase, thereby altering the capacitive characteristics of sensor element 20. Increase of capacitance due to an increase in the dielectric strength causes an overall decrease in the frequency produced by the oscillator 50. The presence of polar oxides in the oil also causes an increase in the dielectric constant. Additionally, since water has a greater permittivity than oil, its presence in the oil will cause an increase in the effective dielectric constant for the sensor as the water settles into the vicinity of the sensor element 20.

As conductive contaminants accumulate between conductors 42 and 44, the capacitance of sensor 20 decreases until it is difficult to measure. If a substantial quantity of water accumulates on the sensor element 20, an electrical short circuit between conductors 42 and 44 may result. As the capacitance decreases and the conductivity increases, changes in conductivity are more amenable to measurement than changes in capacitance since capacitance approaches zero. Thus, changes in conductivity may be analyzed in a similar manner to changes in capacitance as described below. Such characteristic changes in capacitance and/or conductivity indicative of changes in oil quality are a basic operating principle of the present invention.

Changes in the effective dielectric constant may also result from temperature variation. However, a number of strategies may be utilized to compensate for such changes over wide operational ranges. One such compensation technique is to establish a comparative reference sensor exposed to a control fluid. Another technique includes archiving respective capacitance values corresponding to various temperatures for fresh oil, measuring the operating oil temperature, and comparing the operating oil capacitance value to the archived value at the corresponding temperature. Of course, determining and archiving a dielectric constant value or other such parameter rather than the capacitance value would provide similar results.

A wide range of fabrication parameters are suitable for the sensor element depending upon the particular application. One such successful combination uses an over-all sensor element 20 having a diameter of about one inch. The conductors 42 and 44 have a wire diameter of about 250 microns and are spaced apart by a distance of about 250 microns. A sensor element 20 having these physical parameters has a nominal air capacitance (i.e. not immersed in fluid) of about 30 picofarads. When designed for continuous operation in harsh environments of solvents and high temperatures, inorganic materials such as aluminum ceramic should be considered for fabrication of the conductor substrate.

With continuing reference to FIG. 1, the sensor element 20 is charged by an oscillator circuit 50 via conductors 42 and 44 using a monostable multivibrator to generate an output signal at a frequency corresponding to the sensor element capacitance. This variable frequency output signal is transmitted to control logic 52, which may be realized using any of a number of processing strategies without departing from the spirit or scope of the present invention. Depending upon the design parameters of the particular application, including design costs, production volume, and computational requirements, control logic 52 may be implemented in hardware, software, or a combination thereof.

In a preferred embodiment, control logic 52 is implemented using a programmed microprocessor, such as an HCMoss unit Model MC68HC705C8 with erasable, programmable, read-only memory (EPROM). Control logic 52 responds to an array of frequency variation patterns to determine the presence and magnitude of corrosive products, contamination, ferromagnetic particles, and non-ferrous metallic particles present in the lubrication oil. The results of such determinations are displayed or reported to an appropriate display console 54 that is usually, but not necessarily, located at a convenient position for monitoring by an operator remote from the sensor element. For example, in a vehicle application, display 54 may be located within the interior of the vehicle, whereas in a marine application display 54 may be an integral part of the captain's instrument panel.

Power switching units 56 and 58 are in communication with control logic 52 which coordinates their operation to effect control of electromagnet 24 via coils 26 and 28. Conductors 45 and 46 connect outer winding 26 to power supply 56 while conductors 47 and 48 connect inner winding 28 to corresponding power supply 58.

With respect to FIGS. 2 through 11, a preferred embodiment of the present invention uses a concentric dual coil configuration of electromagnet 24 having an inner coil 28 wound about a ferrite rod core 32. Surrounding the inner coil 28 is an intermediate ferrite cylinder core 34. Concentrically surrounding the intermediate cylinder core 34 is an outer coil 26 which is concentrically surrounded by an outer casement 36, also of ferrite. Preferably, all of these electromagnet elements are electrically insulated and sealed together by a non-conductive potting compound to form a single integrated unit.

It will be understood that although the presently preferred embodiment of the invention specifies a radially concentric, dual coil electromagnet, other configurations such as three or more radially concentric coils may be used. Also, axially separated coils wound about a common ferrite rod core may be used. This arrangement is illustrated in FIG. 12 where axially separated coils 64 and 65 are would about common ferrite rode core 66.

FIG. 2 schematically depicts an embodiment of the present invention particularly suited for a static test of a fixed or known volume oil sample which is confined within a vessel 70. Sensor element 20 and electromagnet 24 are removably sealed to vessel 70 to form an integral analysis unit during testing. The test unit is designed and erected to put the oil sample in direct, wetting contact with the sensing face of sensor element 20. In this state, electromagnet 24 is controlled to generate a flux field 60 within the oil sample enclosed by vessel 70. If present within the oil sample, magnetically responsive particles 62 will be attracted to the wetted face of sensing element 20. An accumulation of such magnetically responsive particles on sensor element 20 increases the capacitance in accordance with Equation 1.

Consistent with the prior art pattern of fixed volume static tests, a programmed test cycle is completed with the sensor element 20 immersed in the oil sample. At the cycle conclusion, the vessel 70 is carefully drained and removed from sensor element 20 leaving the magnetically responsive particles 62 visually exposed for further study. Manipulation of the magnetically responsive particles 62 by the control logic via power switching units 56 and 58 may facilitate visual studies of a sample.

FIG. 3 represents an embodiment of the invention similar to that of FIG. 2 except that the oil sample chamber 71 is served by a circulation shunt 76/77 drawn from a primary machine lubrication system 72 driven by pump 74. Valves 78 are positioned in the shunt circuit 76/77 to facilitate removal of chamber 71 for visual inspection of accumulated debris deposit on sensor element 20. In the embodiment of FIG. 3, chamber 71 represents a standard static test volume acted upon by a flux field produced by electromagnet 24. Thus, test samples from a number of machine circulation systems 72 may be analized by a central analysis unit.

Alternatively, valves 78 of FIG. 3 may be throttled to a predetermined flow rate through the shunt lines 76/77 driven by the pressure differential between the pump 74 intake and discharge conduits. In this mode, sensor element 20 capacitively measures the amount of contaminated magnetic extracted by the magnetic field in a measured period of time from a known flow quantity of oil. When the measuring interval ends, the electromagnet is completely de-energized to release the material captured by the sensor element.

In another alternative operational mode for the embodiment of FIG. 3, valves 78 are controlled by control logic 52 to effect two circulation flow rates: a lesser flow rate through chamber 71 for measuring the contamination concentration present in the circulation system, and a greater flow rate for flushing the sensor of magnetically responsive material accumulated during the preceding measuring interval. Normally, electromagnet de-energization would be coordinated with the greater flow rate to increase the effectiveness of the flushing cycle.

Another embodiment of the present invention is described with respect to FIGS. 4 through 7 which illustrate a non-ferrous housing 10 having lubrication oilflow conduits 12 and 14 with a chamber 16 formed therebetween. This embodiment may represent a permanent appliance installed on a machine with sensor element 20 disposed directly beneath a port 18 below the vertical chamber 16 in a sealing assembly that prevents oil leakage from chamber 16 onto the face of concentric winding coils 26 and 28 of electromagnet 24.

Internally threaded socket 30 within housing 10 receives the coil head of electromagnet 24 to axially align the magnet core 32 with the vertical axis of chamber 16. Integrally cast alongside housing 10 is an electronic control component housing 40 for protecting oscillator 50, control logic 52, and switching units 56 and 58.

The embodiment illustrated in FIGS. 4 through 7 will normally not be disassembled for visual inspection of debris accumulation on the surface of sensor element 20. Consequently, to facilitate periodic test repetition, it is important that the sensor element be self-cleaning during ordinary operation of the machine lubrication system. To accomplish this requirement, it is preferable to operate the switching units 56 and 58 so as to remove all magnetic flux from the proximity of the sensor element 20 and release debris accumulated from each test sequence back into the lubrication flow stream.

Each switching unit 56 and 58 has various functional states controlled by control logic 52 which may be characterized as: (1) "off" or de-energized; (2) "on" with positive polarity; and (3) "on" with negative polarity. Furthermore, the "on" states may include various power levels to help ascertain contaminant characteristics as explained in greater detail below. The operational effect of these functional states on the magnetic flux lines produced by electromagnet 24 is depicted in FIGS. 8 through 11. Data corresponding to the functional states illustrated in FIGS. 8 through 11 are shown in Tables 1 through 4 below.

Figure 8:
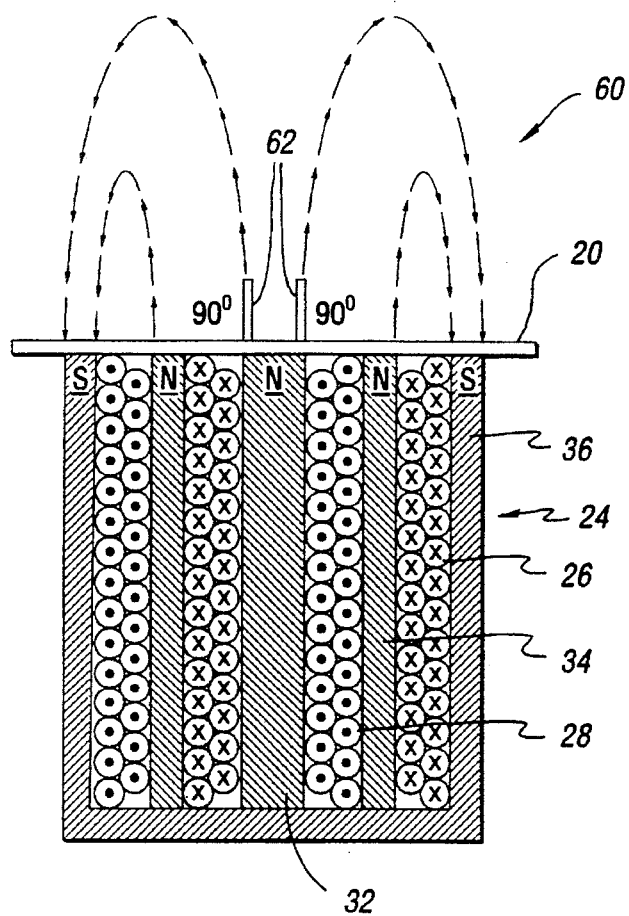
FIG. 8 is a sectional elevation of an electromagnet according to the present invention showing a 90° particle flux pattern.
Figure 9:
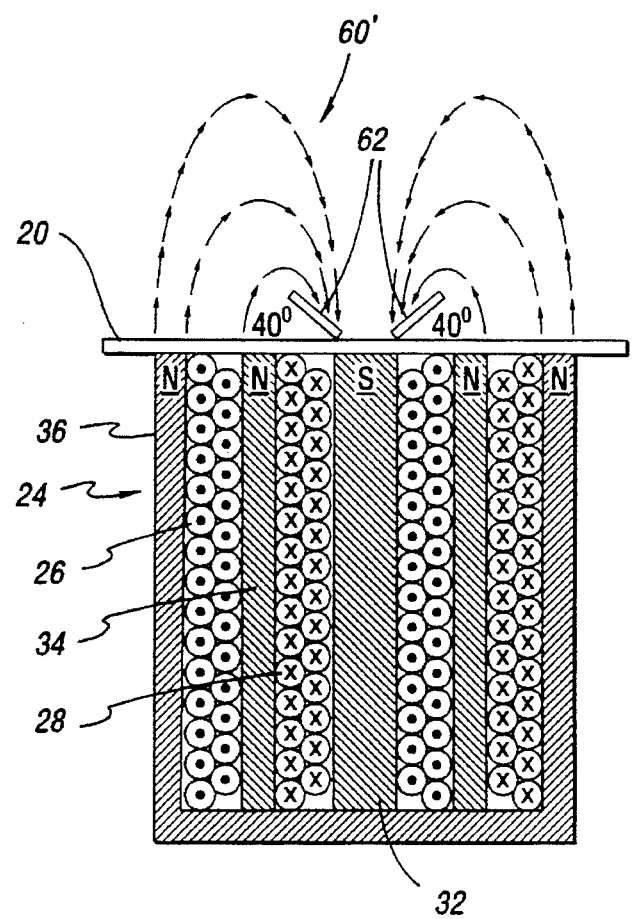
FIG. 9 is a sectional elevation of an electromagnet according to the present invention showing a 40° particle flux pattern.

The flux pattern 60 of FIG. 8 corresponds to the field strength (in gauss) and polarities represented by the Table 1 data. A positive, twelve-volt charge on outer coil 26 and a de-energized inner coil 28 produces the maximum response angle of about 90° relative to the plane of sensor element 20 for magnetically responsive particles 62. When the coil power state is reversed to provide a de-energized outer coil 26 and a negative twelve-volt charge on inner coil 28, the flux pattern 60' of FIG. 9 is produced which positions the magnetically responsive particles 62 at about 40° relative to the plane of sensor element 20. Data obtained from this functional state are presented in Table 2 below.

Table 3 data correspond to flux pattern 60" of FIG. 10 in which the magnetically responsive particles 62 are positioned parallel to sensor element 20 by a positive, twelve-volt charge on the outer coil and a negative twelve-volt charge on the inner coil.

Table 4 data correspond to a functional state providing a positive twelve-volt charge to both inner and outer coils to produce flux pattern 60''' of FIG. 11. As illustrated, magnetically responsive particles 62 are attracted to sensor element 20 at an angle of about 80° relative to the plane of the sensor element 20.

TABLE 1

+12 VDC Outer Coil; 0 VDC Inner Coil

| Magnet # | Center | Tube | Case |
|---|---|---|---|
| 1 | 438 | 411 | −198 |
| 2 | 522 | 442 | −202 |
| 3 | 542 | 425 | −214 |
| 4 | 547 | 432 | −202 |
| 5 | 536 | 445 | −203 |
| 6 | 550 | 428 | −204 |
| 7 | 540 | 429 | −211 |
| Mean: | 525 | 430.5 | −204.9 |
| S. Dev: | 3.94 | 11.3 | 5.6 |

TABLE 2

0 VDC Outer Coil; −12 VDC Inner Coil

| Magnet # | Center | Tube | Case |
|---|---|---|---|
| 1 | −845 | 88 | 58 |
| 2 | −913 | 109 | 42 |
| 3 | −900 | 123 | 43 |
| 4 | −930 | 122 | 50 |
| 5 | −890 | 130 | 39 |
| 6 | −899 | 127 | 41 |
| 7 | −940 | 129 | 47 |
| Mean: | −902.4 | 118.3 | 45.7 |
| S. Dev: | 31 | 15.1 | 6.6 |

TABLE 3

+12 VDC Outer Coil; −12 VDC Inner Coil

| Magnet # | Center | Tube | Case |
|---|---|---|---|
| 1 | −509 | 466 | −106 |
| 2 | −620 | 490 | −120 |
| 3 | −606 | 468 | −108 |
| 4 | −639 | 493 | −114 |
| 5 | −594 | 491 | −118 |
| 6 | −612 | 477 | −112 |
| 7 | −650 | 508 | −130 |
| Mean: | −615.9 | 484.7 | −115.4 |
| S. Dev: | 22.3 | 15.1 | 8.1 |

TABLE 4

+12 VDC Outer Coil; +12 VDC Inner Coil

| Magnet | Center | Tube | Case |
|---|---|---|---|
| 1 | 1150 | 344 | −243 |
| 2 | 1235 | 385 | −250 |
| 3 | 1205 | 378 | −250 |
| 4 | 1243 | 371 | −250 |
| 5 | 1202 | 382 | −256 |
| 6 | 1213 | 381 | −242 |
| 7 | 1250 | 360 | −250 |
| Mean: | 1214 | 371.6 | −248.7 |
| S. Dev: | 33.9 | 14.8 | 4.8 |

By a selective switching test effected by control logic 52, magnetically responsive particles carried by the oil are attracted to sensor element 20 and caused to positionally fluctuate in characteristic patterns distinctive to their size and shape.

Most wear particles in a lubricant result from three root causes: adhesive wear, abrasive wear, or metal fatigue. Adhesive wear is that which results from sliding, scuffing, or rubbing contact between surfaces. Sliding type adhesive wear is common and quite normal Wear which occurs in most applications. Scuffing and rubbing contact typically result from a component or lubrication failure and are, therefore, not normal. Normal adhesive wear generates very small (0.1 to 5 microns) wear particles as high spots of components in sliding engagement are sheared down. Abnormal adhesion (resulting in scuffing or rubbing) may generate much larger particles.

Abrasive wear is the cutting action typically caused by hard particles gouging out relatively long strips (ranging between ten and several hundred microns) of metal which are sometimes curled. Sand or metal wear particles are frequently the cause of abrasive wear. Abrasive wear particles are eventually broken into smaller particles as they are acted upon by various contacting machinery components.

Metal fatigue (also called "high cycle fatigue") occurs when a metallic component fails due to repeated cyclic loading. This is a common failure mode for various machine components such as gear teeth and roller element bearings which are utilized in a number of diverse industrial and commercial applications. Fatigue particles tend to be relatively large (10 to 20 microns) having a parallelepiped or a spherical shape. The presence of spherical particles usually is particularly indicative of fatigue failure. These particles are generated when sub-surface cracks allow a portion of material to break free. When the surface-connected cracks join and produce a parallelepiped surface particle, the sub-surface spherical particles are also released.

By capturing various types of wear particles, the present invention improves the efficiency of diagnosis and appropriate repairs prior to a system failure. Once the wear particles are captured by the sensor element of the present invention, a careful examination of the quantity and character of the particles provides valuable insight into their source. Maintenance and operations personnel may then pursue the correct follow-up actions. For instance, after detecting abrasive wear particles in a machine, the oil and filter should be changed. Seals and air filters should be inspected to determine how sand or dirt might be getting into the lubrication system. Other such appropriate diagnostic and corrective actions can be likewise pursued upon detection of any of the other types of wear particles.

With continuing reference to FIGS. 9 through 11, positional fluctuation or rotation of ferrous particles 62 is accomplished by switching polarity between the electromagnet core 32 and the intermediate cylinder core 34 from a similar polarity (e.g. N—N or S—S) to an opposing polarity (e.g., N—S or S—N). The ferrous particles within the oil sample above the sensor will naturally collect where magnetic flux lines are concentrated about a circle projected from the outside diameter of electromagnet core 32. When the electromagnet core 32 and the intermediate cylinder core 34 have similar polarity (FIGS. 8 and 11), the flux lines passing through electromagnet core 32 will have a high axial trajectory in avoidance of the flux lines produced by the intermediate cylinder core 34. When the electromagnet core 32 and intermediate cylinder core 34 have opposite polarity (FIGS. 9 and 10), the flux lines passing through electromagnet core 32 will have a low trajectory due to the attraction to the flux lines produced by intermediate cylinder core 34.

By cycling through the various charging conditions of the electromagnet, an oscillation in orientation of ferrous particles 62 is produced. As evidenced by the data of Tables 1 through 4, the present invention provides similar results as those provided by U.S. Pat. No. 5,262,732 to A.D. Dickeft et al using alternative apparatus and methods. The several test sequences and algorithms disclosed by Dickert et al are hereby adopted as directly applicable to the present invention and integrated herewith by reference. For example, by switching between the outer and inner coils (Tables 1 and 2), polarity reverses between N—N to S—N. In another example, by powering up the outer coil and switching between three states of the inner coil (off, −12V, +12V, etc.) polarity changes from N—N to S—N to N—N, etc.

Since the dual-winding electromagnet configuration of this invention can be a direct substitution for the electromagnet plus permanent magnet configuration disclosed by Dickert et al, all of the computational indices disclosed therein are equally adaptable to the present invention. Those include the Corrosion Index, Contaminant Index, Ferrous Index, OilLife® Index, and Large Contaminant Indication. The present invention provides for similar measurements to be obtained from a stagnant oil sample in a manner similar to that disclosed by Dickert et al. However, a number of additional measurements and indications may be obtained while a lubricating oil is flowing over the sensor. Thus, the present invention has all of the advantages accruing to the Dickert et al disclosure plus the further advantage of selectively collecting and releasing ferrous debris in a flowing system.

In a machine lubrication system, for example, measurements provided by sensor 20, taken while the oil is flowing and the electromagnet windings are both "off", are directly related to the initial few seconds of data collected from a well-shaken, stagnant oil sample of the Dickert et al disclosure. This is because the oil is well mixed and contaminants are dispersed when the oil is flowing within a lubrication system. Therefore, the Corrosion Index for an in-line sensor can be measured continuously while the oil is flowing in addition to being measured immediately after flow ceases.

In another example, the electromagnet windings of the present invention can be used in a flowing system to collect wear debris on the sensor grid. The key to this is to use the magnetic forces to overcome the viscous fluid shear forces of the oil which tend to keep the contaminants suspended. Once the wear debris has been collected on the sensor grid 20 by the electromagnet(s), it can be oscillated through angular orientations to quantify the concentration and size in the same manner as the Ferrous Index and large contaminant indications described in Dickert et al. Visual analysis of the particles is not essential to these conclusions.

Electrically charged particles and ionic species are not as susceptible as metallic particles to viscous shearing forces. As such, additive dispersed soot particles, water, glycol coolant, and other contaminants can be detected and quantified using a capacitive sensor 20 when the oil is flowing in a manner analogous to that described in Dickert et al for a stagnant sample. Positively and negatively charged contaminants can be distinguished by reversing polarity on the capacitance sensor. A logical combination of this feature with switching of the electromagnets enables monitoring of many contaminants while the oil is flowing over the sensor. Furthermore, by periodically shutting power off to the sensor grid and to the electromagnets, the grid is self-cleaning.

At the conclusion of a test sequence, the accumulated debris and wear particles may be viewed directly using the embodiments illustrated in FIGS. 2 and 3 of the present invention for analysis and direct interpretation of contaminant type and origin. On the other hand, the embodiment of FIGS. 4 through 7 of the present invention inactivates the flux produced by the electromagnets and, having no permanent magnetic field, releases all contaminant accumulations to the oil circulation systems thereby cleansing the sensor element 20 in preparation for the next test sequence. Since the polarity of the electromagnets is cyclically reversed, any residual magnetic field is substantially eliminated.

Figure 13:
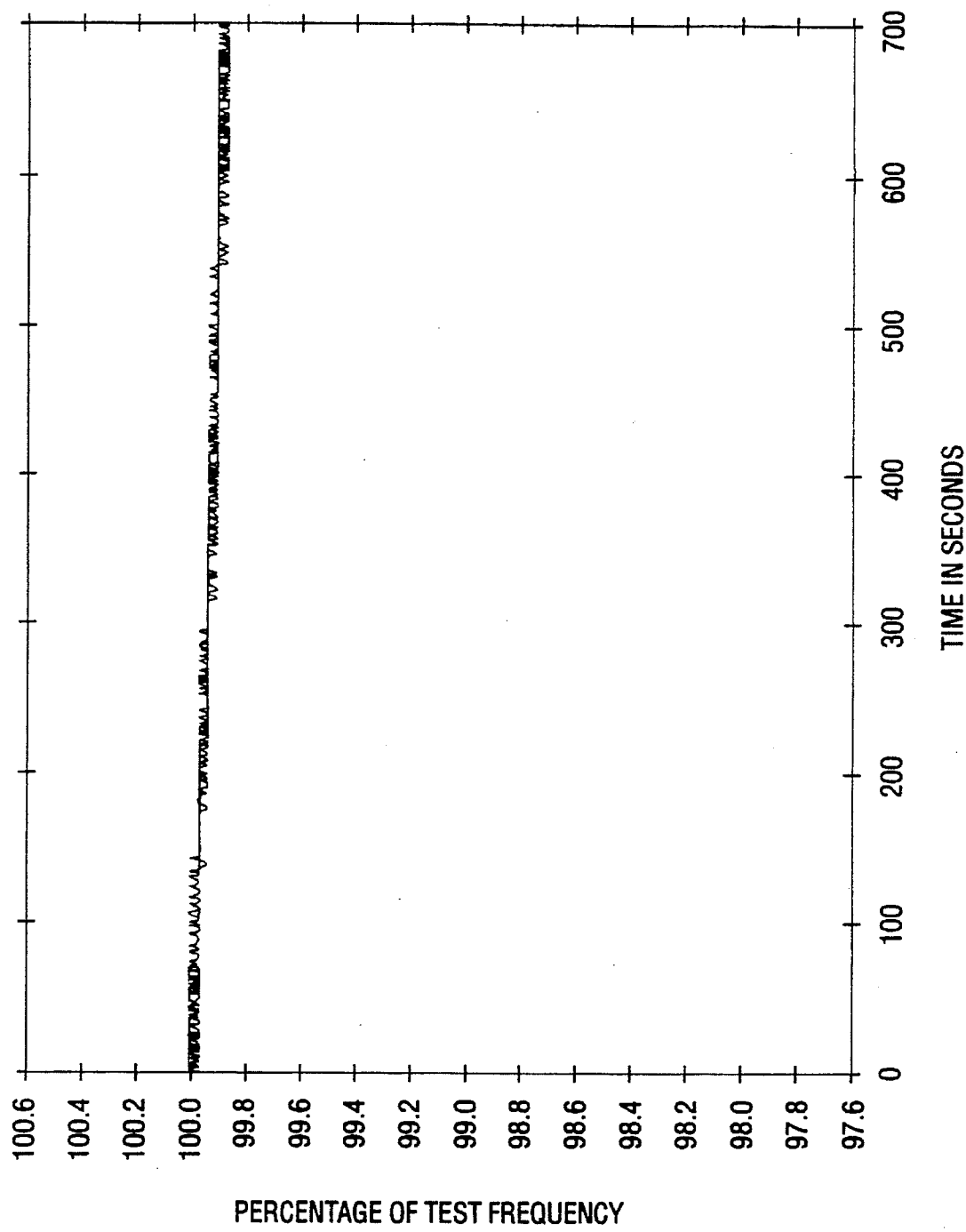
FIG. 13 is a graph of percentage of test frequency as a function of time showing baseline data obtained using uncontaminated circulating lubricating oil.

A baseline frequency response for a sensor immersed in uncontaminated circulating lubrication oil is illustrated in FIG. 13. Preferably, the sensor is excited by a nominal test frequency of 4.4 kHz. Thus, the graph of FIG. 13 illustrates a decrease of less than 0.1% of the nominal frequency, i.e. 4.4 Hz over the first 700 seconds. This baseline frequency response is characteristic to the particular type of lubrication oil and system dynamics. Thus, similar information is obtained after each oil change, or using a reference fluid during operation, to determine the type of oil in the system and to calibrate subsequently obtained oil quality measurements.

Figure 15:
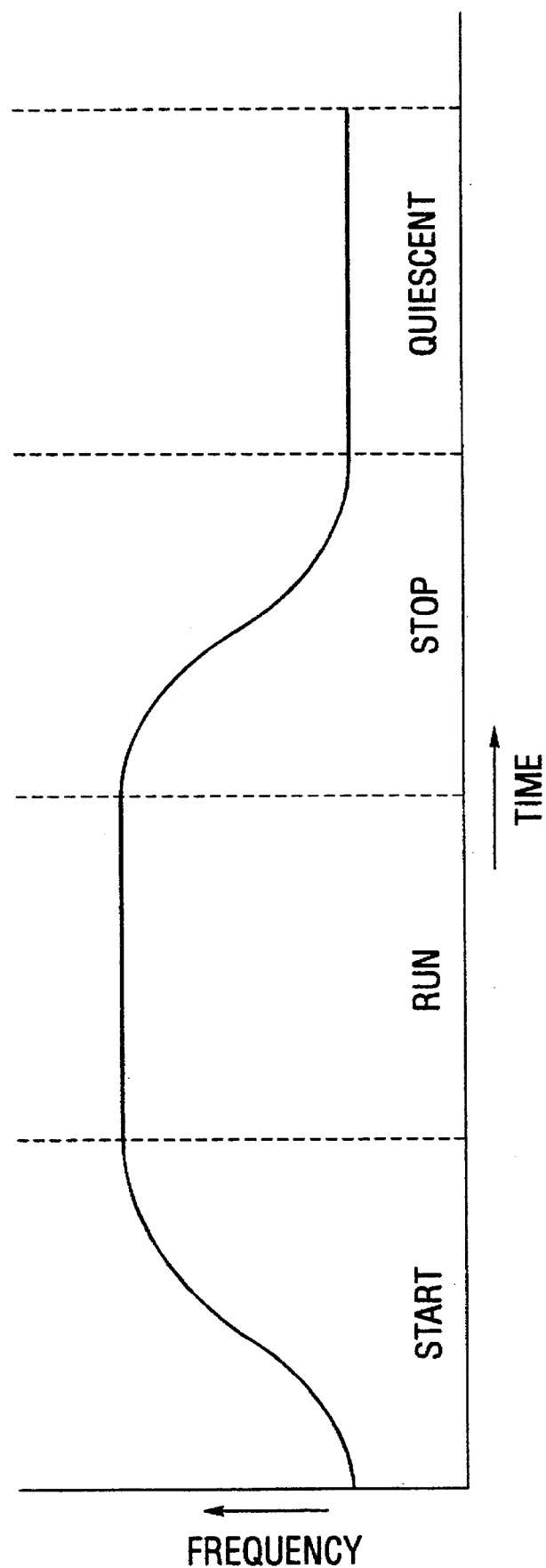
FIG. 15 is a graph of duty cycle frequency as a function of time showing data obtained using contaminated lubricating oil in an intermittently operated machine.

Intermittently operated machinery is frequently characterized by duty cycles comprising two transient phases and two steady state phases. FIG. 15 depicts the frequency response of a capacitive sensor for a typical duty cycle of an intermittently operated machine. The cold start-up transient phase is characterized by accumulations of solid contaminants upon the sensor 20 grid (due to gravity). During this phase, water and other low vapor pressure fluids have evaporated or migrated from the sensor surface. This results in a relatively low-frequency response which increases to a steady-state value as the accumulations are flushed from the sensor surface when the system begins running and the temperature rises to a steady-state value. A decrease in the response frequency during the shut-down or stop transient phase results from the abrupt cessation of hot homogenous lubrication fluid that may be mixed with water, glycol, or other coolant.

The first steady state phase of FIG. 15 is characterized by an extended running interval with continuing circulation of the hot, substantially constant temperature, lubrication fluid during which a large number of capacitance measurements will track the bulk dielectric value of the oil. For example, the median value of 500 capacitance measurements taken at ten-second intervals will remain substantially constant. Over long time periods, this value will decline as the lubricant accumulates soot, water, glycol and other contaminants. The other steady-state phase, quiescent, is characterized by a cooled lubricant which has reached its lowest temperature and may not be circulating.

During oil circulation, soot, metal and other contaminating particles are extracted by the sensor and electromagnets from the lubricant flow stream. The attractive magnetic forces of the electromagnets must overcome the fluid shear forces of the circulating fluid which tend to flush the particles from the sensor surface. To electrostatically (as opposed to magnetically) attract and hold polar and ionic particles to the sensor surface for detection and measurement, control logic 52 charges conductor leads 42 and 44 with a low D.C. voltage differential of about three volts. Cyclically alternating this charge stimulates non-ferrous charged particle oscillation and capacitance value fluctuations in a manner similar to that produced by magnetically responsive particles. It should be noted that these two strategies of the present invention for attracting magnetic and non-magnetic charged particles are functionally independent and may be engaged singularly, collectively, or alternately to produce difference and additive combinations of data for specific contaminant identification and concentration analysis.

Figure 14:
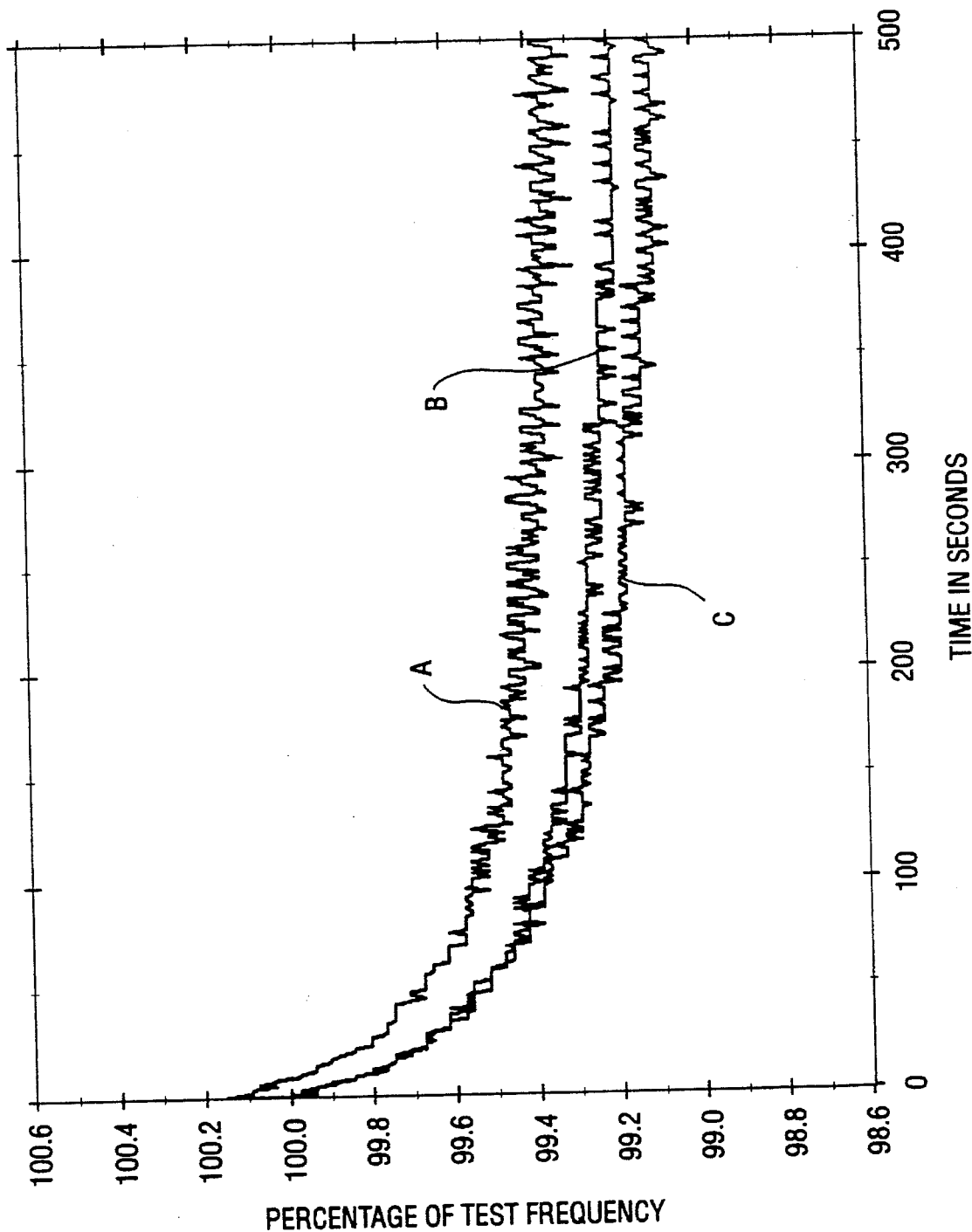
FIG. 14 is a graph of percentage of test frequency as a function of time showing data obtained using lubricating oil contaminated only by seeded iron filings under three distinct electromagnet energy states.

Data collected utilizing this analytical approach are illustrated as curves A, B, and C of FIG. 14 which depicts percentage of test frequency as a function of time (in seconds). The fluid medium of the test was fresh oil seeded with 4 to 6 micron iron particles. Particle orientation was manipulated by the electromagnet 24. Curve A of the graph was produced with the electromagnet energized to stand the iron particles vertically at about 90°. Curve B of the graph was generated with an intermediate particle angle and Curve C was resulted from the particles being laid against the sensor surface at approximately 0°.

Figure 16:
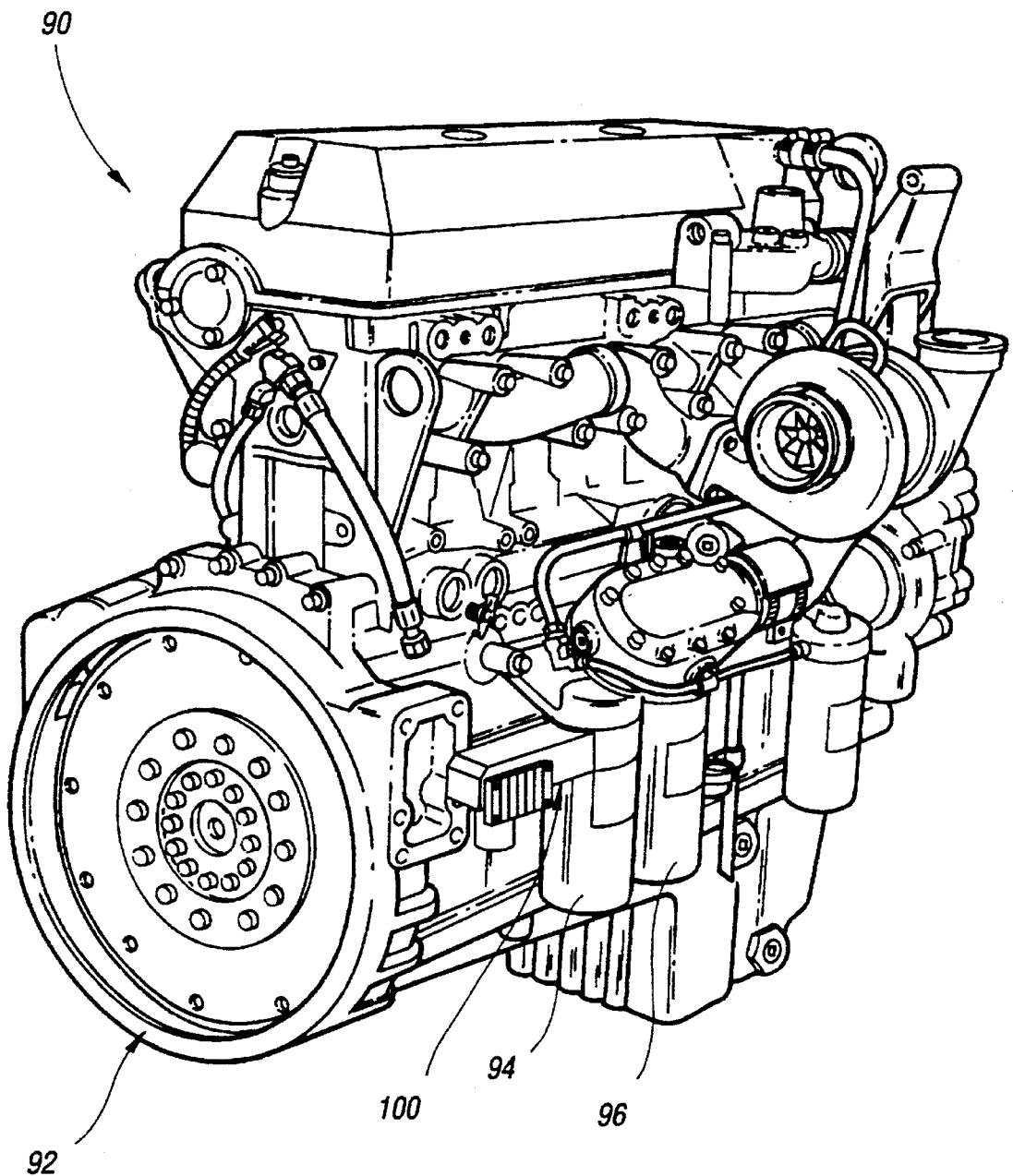
FIG. 16 is a perspective view of a heavy-duty diesel engine having an oil quality analysis system according to the present invention.

Referring now to FIG. 16, there is illustrated a perspective view of a heavy-duty diesel engine shown generally by reference numeral 90. Typically, such an engine powers a vehicle, such as a heavy-duty truck or tractor semi-trailer combination. However, a number of other applications of the present invention are possible including stationery power plants and marine applications. The engine includes a flywheel housing shown generally by reference numeral 92 which mates with a transmission, not specifically shown. As is known, the engine 90 includes a plurality of internal moving parts, such as a crankshaft, cams, and engine cylinders to name a few, not specifically shown for the sake of clarity. The engine 90 also includes a lubricant to reduce friction between these moving parts, such as an engine oil or an equivalent, which also operates to cool the moving parts during engine operation and remove wear debris.

As shown in FIG. 16, engine 90 includes a pair of engine oil filters 94 and 96 for filtering the oil during engine operation. Preferably, the oil filter 94 cooperates with an oil quality analysis sensor assembly shown generally by reference numeral 100 disposed proximate the end of the filter at which the oil enters. Most preferably, the oil filter 94 and oil quality analysis sensor assembly 100 are configured such that oil passes through the sensor for quality analysis prior to being filtered. This configuration provides advantages which will be appreciated after reading the following discussion.

Figure 17:
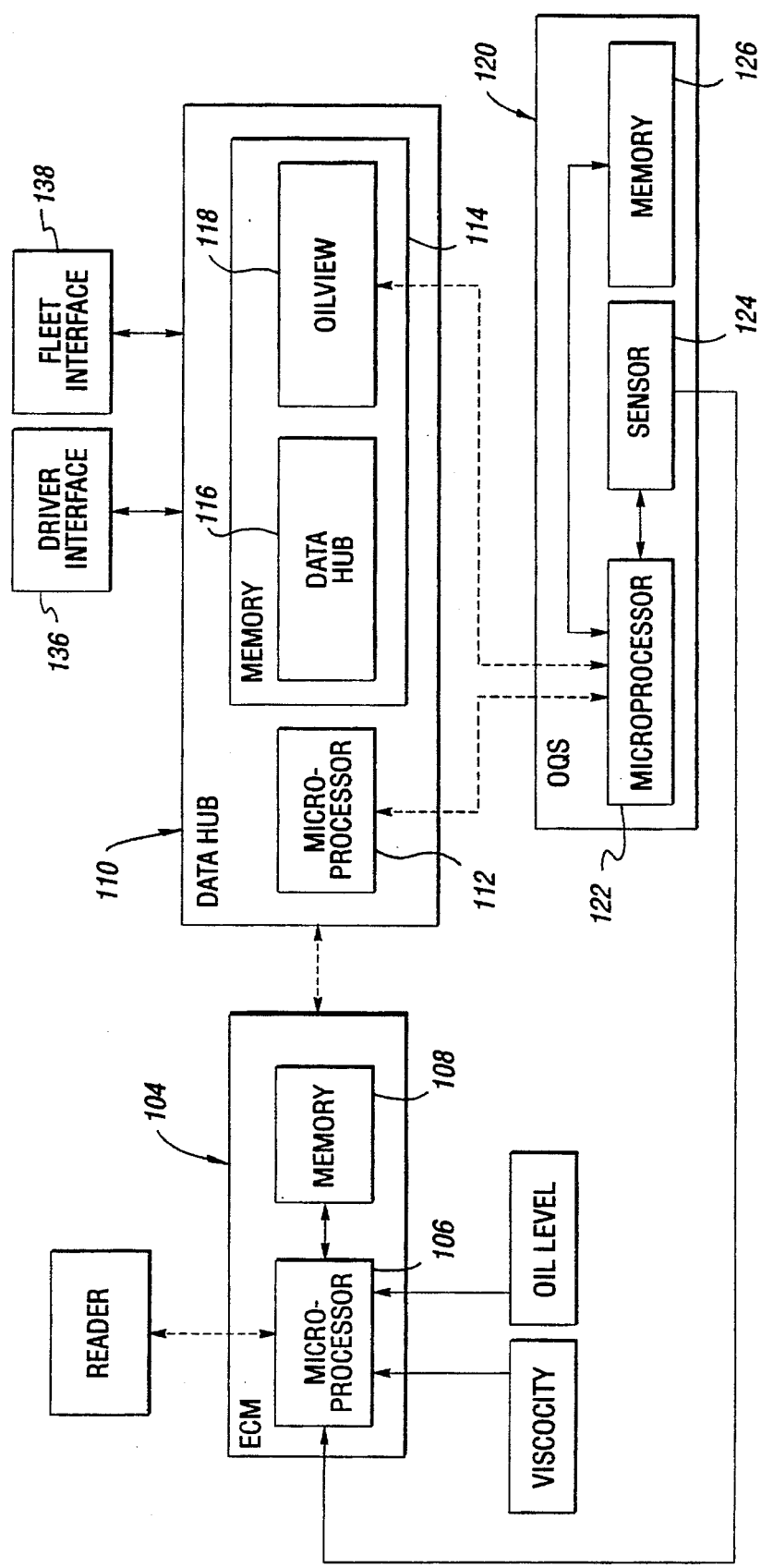
FIG. 17 is a system block diagram for implementing a method for monitoring heavy-duty diesel engine oil quality analysis according to the present invention.

Referring now to FIG. 17, there is illustrated a block diagram of a control system which, in cooperation with the engine 90, executes the methods for oil quality analysis of the present invention. As shown, the control system includes an electronic control module (ECM) 104 preferably having a microprocessor 106 and memory 108. It should be appreciated that memory 108 may include both volatile and non-volatile memory, such as random access memory (RAM) and read-only memory (ROM) or the like. It should also be appreciated by one of ordinary skill in the art that the ROM is any such non-volatile memory and could take many forms. For example, the ROM could be an EPROM or an EEPROM, and contains control logic executed to carry out the methodologies of the present invention. Similarly, ECM 104 implements control logic illustrated in FIGS. 43–48 and described below and may be realized with any combination of hardware and software depending upon the requirements of the particular application.

In the preferred embodiment, the control system includes a data hub control unit 110, which communicates in a bi-directional manner with ECM 104. As shown in FIG. 2, the data hub 110 includes a microprocessor 112 and memory 114, which includes both ROM and RAM memories. The memory 114 can be subdivided to provide memory 116 for use by data hub microprocessor 112, as well as memory 118 for use by a microprocessor 122 of an oil quality sensor (OQS) 120. As shown by FIG. 17, an oil parameter sensor 124 of OQS 120 provides data to memories 108, 114, and 126 via corresponding microprocessors 106, 112, and 122, respectively.

With continuing reference to FIG. 17, the data hub control unit 110 also preferably includes a driver interface and a fleet interface shown generally by reference numerals 136 and 138, respectively. The driver interface 136 provides a means through which information can be exchanged between the vehicle operator and the control system. To provide this functionality, driver interface 136 may include a visual display, such as a liquid crystal display or the like, as well as input means, such as input keys or buttons to facilitate the information exchange. Similarly, the fleet interface 138 permits fleet operators to program certain aspects of the control system through the data hub, as described in greater detail below.

Figure 18:
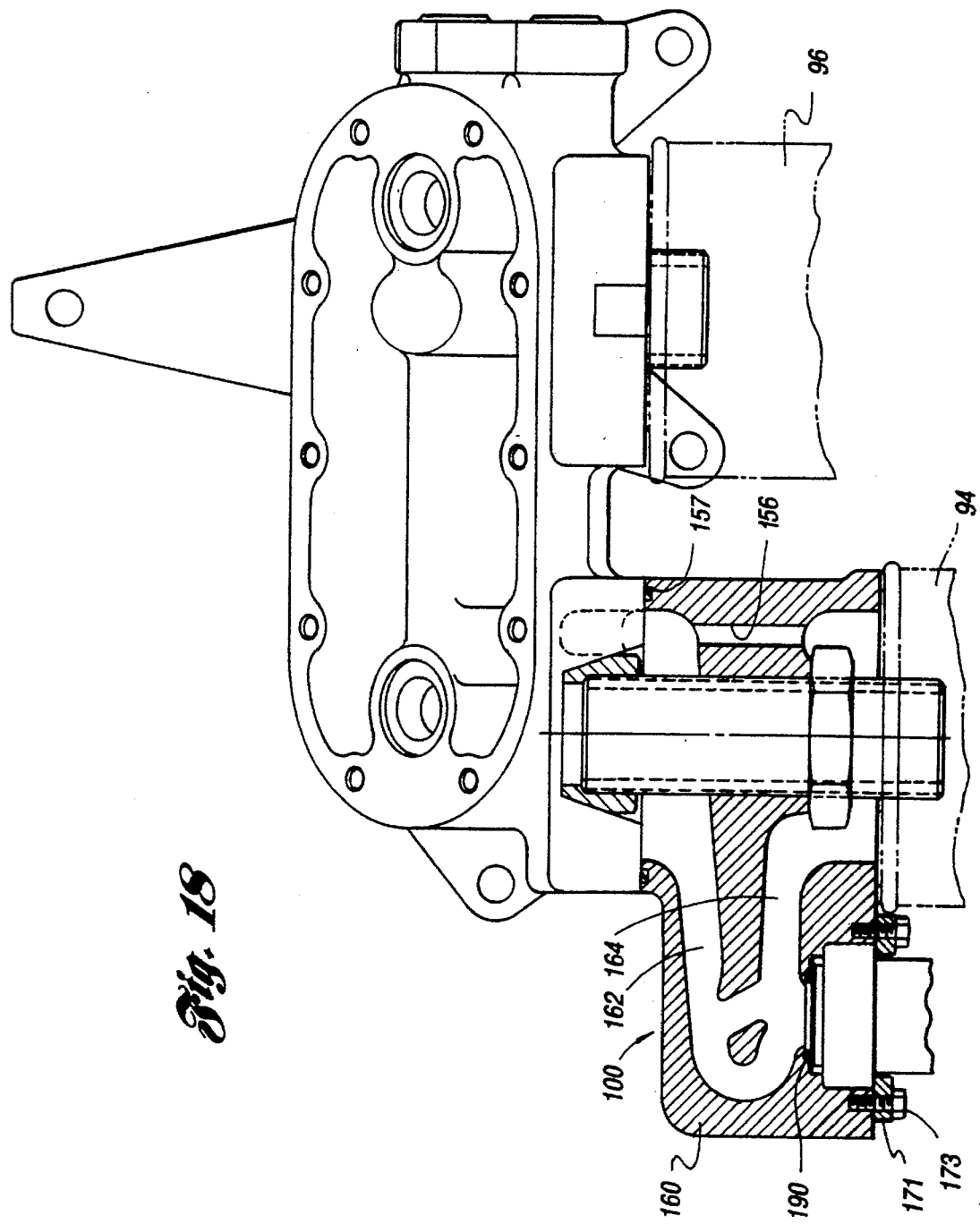
FIG. 18 is an elevational view of an oil sensor housing in cross-section according to the present invention.
Figure 19:
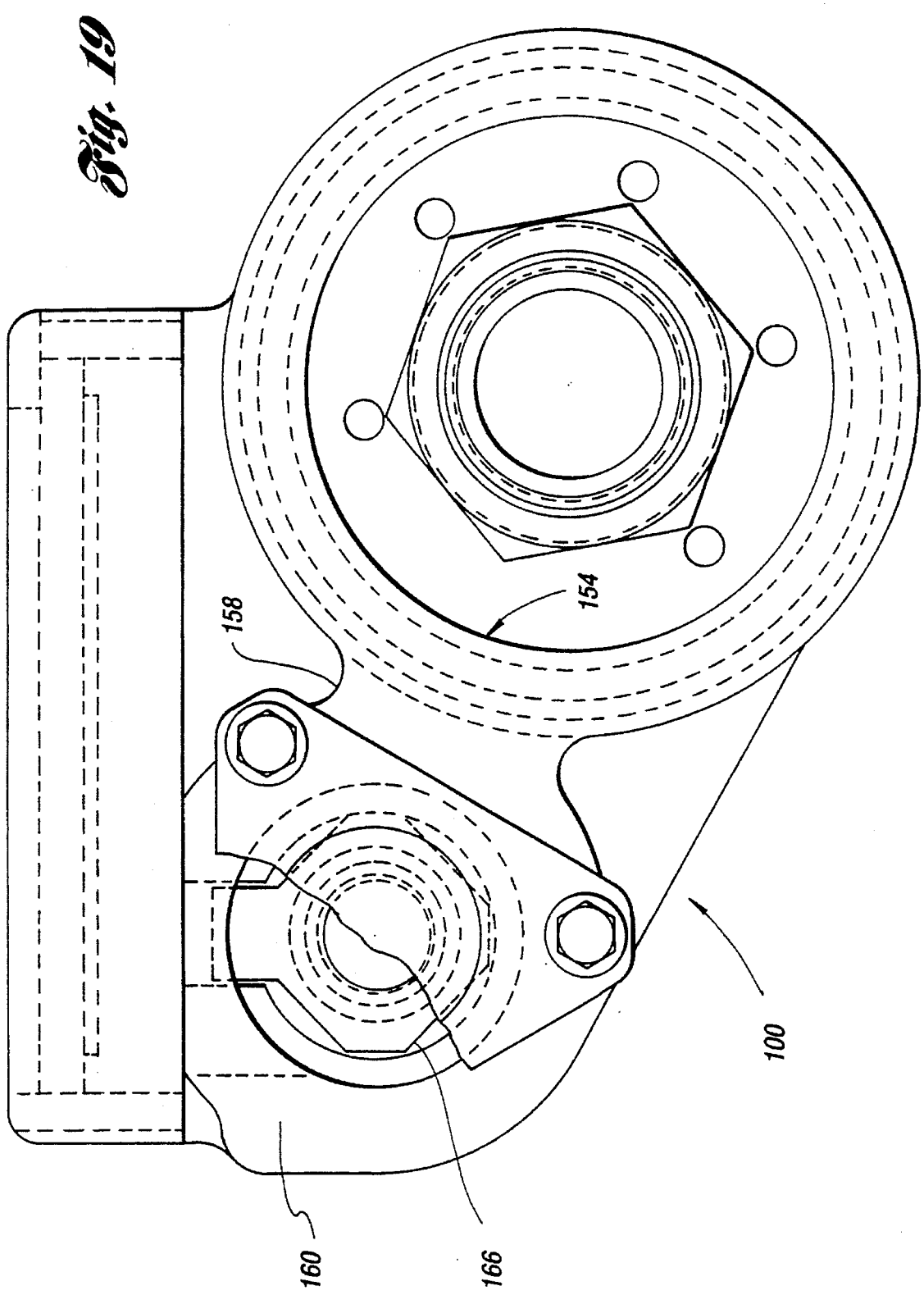
FIG. 19 is a plan view of the oil sensor housing 100 of FIG. 18.

Referring now to FIGS. 18–21, there is illustrated a single grid oil quality analysis sensor assembly 100. The oil quality analysis sensor assembly 100 includes filter ring 154 which, as best shown in FIG. 16, is sized to mate with one of the oil filters (e.g. filter 94). As shown in FIG. 18–19, the filter ring 154 includes a plurality of passages 156 through which engine oil passes to the oil filter, shunting the oil flow to relieve pressure on an O-ring 157 and thereby assuring the integrity of the seal.

With combined reference to FIGS. 18–21, the assembly 100 includes a neck portion 158 in fluid communication with filter ring portion 154. A sensor housing portion 160 is also in fluid communication via neck portion 158 with filter ring portion 154. Preferably, neck portion 158 includes at least two fluid passages disposed therein. The passage 162 delivers oil from the engine to the sensor housing, whereas passage 164 returns the oil to the filter 94 after being subjected to oil quality analysis according to the present invention. Disposed within the sensor housing portion is an oil sensor grid 166 and an electromagnet 168 which is secured to the housing via flange 169, bracket 171, and bolts 173. Optionally, a viscosity sensor may also be included at this location and used in a manner as discussed below in greater detail, particularly with reference to FIG. 38.

Figure 22:
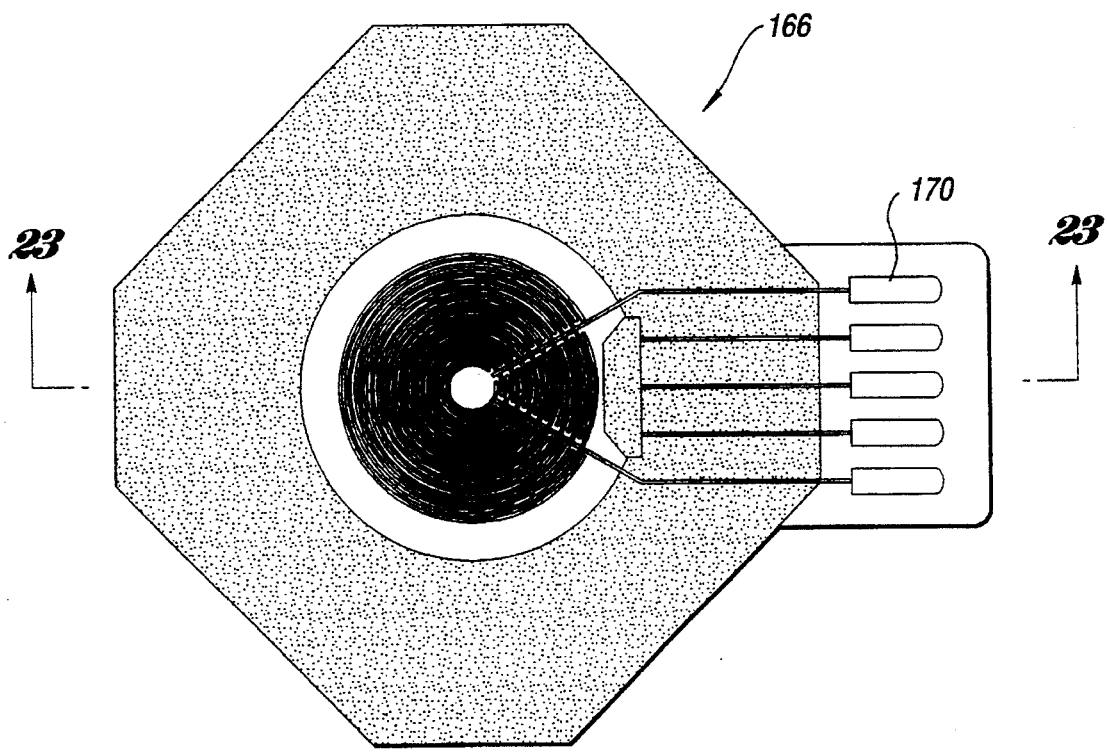
FIG. 22 is a detailed plan view of a sensor grid according to the present invention.
Figure 23:
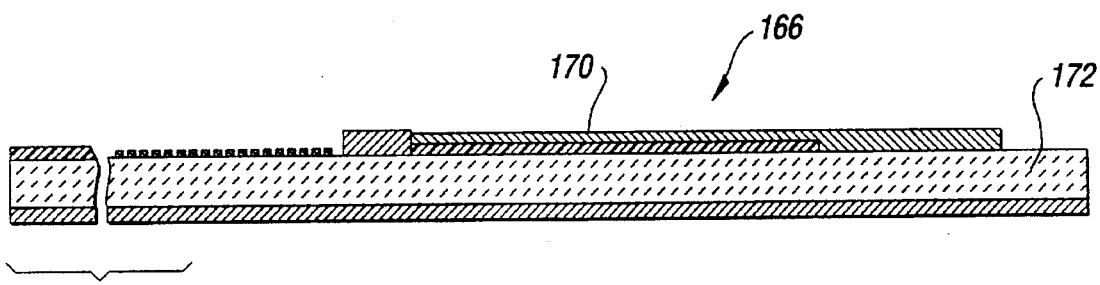
FIG. 23 is an enlarged cross-sectional view of the sensor grid of FIG. 22 taken along cutting plane 23—23.

FIGS. 22 and 23 illustrate the oil sensor grid 166. Preferably, the sensor grid 166 is constructed of a ceramic substrate 172 and includes a plurality of concentric 3-layer conductive metal traces 170 having a top layer of gold for corrosion resistance. The sensor grid 166 is positioned within the sensor housing 160 such that the traces (the gold layer) are exposed to the flow of engine oil from the passage 162 to the passage 164. An 0-ring 190 confines the engine oil and prevents the oil from leaking into other sensor housing chambers.

Figure 20:
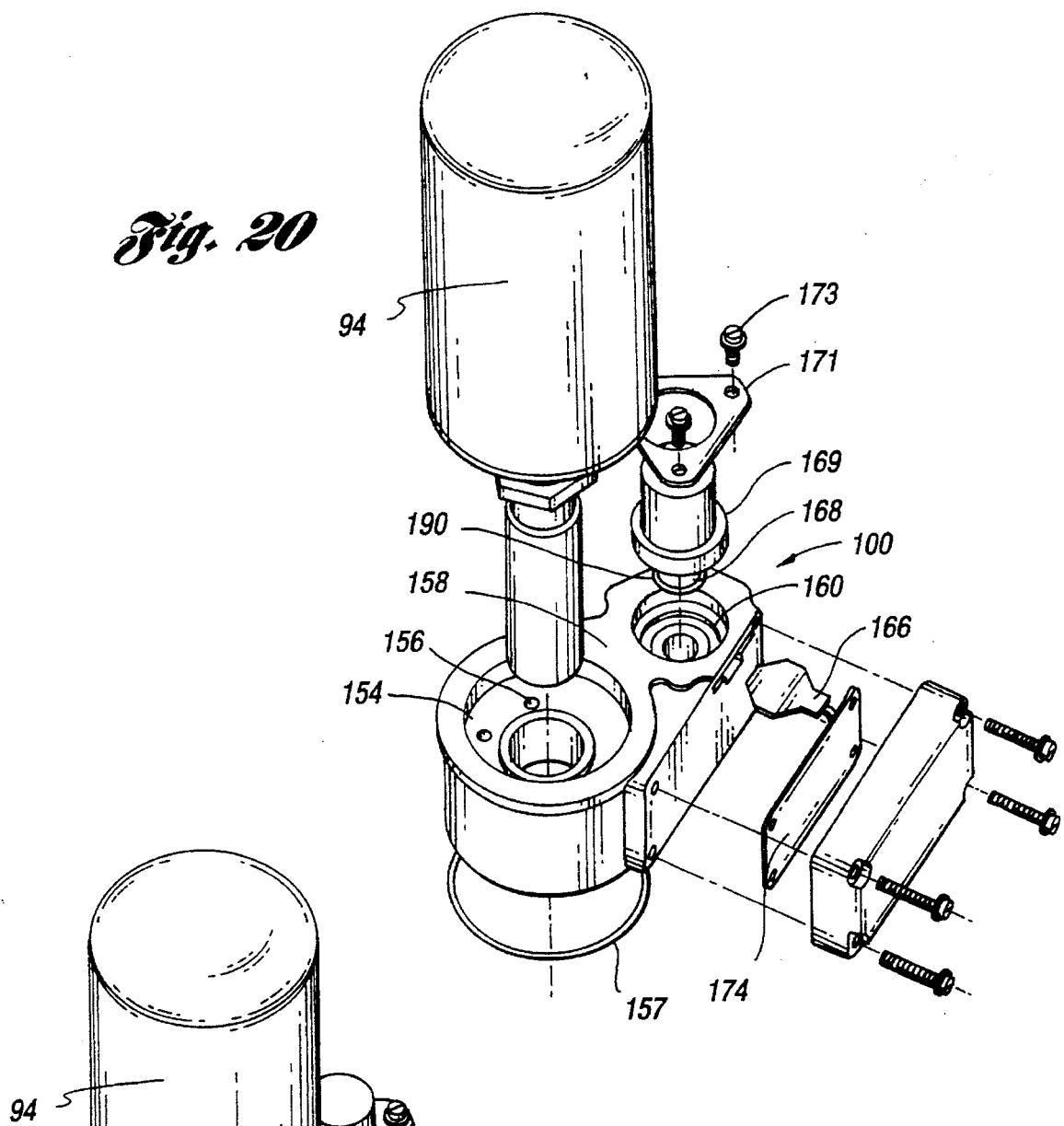
FIG. 20 is an exploded perspective view of the sensor housing of FIGS. 18 and 19 as seen from the lower end.
Figure 21:
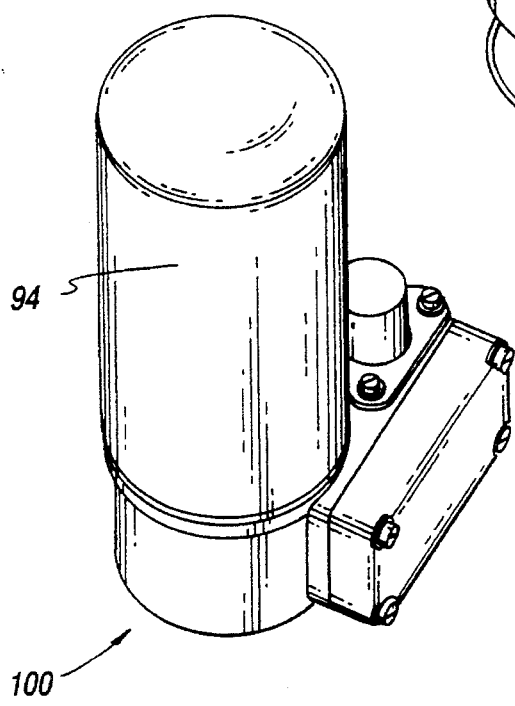
FIG. 21 is a perspective view of an assembled sensor housing as shown in FIGS. 18–20.

As shown in FIG. 20, the sensor grid 166 is in electrical communication with a circuit board 174 which includes a waveform generator which applies an appropriate signal to the sensor grid to permit engine oil quality analysis according to the present invention. The waveform is applied to the sensor grid 166 in conjunction with excitation of the electromagnet 168, which is positioned in the sensor housing 160 below (as installed on an engine) the sensor grid 166. The electromagnet 168 includes a pair of nested coils comprising an inner coil and an outer coil as illustrated and described with reference to FIGS. 9–12. In one embodiment, the waveform applied to the sensor grid is a square wave or clipped sinusoidal wave. As this waveform is applied to the grid, the inner and outer coils are energized in an alternating fashion.

Figure 24:
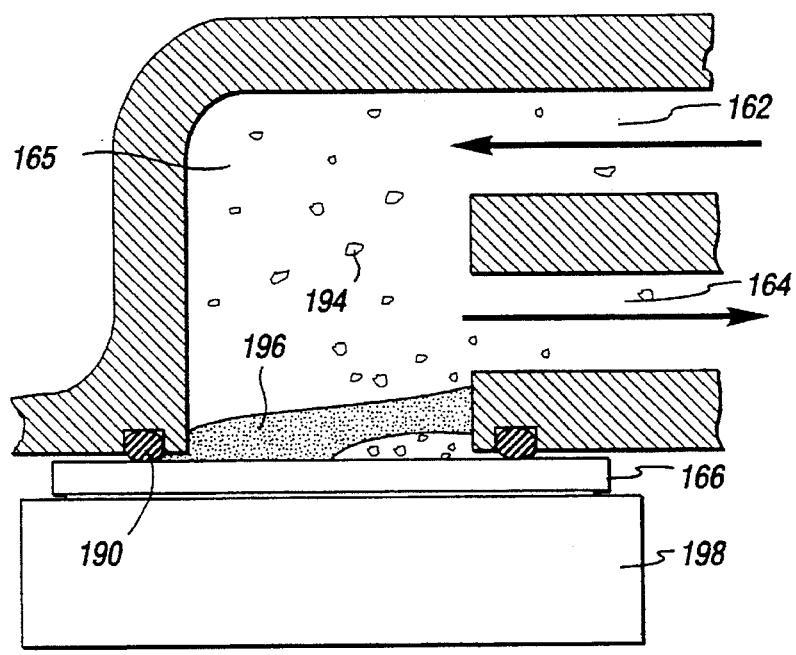
FIG. 24 shows an enlarged view of a measurement chamber filled as it might be filled during continuous engine operation depicting the oil and contaminants being analyzed under a fouling condition.

FIG. 24 shows that portion of the sensor housing including the oil inlet passage 162, measurement chamber 165, oil exit passage 164, and the sensor grid 166. This illustration depicts the oil sensor in use in a typical application wherein certain contaminants have collected on the sensor grid while others are present in the oil flow stream. These contaminants may include soot accumulations, ferrous and non-ferrous wear particles 194, water 196, and the like. In the illustration, the wear particles and water have settled to the bottom of the measurement chamber and rested on the sensor grid. Other contaminants which may also be detected include fuel, glycol (coolant), sodium, silicon, tin, lead, copper, iron, chromium and aluminum. Throughout this period of accumulation, the electromagnetic exciter 198 has not been charged. At the prescribed predetermined interval, the electromagnetic exciter will be alternately charged from positive charge to negative charge at an appropriate frequency as determined by the control logic illustrated and described in detail with reference to FIGS. 43 through 48.

The effective frequency response as influenced by the dielectric medium, the oil, and the sensor grid will then be communicated to the control logic for analysis in accordance with methods of the present invention as described below. At the same time, the alternating charge induced in the sensor grid will act to prevent the accumulation of wear particles and water molecules across the face of the sensor grid so as to allow a continuous stream of oil to flow through the measurement chamber and sweep the grid clean. After a period of time, given the specific construction of the sensor housing shown, if these accumulations should permanently collect on the sensor grid such that the oil flow is insufficient to clean the grid, this condition can be detected and the sensor grid replaced.

In other sensor housing constructions, discussed below in connection with FIGS. 31–35, the dynamics of oil flow through the measurement chamber are modified to provide alternative techniques in assuring against permanent accumulations of water, wear particles, or soot on the sensor grid.

In the previously described embodiments, the sensor design has included a single sensor housing and a single sensor grid excited by the control logic. This same basic technique can be utilized in combination with another grid-type sensor or a pair of grid-type sensors to provide a comparative technique for analyzing engine oil. Examples of oil analysis sensors for a comparative analysis strategy are shown in FIGS. 25–30. Those shown in FIGS. 27–29 include the use of a single additional sensor grid while those shown in FIGS. 25 and 30 include the use of a pair of additional sensors.

Figure 25:
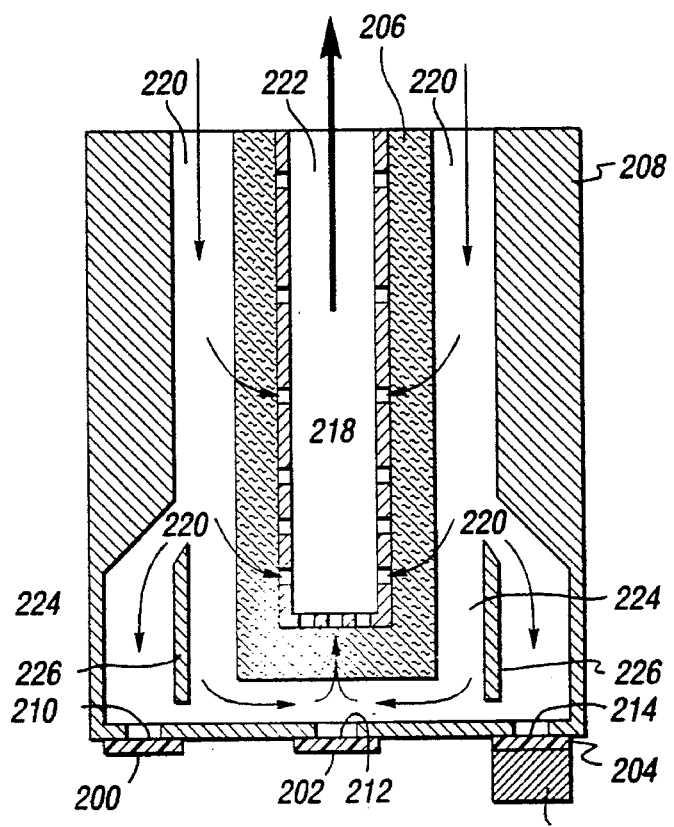
FIG. 25 shows a second embodiment of an oil analysis sensor, including a filter housing and a plurality of sensor grids utilized and located in different oil flow paths through the filter housing to provide a comparative method of engine oil analysis according to the present invention.

In FIG. 25 an example of a comparative oil quality sensor arrangement including three separate grid sensors 200, 202, and 204 of the type earlier described is shown. In this particular embodiment, the oil filter element 206 is cylindrical and is mounted within the housing 208. The cylindrical filter element 206 includes an inner perforated and hollow sleeve 218. This accommodates the continuous flow of oil through the filter housing in the direction of arrows 220 and then through the filter 206, perforated sleeve 218, and out in the direction of arrow 222. The housing disclosed includes three separate ports 210, 212, and 214 at its bottom end. In a manner as generally described earlier, three separate sensor grids 200, 202, and 204 are positioned with one sensor grid under each of the corresponding ports. This provides three separate chambers within the same enlarged flow chamber 224. The enlarged flow chamber 224 includes a pair of vertically oriented baffles or guide members 226 which effectively guide the flow of oil into three separate flow paths, one above each of the respective sensor grids. The guide members 226 are placed so as to produce substantially equal mass flow rates of oil over the outboard sensor grids 200 and 204, while providing a substantially different mass flow rate of oil passing over the center sensor grid 202. The oil flow characteristics can thus be tuned such that the contaminants will accumulate at varied rates. One of the outboard sensor grids may additionally be equipped with a permanent magnet 216 thereby providing means of distinguishing between ferrous and non-ferrous particles in the oil. Furthermore, the center sensor 202 may also be equipped with a permanent magnet to provide a comparison between the rate of change of the concentration of ferrous and non-ferrous particles in the oil.

As a design option, the sensor grids 200, 202, and 204 may be implemented as disposable sensor grids, permanently affixed to the bottom wall of the filter housing, with the filter housing itself being designed to be disposable. The construction of the sensor grid would be selected such that it would last slightly longer than the maximum anticipated oil drain for a particular application.

Figure 26:
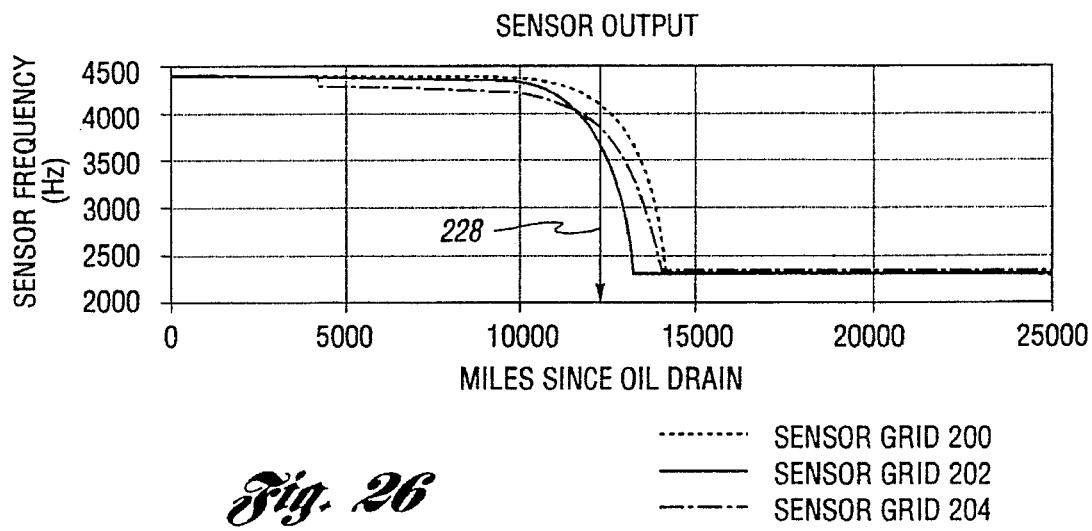
FIG. 26 is a plot showing a typical change in sensor frequency as a function of vehicle miles for an installed engine.

Referring now to FIG. 26, arrow 228 indicates an oil drain recommendation. All sensor grids are designed to reach a specific frequency once a shorted condition is established.

For example, for the sensors having a frequency characteristic as shown in FIG. 26, the frequency corresponding to a shorted condition is about 2300 cycles per second (Hz). It will be noted that the frequency responses of grids 200 and 204 begin to diverge at about 10,000 miles. This variation is generated through intentional flow and charging differences at the two sensor grids. Comparative measurements permit separation of soot effects from other contaminant and oil degradation influences. Also the start-up and shut-down measurements, similar to those described with reference to FIG. 15, permit quantifying water contamination effects.

In addition, by comparing signals from grids 200 and 204, cumulative wear and wear-rate trends may be estimated. It is expected that cumulative effects of trapped wear debris should create sufficiently large shifts in sensor frequency to satisfy the purposes described. It will be noted from FIG. 26 that a sudden decrease in frequency for sensor grid 204 occurred at approximately 4,000 miles. This indicates a one-time event which produced increased ferrous particle contaminants most likely produced by ferrous component wear. Subsequent trends in the response frequency of sensor grid 204 reflect continued wear throughout the oil drain period, but no additional notable events.

Figure 27:
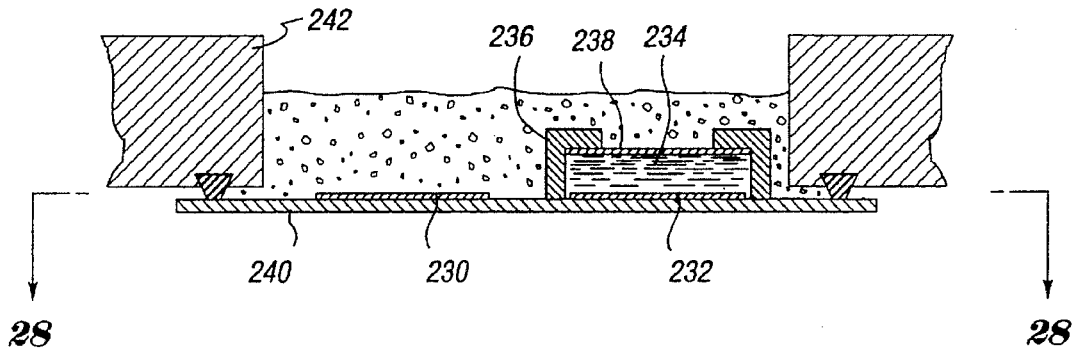
FIG. 27 is a partial elevational view, shown in section, of a third embodiment of the present invention utilizing dual sensor grids on a single substrate wherein one of the sensor grids is exposed to a reference sample.
Figure 28:
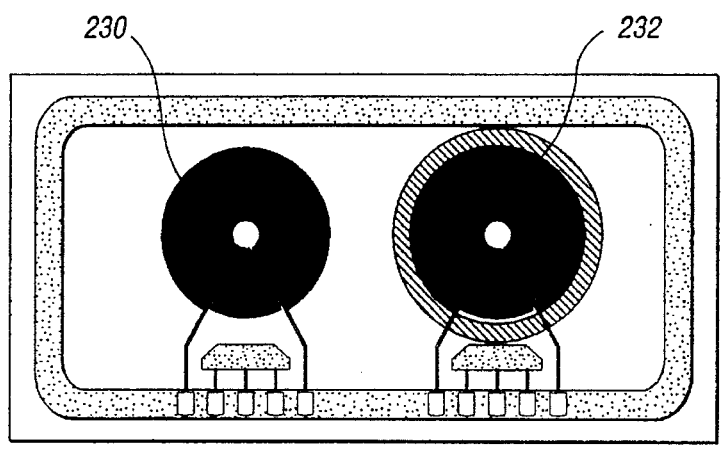
FIG. 28 is a plan view of the reference sensor design according to the present invention as shown in FIG. 27.

FIGS. 27 and 28 show another embodiment of a comparative-type oil quality sensor. This system provides an advantage over the system illustrated in FIGS. 18–21, in that one can account for temperature and pressure dependencies. A reference signal is provided by a second "reference" sensor grid 232, preferably located on the same substrate as the primary measurement grid 230. As shown, the reference sensor 232 houses a reference fluid 234 within an annular housing 236 which is isolated by a diaphragm 238. The diaphragm is preferably made of a flexible material to accommodate a pressure differential between the reference and sample fluids. Therefore, pressure sensitivity will be involved in the reference frequency response.

Ideally, the reference fluid would have substantially similar temperature characteristics as the test fluid and may be the same fluid as uncontaminated and undegraded sump fluid. Thus, the reference fluid or oil will display the same characteristic temperature dependance as the sample fluid. This particular analysis strategy assumes that the reference oil will remain stable over the maximum anticipated oil drain interval. In practice, the reference oil may degrade when exposed to high temperatures. Rather than providing for reloading of new reference oil with each oil change, one might also select a synthetic oil for use as a reference since synthetic oils are not nearly as susceptible to degradation when exposed to high temperature.

With continuing reference to FIGS. 27 and 28, the sensor grid plate 240 may be secured to the housing 242 in any of a number of manners such as the manner earlier described. All other construction characteristics of the grid assembly remain the same as earlier described.

As for the oil quality analysis methodology, the reference sensor 232 responds to the same temperature, pressure, and other extraneous environmental influences as the sample sensor 230. As measurement chamber conditions change, the response of the reference material and the reference measurement system (the sensor) will change accordingly. It can be assumed that the reference and sample sensors will respond similarly to environmental influences. The reference material must be a stable oil, e.g., the synthetic oil mentioned above, or some other material (not necessarily a liquid), housed within a control volume as provided by housing 236, and held in thermal equilibrium with the oil sample and sample sensor. The ratio of the sample sensor frequency to the reference tensor frequency will eliminate the effect of unwanted environmental influences, regardless of their complexity. This methodology permits the elimination of the thermistor and non-linear compensation logic used to improve the accuracy of the single sensor design shown in FIGS. 18–21.

Figure 29:
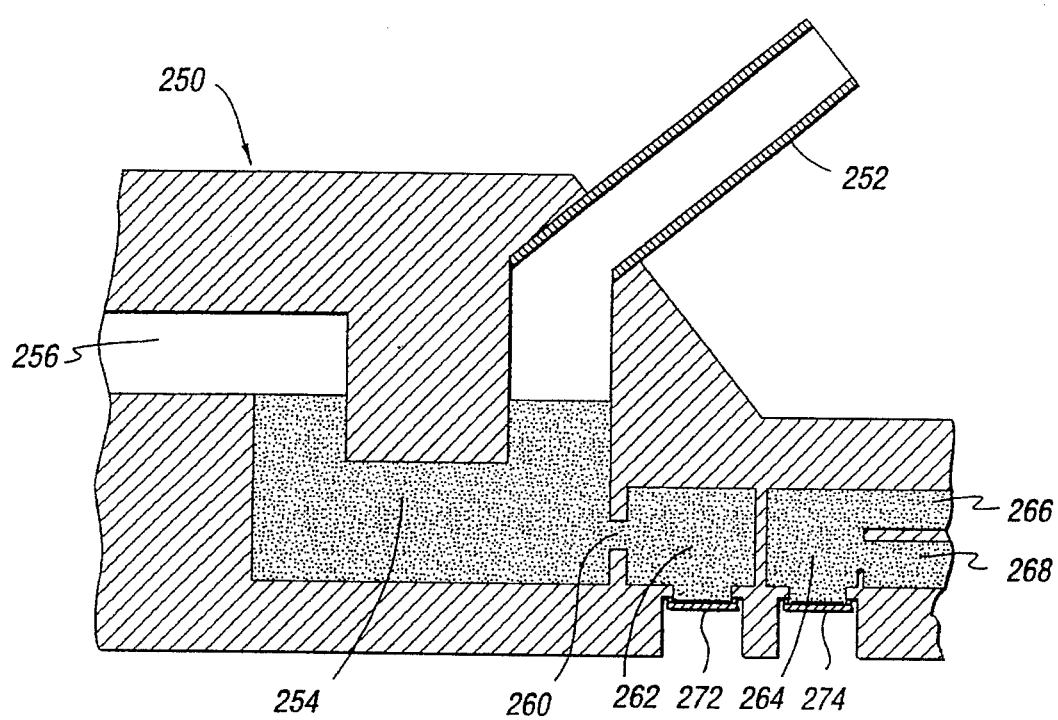
FIG. 29 is a fourth embodiment of the present invention showing yet another form of a reference sensor design utilizing dual sensor grids and a sample of unused oil for a baseline reference.

A further example of a dual sensor comparative-type oil quality sensing system is shown in FIG. 29. As shown, a housing, generally designated 250, is provided to be attached to the engine block in any suitable manner. Fluid communication is provided from an oil filler neck 252, through a collection elbow 254, and then through a passage 256, leading to an oil sump. A port 260 at the base of the collection elbow 254 communicates with an oil sample examination chamber 262. The height of examination chamber 262 is less than the height of the collection elbow 254, i.e. below passage 256. At the base of the examination chamber 262 is a sensor grid 272 of the type earlier described. Within the same housing 250 adjacent to examination chamber 262, is a second examination chamber 264 and sensor grid 274, similar to that described in reference to FIGS. 18–21, for example. In other words, in the second examination chamber 264, service engine oil is being constantly circulated from an inlet 266, across the sensor grid, through outlet passage 268, and through a conventional filter arrangement as earlier described, i.e., oil filter 94. Utilizing this methodology the collection elbow 254 collects new oil from the oil filler neck 252. The collected sample serves as the reference oil while the design of the collection elbow allows retaining an oil mixture which compensates for unlike make-up oil additions.

Figure 30:
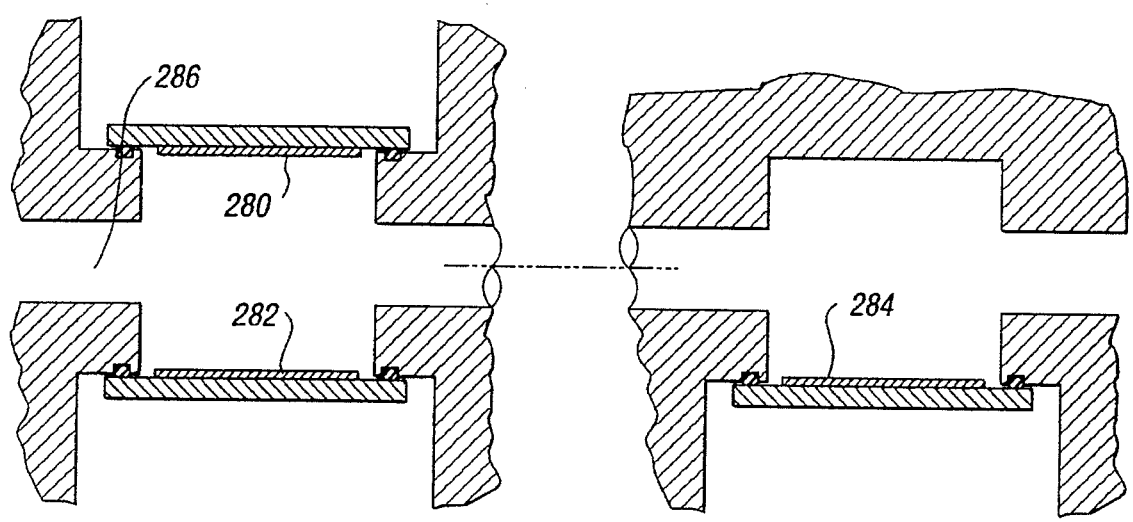
FIG. 30 is a fifth embodiment of the present invention showing another form of reference sensor design with improved contaminant detection including three sensor grids wherein sensor grids 280 and 282 are placed in a common measurement or analysis chamber at the top and bottom, respectively, at a point where the oil is upstream of the oil filter, thereby representing the unfiltered oil, and a third sensor grid 284 is placed in a separate analysis chamber downstream of an oil filter.

In another arrangement, as shown in FIG. 30, increased contaminant sensitivity is realized during engine shut-down analysis. This design utilizes three sensor grids 280, 282, and 284. Sensor grids 280 and 282 are located in an unfiltered oil passage 286, while sensor 284 is located in filtered oil. Sensor grid 280 is inverted above sensor grid 282. Presumably, smaller wear particles will remain in suspension longer than the larger ones and will be detected by sensor grid 280. As suspended and emulsified contaminants begin to precipitate out of the oil sample, sensor grid 282 will measure contaminant accumulations. Smaller particles will be detected by sensor grid 280, even after larger particles have fallen to sensor grid 282. The capacitance detected by sensor grid 280 will increase due to the partially charged particles which act as additional capacitor plates. However, particle migration toward sensor grid 282 will ultimately affect the frequency response of sensor grid 280 as well. Ultimately, a complimentary effect may be observed at sensor grid 282 as charged particles sink through the oil.

The time delay between grid responses may be quantified for use in various sensor measurement analysis algorithms. Comparing measurements from both sensor grids 280 and 282 provides unique oil-borne contaminant information. Viscosity influences may also be observed through this strategy. As oil viscosity increases, lead-time delay between the two grid responses will increase. Sensor grid 284 provides a reference signal since it is subjected to filtered (contaminant free) oil. Comparisons of sensor grid 284 measurements with measurements from sensor grids 280 and 282 will separate contaminant effects from gross oil degradation.

Figure 31:
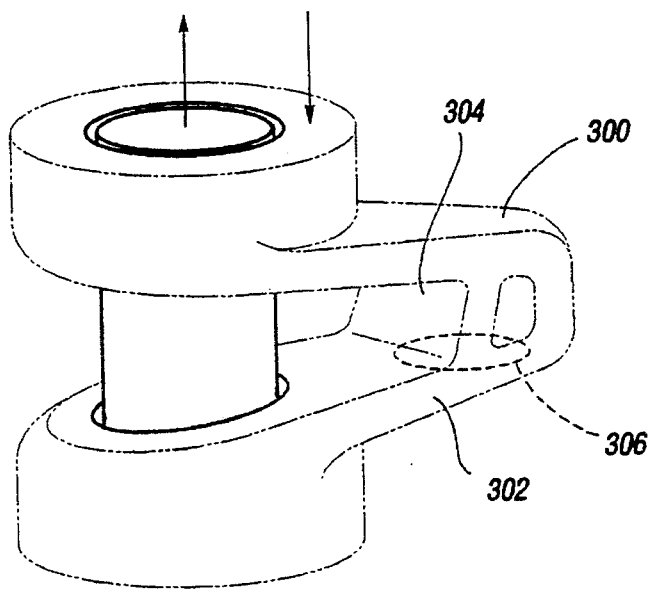
FIG. 31 is a perspective view representation in solid form, such as used for a molding core, illustrating oil flow chambers of the sensor housing shown in FIG. 18 including a static jump channel.

FIG. 31 is a perspective view of a representation in solid form of the oil flow chambers of the sensor housing shown in FIG. 18. It is a general representation of the molding core which would be required to cast the oil flow chambers within the housing. Thus, there is shown in solid form the inlet passage 300, outlet passage 302, generally vertically oriented examination chamber 304, and as a dotted line the housing bore 306 accommodating the oil sensor and grid assembly. During normal operation, the circulating oil flows by examination chamber 304 and across the surface of the sensor grid. When flow decreases sufficiently or stops, the examination chamber 304 acts as a "static jump" which provides an additional volume of oil which descends directly upon the sensor grid to increase measurement sensitivity (as opposed to flowing across the sensor face which may wash any contaminants away).

Figure 32:
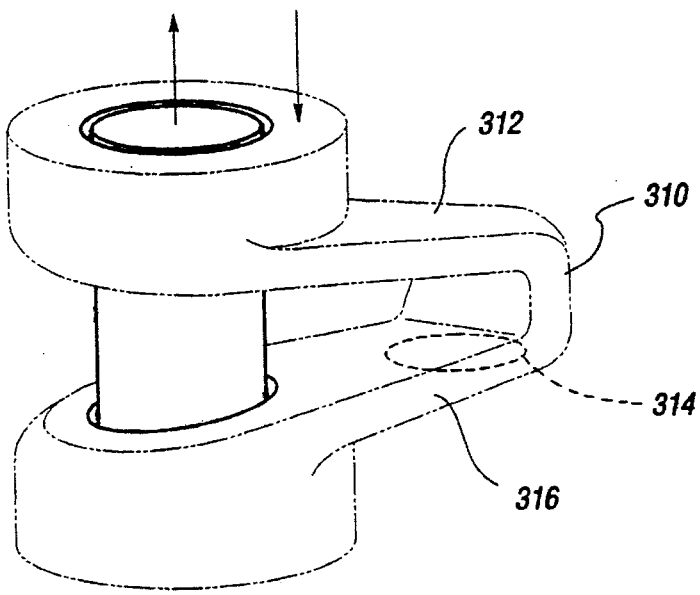
FIG. 32 is a view similar to FIG. 31 showing another embodiment of the sensor housing of the present invention without a vertically oriented static jump channel.

FIG. 32 is a view similar to that of FIG. 31 but showing an alternative embodiment for the housing design without a chamber for providing a static jump. Consequently, the examination chamber 310 is one in which there is a continual flow of fluid from the inlet 312, through the examination chamber 310 across the sensor grid located within the bore 314, and out through the outlet passage 316. Preferably, the oil flow chambers of FIGS. 31 and 32 are designed to produce a substantially laminar flow of oil.

Figure 34:
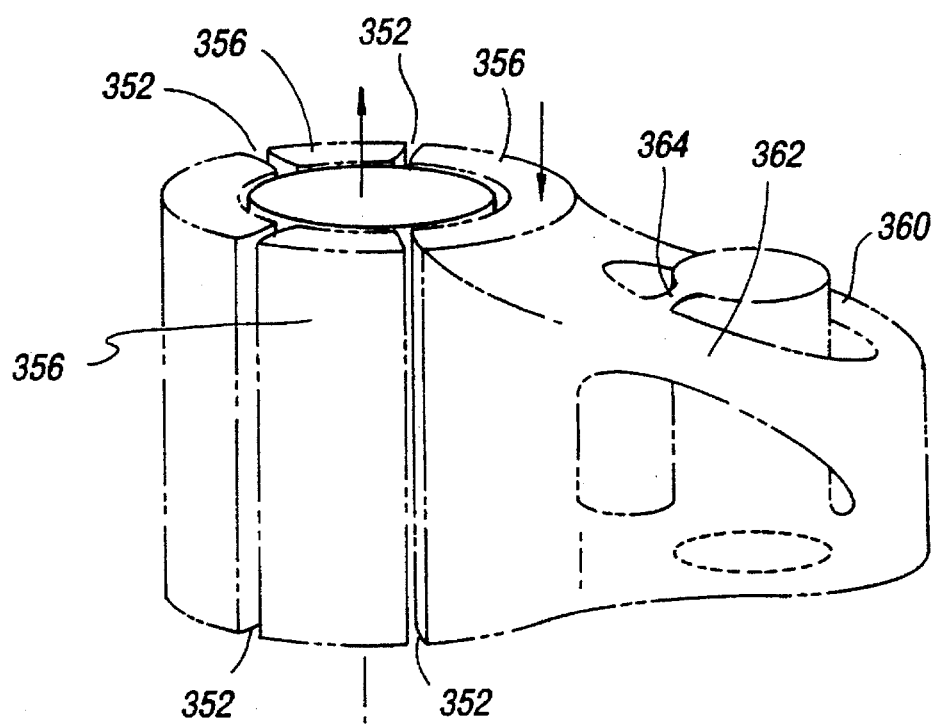
FIG. 34 is a perspective view similar to FIG. 31 illustrating another embodiment of the present invention directed toward a single grid continuous flow oil analyzer, wherein the filter housing is compartmentalized by providing vertically directed vanes within the housing, and oil is delivered to the grid sensor along two separate paths sweeping around a vertically extended examination chamber.
Figure 33:
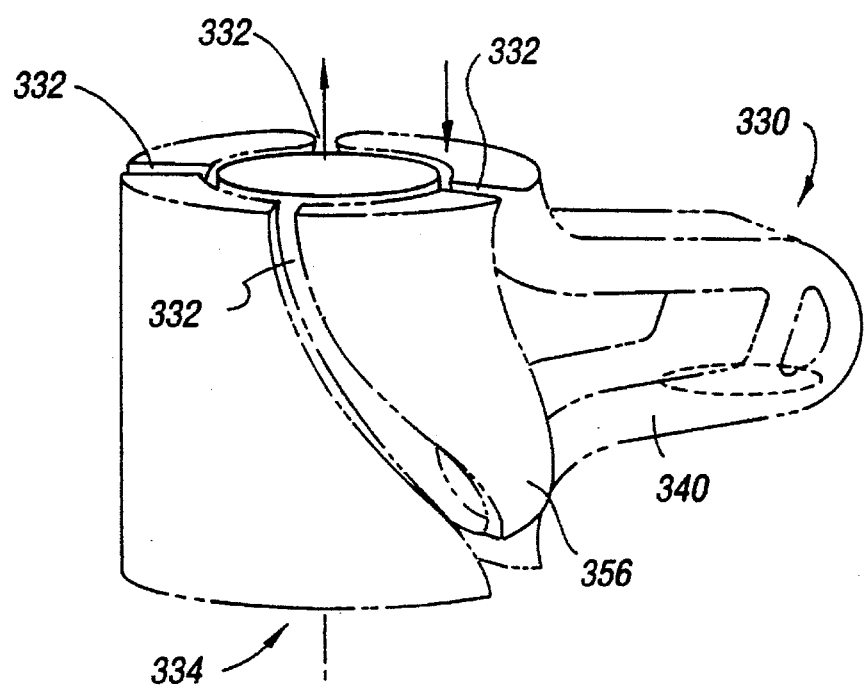
FIG. 33 is a perspective view similar to FIG. 31 illustrating another embodiment of the present invention directed toward a single sensor grid design having an examination chamber as shown in FIG. 31, wherein flow across the sensor grid is promoted by a venturi design in the oil flow passages of the filter housing.

FIGS. 33 and 34 depict additional embodiments of a housing core mold design, and consequently a different embodiment of the sensor housing 330. In FIG. 33, the housing is seen to include a plurality of appropriately oriented vanes as indicated at 332 to produce a venturi flow pattern. This divides the main oil flow chamber, generally designated 334, into a plurality of separate compartments, with the flow compartment 336 communicating with the outward passage 340. As a result, the oil flow rate at the outward passage is increased which results in an increased overall pressure drop of fluid flowing across the sensor grid. This in turn increases the flow and facilitates cleansing of debris from the sensor grid.

In FIG. 34, the core mold is seen to provide a plurality of vertically directed vanes 352 dividing the housing into a plurality of flow compartments 356. Departing from earlier designs, an inlet passage to the sensor grid is split into parallel paths 360 and 362 which join near the sensor grid. This produces a vertical column of oil above the sensor grid which has a substantially lower flow rate than that of the flow compartments 356. However, a small orifice 364 is provided near the top of the column to assure some oil circulation. The vertical column of oil functions as an enlarged examination chamber to allow more contaminants to accumulate on the sensor grid so as to increase measurement sensitivity.

Figure 35:
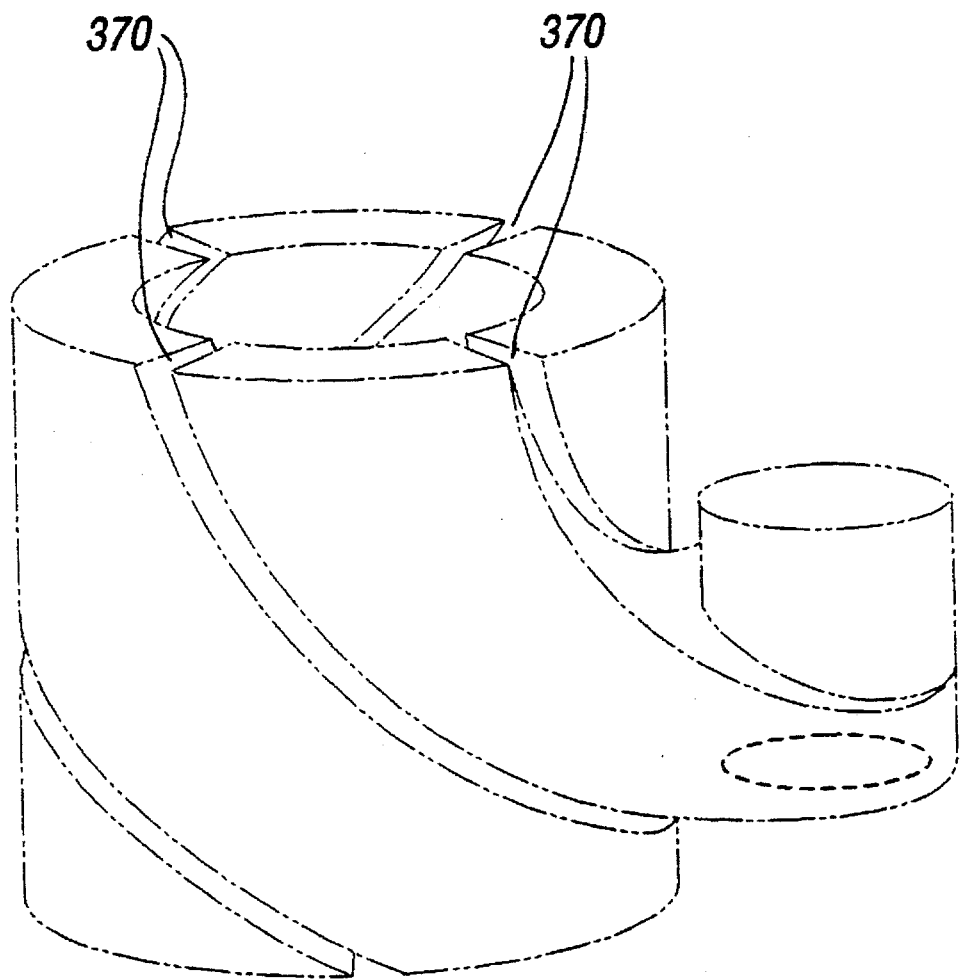
FIG. 35 is a perspective view similar to FIG. 31 illustrating another embodiment of the present invention utilizing helical flow vanes to direct oil flow over the sensor grid.

FIG. 35 illustrates yet another alternative embodiment for a core mold similar to those illustrated in FIGS. 31 to 34, but having a plurality of helical vanes 370 to direct oil flow. Of course, depending upon the particular application, various combinations of the flow patterns illustrated in FIGS. 31–35 may be utilized.

Figure 36:
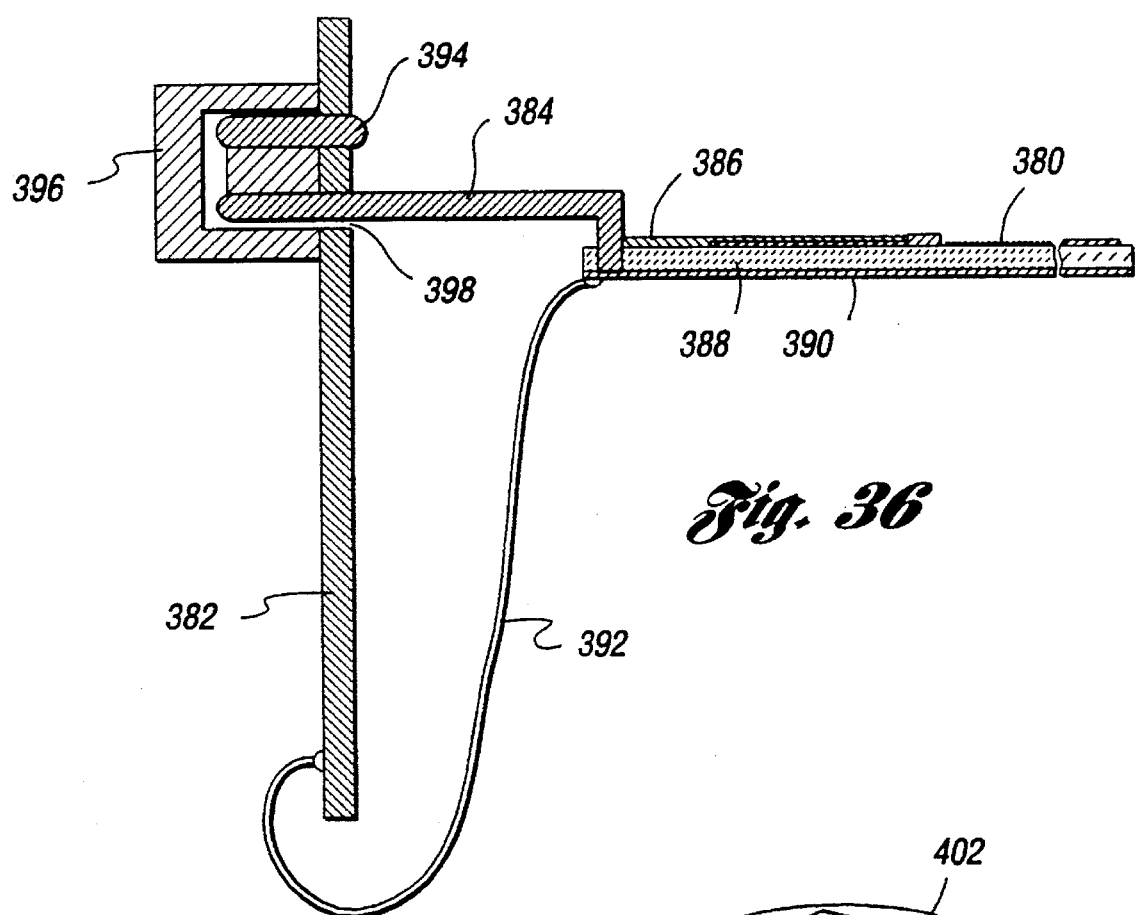
FIG. 36 is a partial cross-section, elevational view illustrating a manner of attaching a sensor grid to a circuit board in accordance with the present invention.

In accordance with another aspect of the present invention, a method of attaching a sensor grid 380 to a circuit board 382 is provided as shown in FIG. 36. A sensor grid, as shown in FIG. 22 for example, is provided with a plurality of rigid connection pins 384 each of which is conductively connected to a corresponding contact pad 386 and passes through ceramic substrate 388 and is bonded thereto. The ceramic substrate 388 is further bonded to a board such as a fiberglass laminate with a conductive metallic layer 390, which serves as a lower ground plane. A tether 392 is attached to the lower ground plane at one end and to the circuit board 382 at its other end. The circuit board further includes a board mounted pin 394 for each of the respective rigid connection pins 384. A rigid connector (jumper) is provided to slip over the board mounted pins 394 and sensor connection pins 384 to provide an electrical connection between the two when the sensor grid pin is inserted through hole 398 in the circuit board.

Figure 37:
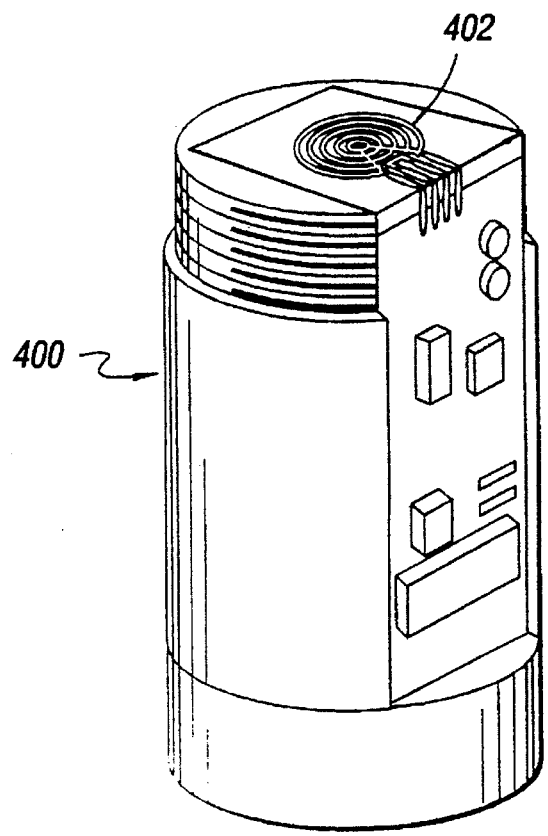
FIG. 37 is a perspective view showing an integral electromagnetic sensor grid and circuit board option in accordance with the present invention.

As shown in FIG. 37, an electromagnet, sensor grid, and sensor board/card can be provided as a single integrated component 400. Thus, referring to FIG. 20, the same mounting flange 169, used to hold the electromagnet in place within the housing, can be utilized to hold the entire integrated assembly 400 to the housing, so as to eliminate the side-mounted sensor board 174, sensor grid 166 and cover 176.

Figure 38:
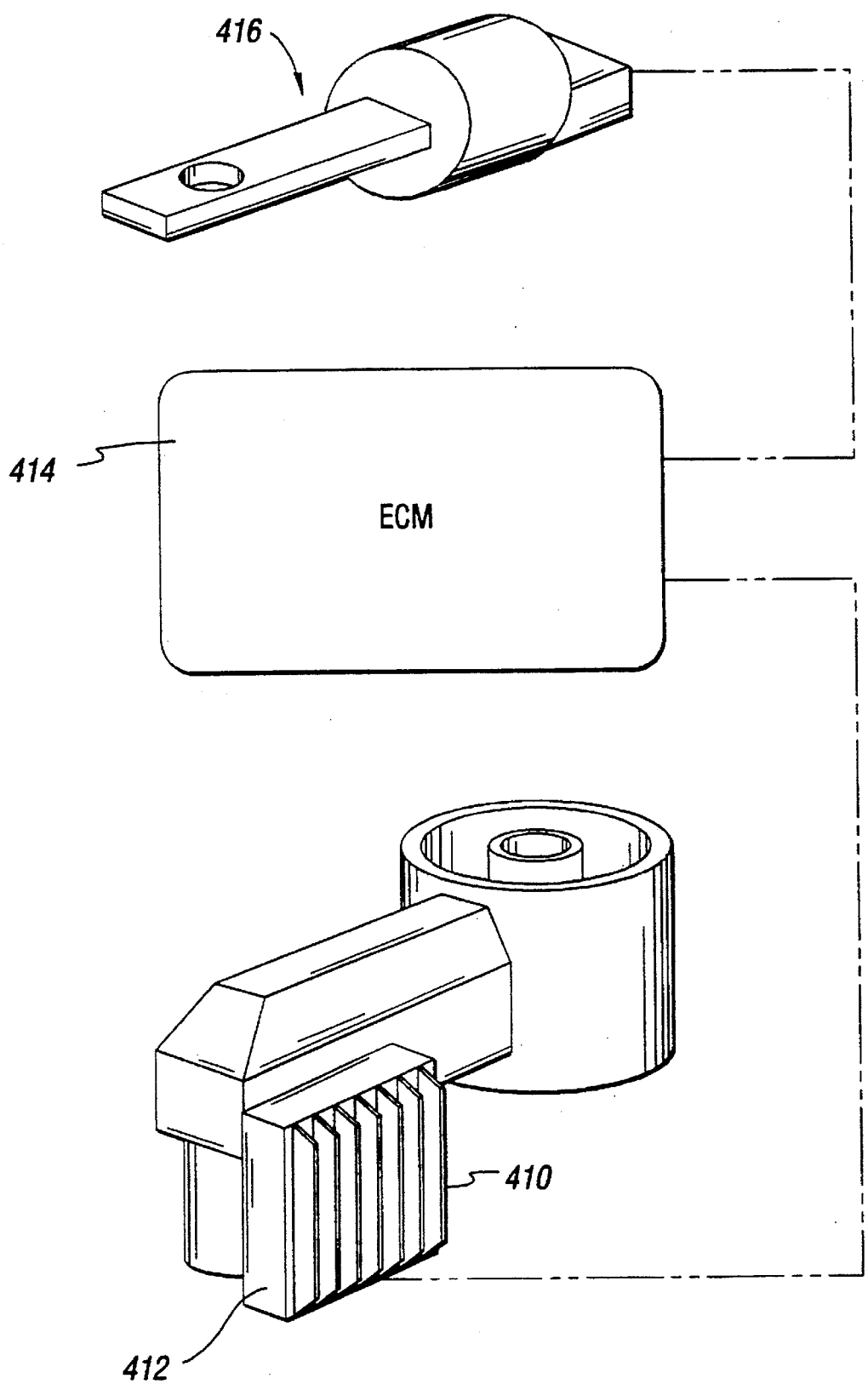
FIG. 38 is a tenth embodiment of the present invention showing an oil quality sensor including cooling fins used in combination with a viscosity sensor in accordance with the present invention.

In FIG. 38 is shown another alternative embodiment of the present invention, wherein the sensor housing as represented in FIGS. 18–21 is equipped with a series of cooling fins 410 made integral with the circuit board cover 412. These act to dissipate heat generated from the oil being circulated through the sensor. This reduces the likelihood of higher temperatures adversely affecting the performance of the circuit board components, including the control logic which is implemented using a microprocessor in a preferred embodiment. As shown, the sensor control logic is operationally connected to the control logic of the electronic control module 414. Also in communication with the electronic control module is a separate viscosity sensor 416. The components illustrated in FIG. 38 are similar to those described with reference to FIG. 17.

Consistent with the present invention, the oil sensor housing need not be interposed between the engine block and oil filters. Other options are available as shown in FIGS. 39 and 40.

Figure 39:
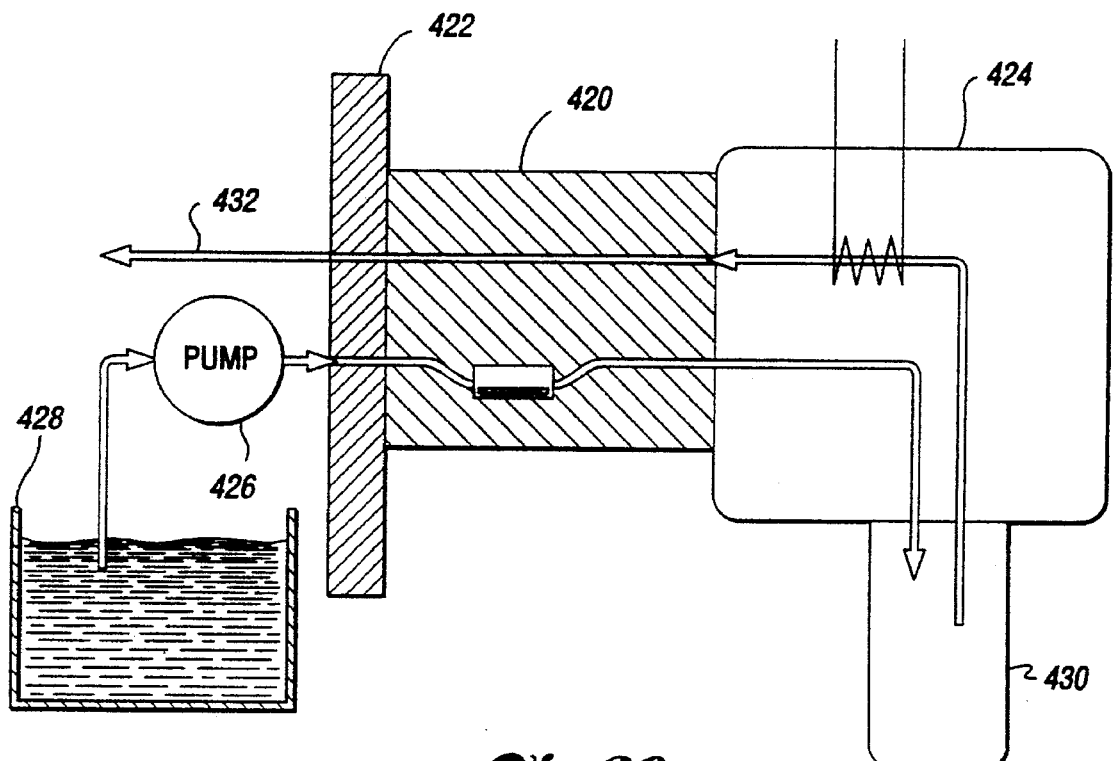
FIG. 39 illustrates another embodiment of the present invention wherein the sensor housing is interposed between the engine and oil cooler.
Figure 40:
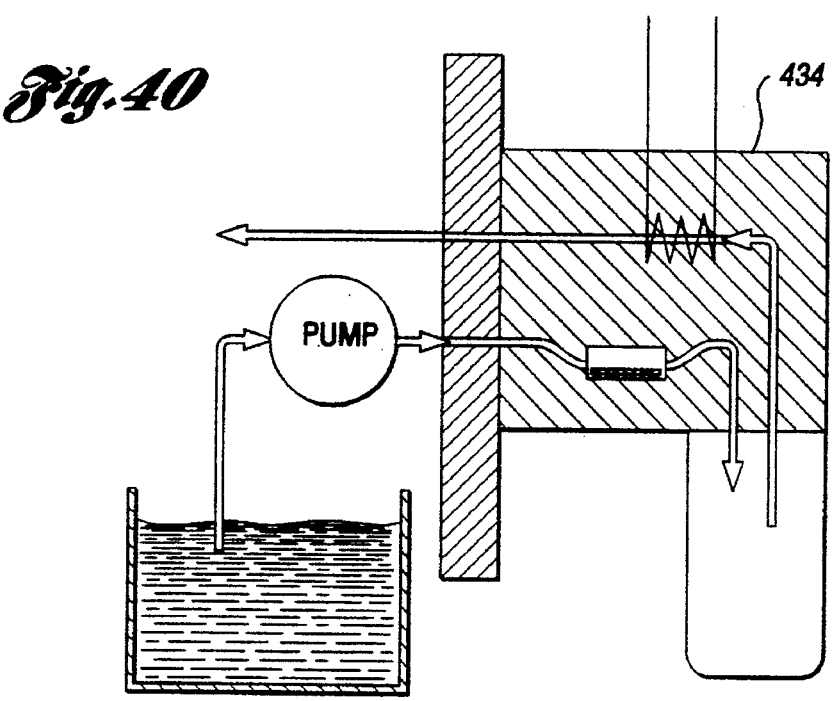
FIG. 40 illustrates another embodiment of the present invention wherein the sensor housing is integrated with the oil cooler.

For example, as depicted in FIG. 39, the oil sensor housing 420 may be interposed between the engine block 422 and the oil cooler 424. Similar to the previous embodiments, unfiltered oil is circulated past the oil sensor coming from the pump 426 and delivering oil from the oil pan or sump 428. The unfiltered oil, after it passes through the sensor, is then circulated to a conventional oil cooler 424 and through an oil filter 430 which may be integral to the oil cooler assembly. The filtered oil is then passed through a heat exchanger portion of the oil cooler, and then through line 432 to the engine block. As shown in FIG. 40, the sensor housing and oil cooler can be integrated into a single housing 434 if desired.

Figure 41:
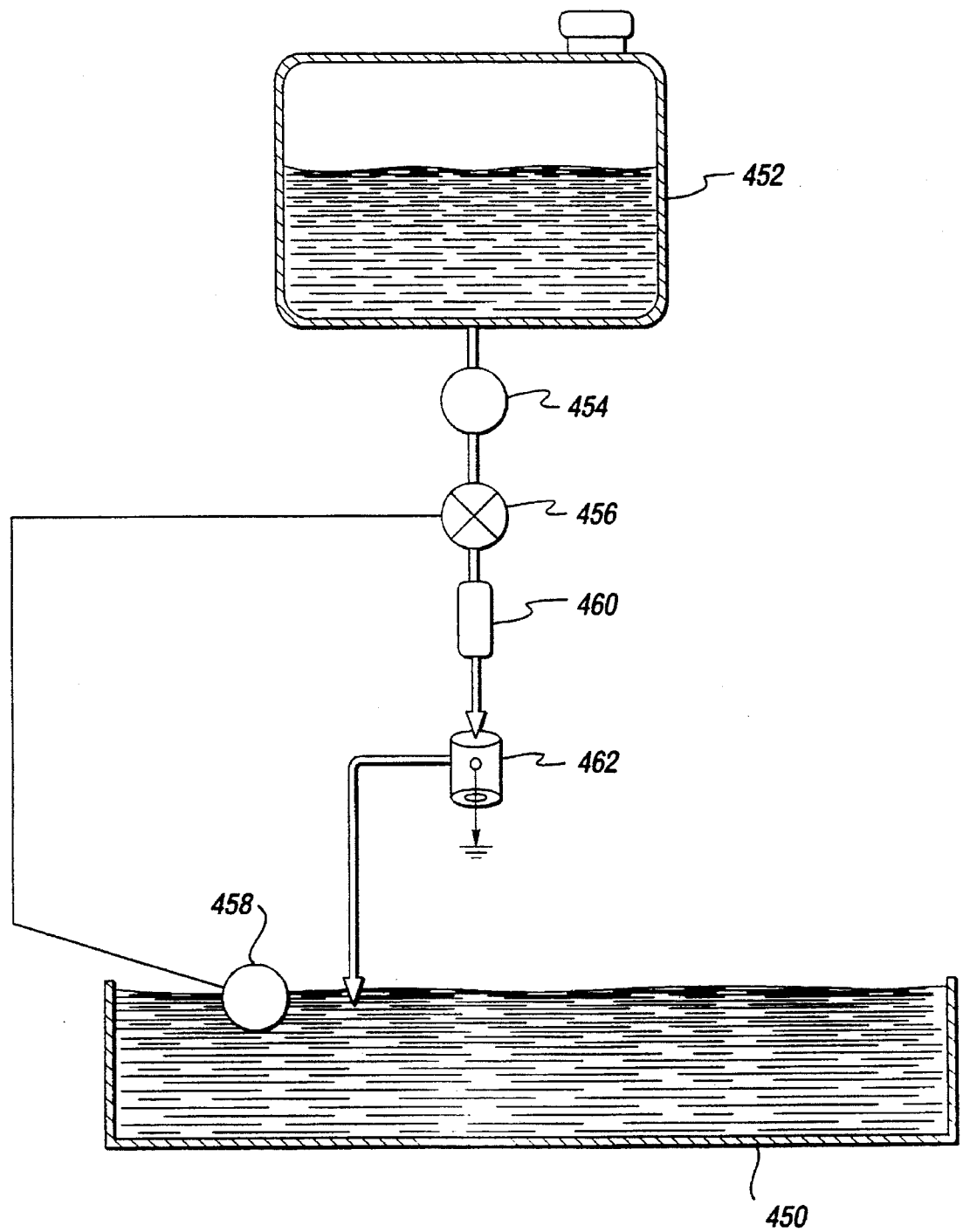
FIG. 41 is a schematic representation of a system for establishing a baseline calibration curve correction to account for unlike make-up oil additions in accordance with the present invention.

In FIG. 41 there is shown a method or system of calibrating a baseline curve to correct for addition of a dissimilar make-up oil. In other words, the baseline curve calibration accounts for oil which is of a different quality, brand, viscosity, or the like being added to the sump 450. The system includes a make-up oil reservoir 452 which is in fluid communication with an oil filter 454. Of course, the oil filter 454 is optional. From the oil filter, the make-up oil is fed to a normally-closed control valve 456 which is actuated to an open position based upon a signal from a float or similar sensor 458. Control valve 456 will open whenever the sump oil level drops below a predetermined level. Thus, when the control valve is opened, make-up oil flows from the reservoir 452 through a flow meter 460 and then to the oil quality sensor 462. Preferably, oil quality sensor 462 is provided in addition to any other oil sensor within the lubrication system. The function of oil quality sensor 462 is to determine the quality and/or type of the make-up oil being added from the reservoir and to provide this information to the control logic. This allows the control logic to update the baseline calibration curve and subsequent computations made to indicate the optimum oil drain interval.

Figure 42:
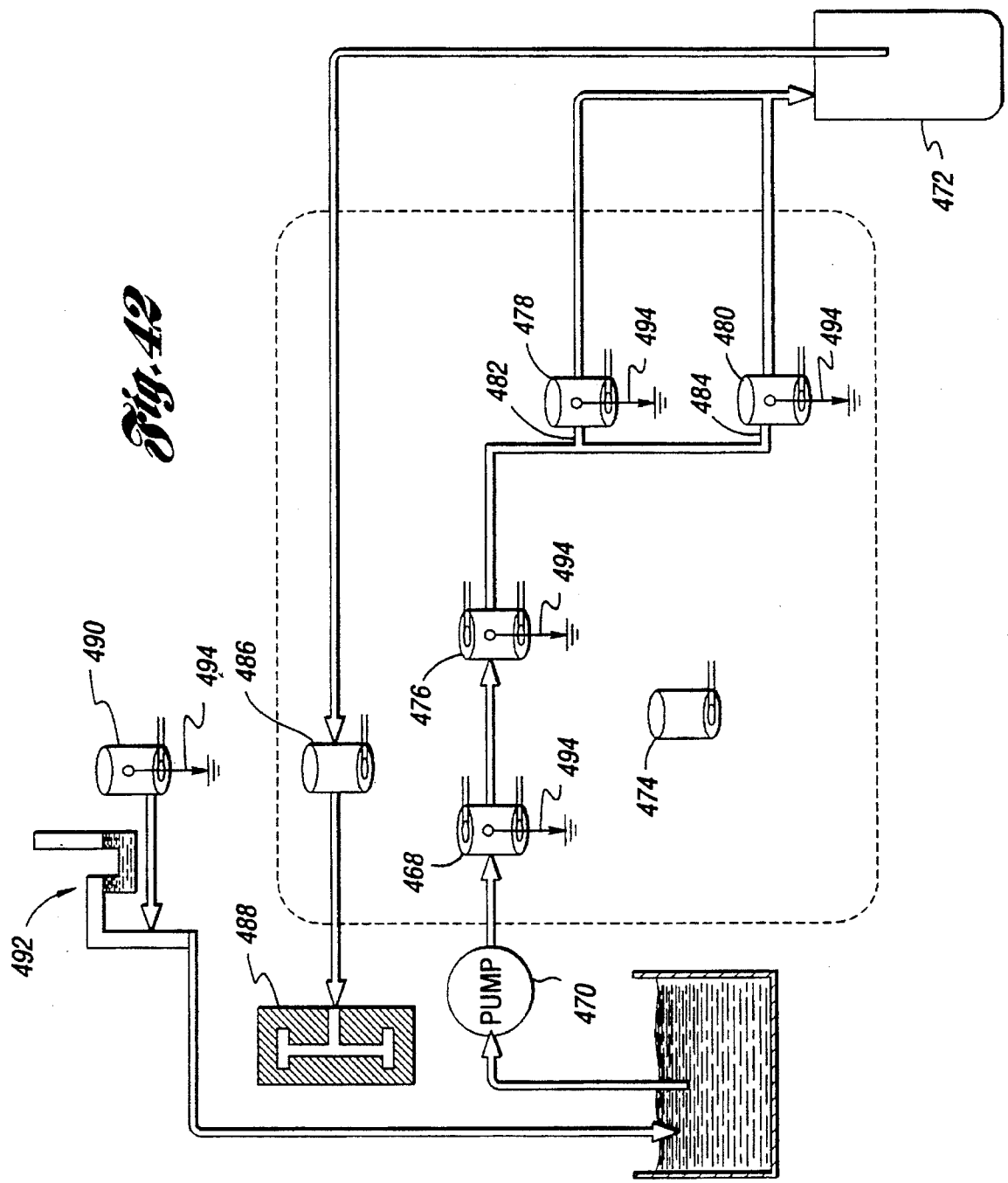
FIG. 42 schematically shows oil quality sensor mounting options for various embodiments in accordance with the present invention.

The aforementioned design alternatives as discussed in connection with FIGS. 18–41 are represented schematically in FIG. 42 representing the various mounting options. Identified as chamber 468 is an oil quality sensor as generally shown in FIG. 30 utilizing a dual sensor arrangement, positioned one above the other, to measure the gravity effect on contaminants within the oil. Used alone (i.e. neglecting the other depictions of sensor placement), it would process the unfiltered oil from pump 470 analyzing it prior to passing through oil filter 472 in the manner as previously described above in detail. Identified as chamber 474 is an optional reference sensor having an appropriate reference fluid in it for purposes of making a comparison between the reference fluid and the unfiltered oil passing through chamber 468. This general arrangement is described above with reference to FIG. 27 wherein, chamber 474 corresponds to reference chamber, fluid, and sensor 232–238.

With continuing reference to FIG. 42, the sensor may be provided with two sensor grids, one above the other, in the manner as suggested in connection with the embodiment shown in FIG. 30. Also, the sensor may be equipped with a permanent magnet to allow differentiation between ferrous and non-ferrous magnetic contaminants present within the oil, as described above in connection with the embodiment shown in FIG. 25. As shown at chambers 478 and 480 of FIG. 42, the unfiltered oil may be divided along split oil flow paths 482 and 484. The flow paths have associated mass flow rates $M_2$ and $M_3$ to provide for examination of the effect of different flow rates of unfiltered oil passing over a plurality of sensors as discussed in connection with the embodiment shown in FIG. 25. Further, as indicated at chamber 486, a reference sensor may be provided on the filtered oil side of the oil filter 472 as suggested in connection with the embodiment of FIG. 30. Finally, as shown at chamber 490, the oil quality sensor grid may be provided at the elbow of an oil fill neck 492 so that the effect of make-up oil being added to the sump oil can be taken into consideration by the control logic when analyzing the oil quality, as explained above in connection with the embodiment in FIG. 29.

The sensor locations indicated as being bounded by a housing, generally designated 494, can be provided within the oil cooler housing as described in connection with FIG. 40. Alternatively, the sensor may be disposed within an intermediate housing to be placed between the engine block and oil filter, as discussed in connection with the embodiment of FIGS. 18–22, or positioned between the engine block and the oil cooler as discussed in connection with the embodiment of FIG. 38.

Referring now to FIGS. 43 through 51 collectively, one method for performing oil quality analysis is illustrated which is preferably implemented by control logic, such as control logic 52 of FIG. 1, or ECM 104, data hub 110, or OQS 120 of FIG. 17. As illustrated in FIG. 15, a typical machine such as a heavy-duty diesel engine will have characteristic oil quality measurements depending upon the particular point during its operating and quiescent cycle. Thus, it is desirable to take a number of measurements during each portion of the cycle, i.e. during start-up, running, and shut-down.

In a preferred embodiment, the analysis strategies during the various phases of operation are predicated upon use of a Remaining Oil Life Estimator (ROLE) calculation. The ROLE is indicative of relative oil life. A maximum ROLE value may be arbitrarily constrained to a predetermined value, such as 100, which represents the best available lubricating oil (a synthetic oil for example) immediately following an oil change with the engine being operated under ideal conditions. Negative ROLE values indicate a violation of the recommended oil drain interval. Such a violation may be stored for future retrieval by service personnel. In addition, the vehicle operator may be alerted by an instrument panel light, or the like.

The ROLE is utilized to indicate the recommended oil change interval. Thus, an oil drain may be indicated when the ROLE reaches a predetermined value, such as 10. Preferably, however, the ROLE value indicative of a recommended oil change is modified during operation based upon the rate of oil deterioration. Of course, other strategies are also possible without departing from the spirit or scope of the present invention.

In a diesel engine application, a start-up analysis is preferably initiated upon engine ignition. Continuous measurements are performed during engine warm-up to compute the ROLE based on a number of parameters, such as engine hours, vehicle miles, and time elapsed since a previous ROLE calculation. The length of a shutdown period is relevant to start-up oil quality sensor measurements and grid fouling and flushing analyses since longer shutdown periods permit more debris to accumulate on the sensor grid.

Upon start-up, the oil quality sensor (OQS) must determine if an oil drain was performed during the shutdown period. Service personnel may indicate an oil change to the system resulting in a flag being set and transmitted to the sensor. However, this information can be incorrect or accidentally omitted. Therefore, the control logic will automatically detect an oil change to confirm this signal before replacing the previous baseline calibration. An oil change is indicated by a number of oil quality parameters which exhibit dramatic improvements when new oil replaces the degraded oil. With appropriate temperature compensation as provided by the present invention, capacitance based measurements are reasonable indicators of oil replacement. However, confidence in an oil change detection may be increased by detecting changes in viscosity and contaminant levels as well. Of course, a number of other measurements are also possible to increase the confidence of an oil change indication.

To reduce the possibility of increased component wear or damage resulting from an inaccurate ROLE determination, a predetermined safety limit may be imposed based upon the particular application and anticipated operating conditions. For example, a safety limit of 30,000 miles or 1,500 engine hours may be established so that an oil change is indicated when the safety limit is reached regardless of the current ROLE determination. Similarly, default drain intervals may be imposed based upon the type of lubricating oil employed. For example, most synthetic oils can operate safely over longer drain intervals than most mineral oils provided effective filtration is maintained. Preferably, therefore, a synthetic oil will be assigned a longer default drain interval than a mineral oil to reduce unnecessary oil changes. This default interval corresponds to a higher initial ROLE value. With the additional measurements provided by an oil quality analysis system according to the present invention, the default or safety drain intervals can be extended far beyond those currently recommended.

Thus, during the initial start-up period, the type of oil can be inferred based on a characteristic frequency response as a function of temperature. Change in viscosity as a function of temperature may be utilized to help confirm a particular oil type as well. Once the oil type is identified, an appropriate ROLE may be initialized. This value may then be modified by a user selectable safety factor. For example, a customer selected safety factor of ten would operate to decrease the initial ROLE value by ten percent so that an oil drain would be indicated earlier than the default value for the particular type of oil which is detected.

As previously described, it is also desirable to obtain data during normal engine operation using the oil quality sensor and an optional viscosity sensor. The electromagnets of the embodiments previously described may be energized to attract additional ferrous wear debris and polar molecules during engine operation while being periodically reversed to promote cleaning of the sensor grid. Measurements obtained during the cleaning process may be used to confirm previously measured ferrous debris concentrations. Differences in ferrous debris accumulation rates as a function of engine speed (and therefore oil flow rates) may be used to provide information relative to contaminant particle size.

A number of objectives are accomplished by collecting data during engine operation. Intermittent energization of the sensor electromagnets may be used to measure charge/discharge frequencies to indicate the dielectric value of the oil. Running measurements provide indications of oxidation/nitration, oil type, water content, soot, and other non-metallic contaminants as well. During engine operation, measurement data is collected by the control logic if a predetermined time interval has elapsed without an engine shut-down event. As explained in greater detail below, data may be used to measure dielectric slopes and perform trend analysis, detection of sudden changes resulting from adverse cycle conditions, and detection of viscosity trends for comparison with soot levels to increase confidence in the measurement. Data collected during engine operation also provides an indication of flushing/cleaning efficiency and sensor grid fouling. Preferably, engine speed, oil viscosity, and oil temperature information are gathered in preparation for this type of analysis.

In a preferred embodiment of the present invention, an engine shut-down analysis is performed each time the engine is shut-down. Power is maintained to the sensor for a predetermined period after engine shut-down, preferably up to ten minutes. Also preferably, a static column of oil is maintained over the sensor grid during this period to allow oil-borne debris to settle on the sensor grid. Time-dependent sensor frequency trends may be examined to identify the quantity and character of contaminants. As previously described, magnetic field flux patterns may be manipulated to orient ferrous debris for improved detection sensitivity. Since the oil temperature decreases during a shutdown measurement, a grid mounted thermistor provides an indication of the current oil temperature which is used to compensate the sensor frequency response for accurate comparisons across the temperature range of interest.

Since oil viscosity affects the rate at which contaminants settle on the sensor grid, significant viscosity shifts over the previous running cycle (after temperature compensation) must be considered when analyzing shutdown data. For example, for an extended operating period prior to engine shut-down which induced heavy soot accumulations, the oil viscosity would increase dramatically (over the entire temperature range). Therefore, contaminant settling time will be extended during the shut-down analysis. If viscosity information is not considered, a relative reduction in contaminants would be detected during the shut-down analysis. Conversely, fuel dilution could reduce oil viscosity and decrease settling times for contaminants. Either condition could trigger erroneous oil change indications or inappropriately extend recommended oil drain intervals. Shutdown measurements over an extended period can also provide indications of viscosity effects.

Figure 43A:
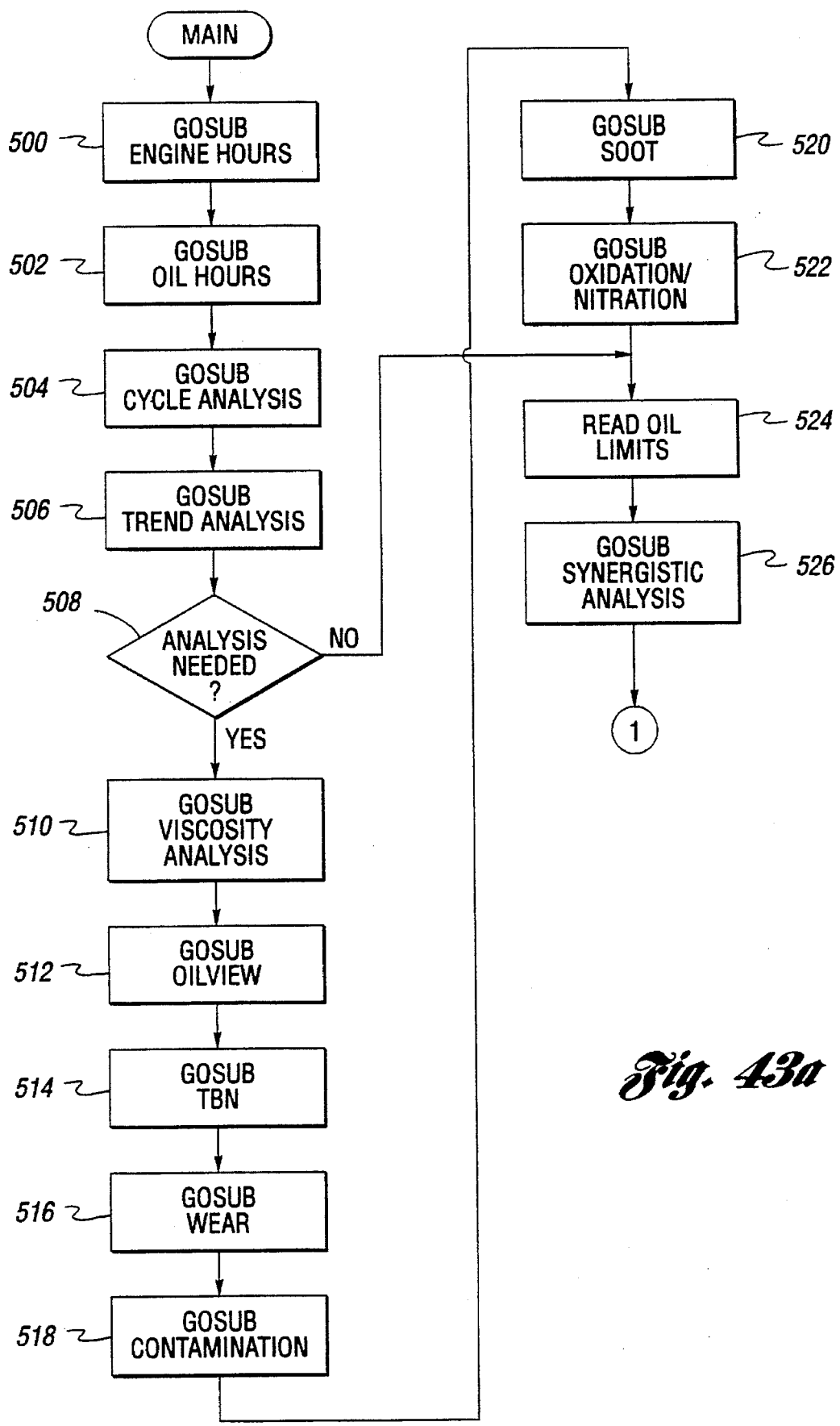
FIGS. 43–48 illustrate methods for analyzing oil quality which may be effected with various implementations of control logic for performing continuous engine oil analysis in accordance with the present invention.
Figure 43B:
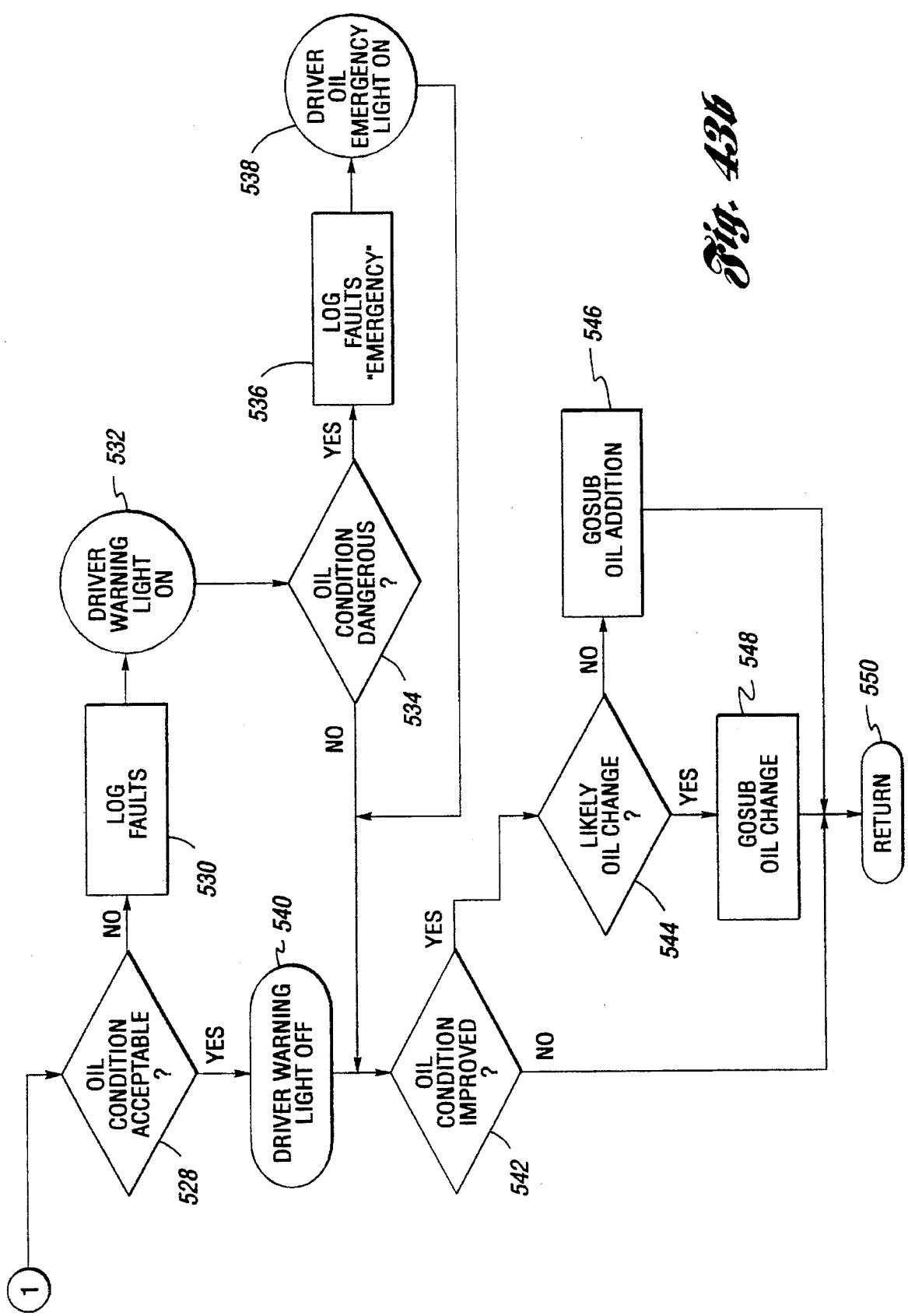

Referring now to FIGS. 43*a* and 43*b*, a flow chart is shown illustrating one method of the present invention for performing basic continuous oil quality analysis in an engine lubrication system. It should be recognized that this flowchart and the flowcharts illustrated in FIGS. 43 through 48 depict sequential processing of the method steps although any of a number of processing strategies could be utilized without departing from the spirit or scope of the present invention. For example, if the control logic is implemented in hardware, many of the method steps may be performed simultaneously or nearly simultaneously. Similarly, an interrupt driven processing strategy could also be utilized to achieve the objects and advantages of the present invention. A parallel processing technique employing a neural network or an adaptive processing strategy utilizing fuzzy logic could also be utilized to implement the method of the present invention.

Steps 500, 502, and 504 of FIG. 43*a* analyze various substantially contemporaneous engine data related to oil quality analysis via corresponding subroutines. Preferably, the control logic implements a top-down structure having a main program and several subroutines as illustrated. However, the control logic implemented in the subroutines could easily be incorporated within the main program as is well known in the art. The contemporaneous engine information may be used to provide specific messages to a vehicle operator corresponding to each individual analysis performed in steps 510 through 516. This information is also utilized in an overall synergistic analysis as indicated by step 526. At step 500, the value representing engine operating hours is examined to anticipate reasonable oil quality parameters. System parameters may be adjusted to accommodate various oil change schedules based on the number of engine hours. For example, a shorter oil drain interval may be indicated for new engines during a predetermined or adaptable break-in period. Likewise, the recommended oil drain interval may be shortened to accommodate component wear experienced in older engines. Step 502 then determines the number of engine hours since the last oil drain.

Step 504 of FIG. 43*a* performs a cycle analysis to determine the relative severity of the engine operating cycle. Preferably, after identifying aspects of the engine operation which could cause severe oil or engine degradation, a relative severity is assigned having a value between one and ten. The cycle severity may then be used to appropriately adjust the ROLE calculation. For example, excessive engine idling at extreme operating temperatures with a high sulfur fuel would indicate harsh operating conditions. The corresponding cycle severity rating may be assigned a value of five resulting in a 50% reduction in the ROLE calculation relative to the ROLE for a normal operating cycle.

With continuing reference to FIG. 43*a*, step 506 utilizes measured engine and oil sensor data obtained over an extended period to perform a trend analysis. The trend analysis utilizes appropriate statistics to detect trends in the engine operating cycle, engine oil quality measurements, and engine parameter data. In a preferred embodiment, the slope and standard deviation of each parameter curve is monitored over the last half of the oil drain interval to detect any trend indicating gradual oil degradation. In addition, the slope and standard deviation over the last 10% of the oil drain interval is examined to detect relatively sudden changes which may indicate sudden wear, contaminant infiltration, or that new oil has been added.

Step 508 determines a frequency to perform oil analysis calculations based on the above described indications of operating conditions. Oil analysis is performed more frequently when a severe cycle detected than for a normal operating cycle. As previously described, preferably, oil analysis performed shortly after engine start-up and shutdown. Oil analysis may also be triggered by the occurrence of various other engine conditions. If step 508 determines that oil analysis is not indicated at the present time, the method continues with step 524. If oil analysis is indicated, the method continues with step 510 which performs a viscosity analysis. The viscosity analysis measures viscosity and sets appropriate flags to indicate any problems which may be detected as explained in greater detail below. Viscosity analysis is based upon cycle trend analysis, viscosity trend analysis, and current engine operating parameters. A viscosity analysis subroutine is illustrated and described in detail with reference to FIGS. 44a and 44b.

As also shown in FIG. 43a, step 512 performs OilView Analysis. As disclosed in U.S. Pat. No. 5,262,732 referenced and incorporated by reference above, this analysis provides a number of useful oil quality indices including but not limited to a corrosion index, a contamination index, a ferromagnetic debris index, and a cumulative ferromagnetic debris parameter. Step 514 then determines the Total Base Number or TBN for the oil. The TBN values for the engine oil decrease due to acidic combustion products entering the oil. In general, the TBN value indicates corrosive potential of the oil but may not necessarily correlate with the corrosion index determined above. Thus, step 514 analyzes TBN values with respect to cycle severity, engine hours, TBN trends, and the like. An appropriate status flag may be set to indicate an unacceptable TBN value.

Step 516 of FIG. 43a analyzes both ferrous and nonferrous wear particles with respect to engine hours, oil hours, and historical trends. Typically, this analysis is made after engine shutdown using a relatively stagnant oil sample. The sensor frequency response is measured with and without an applied magnetic field. The measurements are then compared with a calibration file which provides ferrous and nonferrous particle concentrations. As previously described, an abnormal condition may initiate a specific recommendation to the operator or may simply be communicated to the synergistic analysis performed at step 526.

Step 518 of FIG. 43a attempts to determine the quantity and character of various types of contaminants such as water or glycol coolant and silicon particles. The sensor grid is very sensitive to water contamination since the dielectric properties of water and oil differ significantly. Sensor frequencies decrease as water concentrations increase. However, heavy-duty engine oils usually contain additives which disperse small quantities of water. This impacts the ability of the sensor grid to detect water when water concentration is low and affects detection characteristics with increasingly higher amounts of water. When water content becomes excessive, the additives within the oil are unable to function effectively and a thick emulsion may be formed. This phenomenon occurs more often in methanol and gasoline engines which operate in cold ambient conditions.

Water is a normal byproduct of combustion which escapes the combustion chamber and enters the crankcase with other combustion gases. The water then condenses within the oil sump as the engine and oil cool. Water can also enter the crankcase with engine coolant which is typically a 50:50 water-glycol mixture. Coolant contamination can occur when the oil is not drained and replaced after engine service (i.e. cylinder head removal) or when a coolant leak occurs. Although the latter is not a common failure mode, it can cause large quantities of coolant to enter the sump. Water adversely affects engine wear and depletes additives within the oil. Oil-borne water promotes ion mobility and subsequent corrosion of engine components. Resultant oxide layers then wear more quickly when the engine is started.

Large quantities of water can form thick emulsions when sufficiently mixed with oil. Emulsified oil/water mixtures restrict oil flow and are not conducive to proper lubrication. Emulsified oil/water mixtures can also cause changes in viscosity measurements.

Furthermore, many combustion byproducts form strong acids in the presence of water. However, because the boiling temperature of water at standard pressure is below normal engine operating temperatures, crankcase water is typically boiled off during normal operation. Thus, if water is detected after an extended operating period where the sump oil temperature exceeds 100° C., a severe coolant leak is indicated. Water evaporation effects are manifested as a progressively increasing sensor response frequency resulting from the decreasing dielectric constant. The sensor data analysis strategy uses this phenomena to detect water contamination.

With continuing reference to FIG. 43a, step 520 measures soot with respect to cycle severity and oil hours while performing a trend analysis. Similar to water contamination, soot contamination causes a significant decrease in the sensor response frequency. Since oil-borne soot concentrations are independent of temperature but depend on operating conditions, filtration, and oil changes, all temperature compensated frequency changes during an engine warm-up cycle may be attributed to water evaporation. Soot causes oil thickening (i.e. a higher viscosity) and tends to occur gradually during engine operation. In contrast, water does not impact viscosity unless the capacity of the additive dispersant is exceeded and an emulsion forms. Therefore, capacitance changes during warm-up combined with viscosity histories can confirm soot concentrations.

Step 522 determines the level of nitration and oxidation. Both oxidation and nitration reactions cause oil thickening and progressively decreasing sensor response frequencies. Step 524 reads the lubrication oil limits from non-volatile memory. These limits comprise a set of predetermined parameters which establish allowable lubrication oil degradation before initiating a response or warning. The limits are used as multipliers to adjust baseline calibration limits. The values of these parameters may be adjusted by a user to accommodate a particular application. During subsequent resale of the engine, a purchaser may access these values to gain insight into the probable severity of engine operation. For example, an aggressive calibration may extend ROLE calculations and associated limits by 25% where a conservative calibration may reduce ROLE calculations and associated oil quality limits by 25% from baseline or standard calibration values.

Step 526 of FIG. 43a performs a synergistic analysis utilizing information determined by various other analyses and current engine information. The synergistic analysis is illustrated and explained in detail with reference to FIG. 46. Step 528 of FIG. 43b determines whether the oil condition is acceptable based on the synergistic analysis of step 526. If oil quality is determined to be unacceptable, step 530 logs a warning fault in memory for future access by service or maintenance personnel. Step 532 alerts an operator of the warning fault by illuminating a light or providing an equivalent indication. If step 534 determines the oil condition is dangerous for continued operation of the engine, step 536 logs an appropriate emergency fault in the memory while step 538 alerts the operator via an emergency light or the like. Alternatively, or in addition thereto, the data hub driver interface may provide detailed explanations for operator warnings. Control then returns to step 542.

With continuing reference to FIG. 43b, if step 528 determines the oil condition is acceptable, any warning lights or emergency lights previously set are turned off at step 540. If an improvement in oil condition is not detected at step 542, then control passes to step 550 which returns to step 518 and the process begins again. Of course, other "main" programs may be executed concurrently or control may pass from step 550 to another program before returning to step 518. If step 542 determines that the oil condition is improving, step 544 determines whether an oil change has been performed.

If step 544 determines that the improvement in oil condition is not significant to indicate an oil change, then step 546 determines whether make-up oil has been added and responds appropriately, as explained in greater detail with reference to FIGS. 29 and 41, and control passes to step 550. Otherwise, an oil change is indicated and step 548 takes appropriate action, such as storing the current engine hours, alerting the vehicle operator, modifying measurement frequencies, or the like.

Figure 44A:
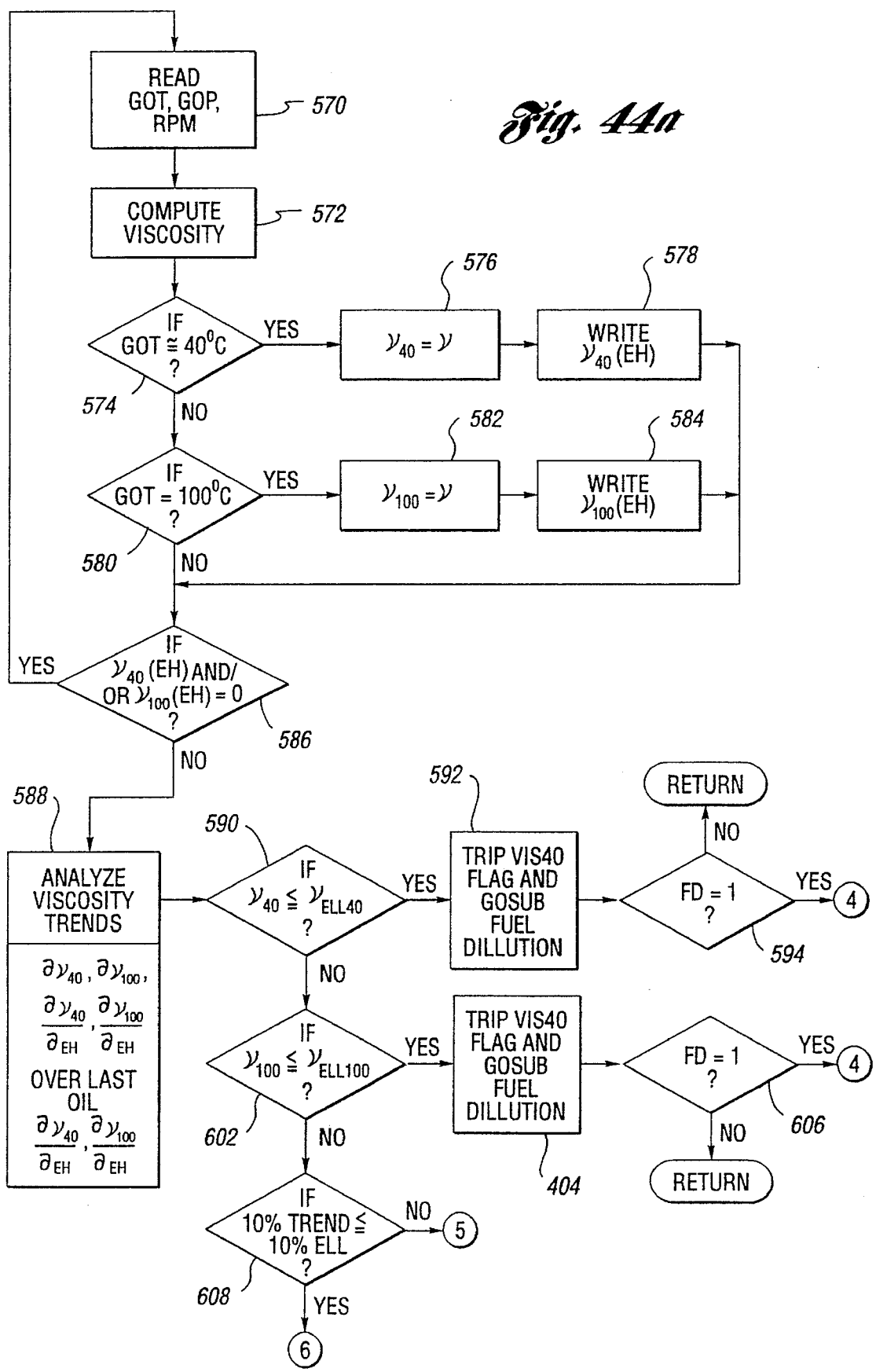
Figure 44B:
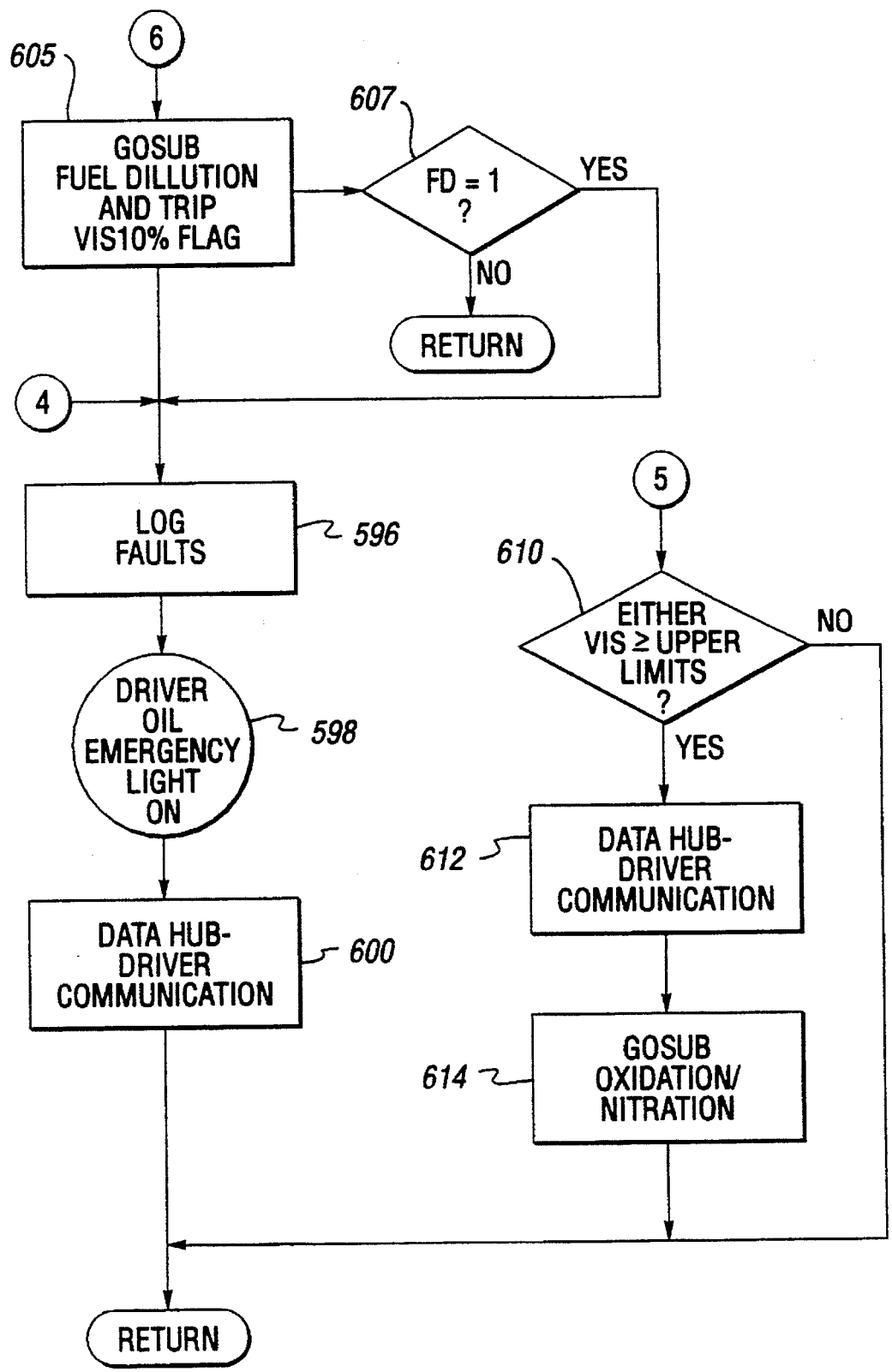

Referring now to FIGS. 44a and 44b, one method for analyzing engine oil viscosity according to the present invention is shown. Step 570 obtains the current oil temperature (GOT), oil pressure (GOP), and engine RPM from the appropriate sensors. In a preferred embodiment, step 572 determines the oil viscosity (v) as indicated by a viscosity sensor, such as that disclosed in U.S. Pat. No. 4,721,874 to Emmert. Of course, any of a number of other methods well known in the art can be used to provide a viscosity measurement or estimate. Step 574 determines if the oil temperature is approximately 40° C., or another predetermined temperature which has been selected for trend monitoring and analysis. Step 576 then sets the current viscosity, v, to a temporary variable, $v_{40}$ which is stored in non-volatile memory by step 578 as a function of elapsed engine hours. Steps 580, 582 and 584 operate in a similar fashion to monitor viscosity changes as a function of engine hours at a second predetermined temperature, such as 100° C.

Step 586 of FIG. 44a determines if both viscosity measurements had a value of zero indicating that the measurement was not currently available for either temperature, i.e. the engine has not reached its nominal operating temperature. Control then returns to step 570 and the loop is repeated until both measurements have been obtained. Step 588 applies a conventional statistical analysis to the viscosity measurements to identify trends in viscosity changes for both predetermined temperatures (40° C. and 100° C. in a preferred embodiment). The standard deviations ($\sigma_v$) and first derivatives with respect to engine hours are calculated using measurements obtained since the previous oil drain, and over the most recent 10% and 50% of the current oil drain interval. Of course, other intervals are also feasible depending upon the particular application.

Steps 590, 602, and 608 determine appropriate subsequent action based on the value of the current viscosity measurement or the viscosity trend. If step 590 determines that the viscosity measurement obtained at 40° C. is lower than a corresponding predetermined emergency lower limit, then step 592 sets a flag and determines if fuel dilution is present. A method for determining fuel dilution is illustrated and described in detail with reference to FIG. 45. If fuel dilution is indicated, an appropriate flag (FD) is set and control is directed by step 594 to step 596 (FIG. 44b). Otherwise, control returns to the main program.

As shown in FIG. 44b, step 596 logs a viscosity fault within the non-volatile memory for future access by maintenance or service personnel. Step 598 alerts the operator to an oil emergency by illuminating a light or other such appropriate means. Step 600 then communicates the information to the data hub, the ECM and/or a driver interface before returning control to the main program. In a similar fashion, step 602 determines whether the viscosity measurement at 100° C. is below a corresponding predetermined limit. If so, control passes to steps 604, 606, 596, 598, and 600 similar to the manner previously described. Also analogously, steps 604, 606, 596, 598, and 600 take appropriate action if step 608 determines the viscosity trend over the most recent 10% of the oil change interval is below a predetermined limit. However, if step 608 determines that the recent trend is not below the predetermined limit, step 610 determines whether either of the viscosity measurements exceeds a corresponding upper limit. When either upper limit is exceeded (indicating a "thickening" of the oil), step 612 sets an appropriate flag in memory and performs a soot analysis as previously described. Step 614 then determines the oxidation and/or nitration levels of the oil before control is returned to the main program.

Figure 45:
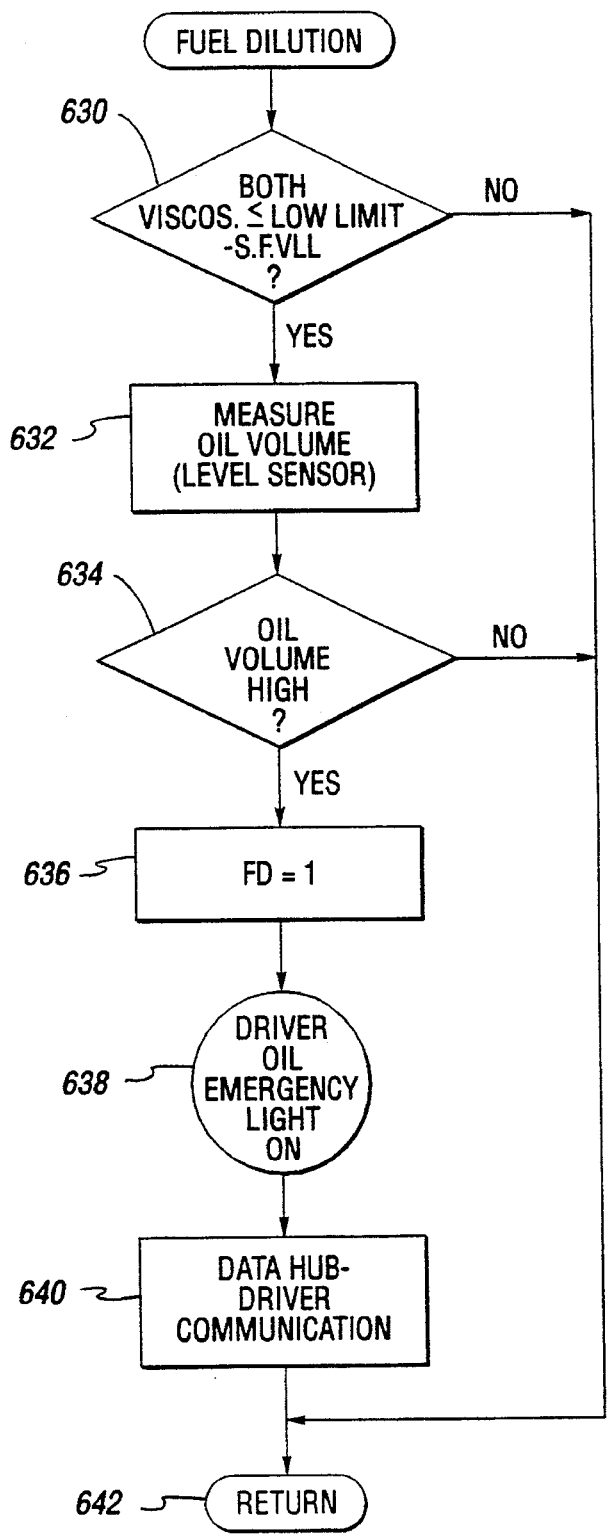

Referring now to FIG. 45, a process for detecting fuel dilution according to the present invention is shown. Step 630 determines whether both viscosity measurements ($v_{40}$ and $v_{100}$) are below corresponding low limits as reduced by corresponding safety margins. If the result of step 630 is negative, fuel dilution is not indicated and control returns to the calling program via step 642. Otherwise, the current oil volume is detected by step 632 via a signal produced by an oil level sensor. If fuel has infiltrated the oil sump, step 634 will detect an excessively high oil volume and step 636 will set the appropriate flag to indicate fuel dilution. Otherwise, step 634 returns control to the calling program via step 642. Step 638 alerts the operator to an oil emergency by energizing a light, or other suitable indicator. Step 640 communicates an appropriate message to the operator via an optional data hub display before returning control to the calling program via step 642.

Figure 46:
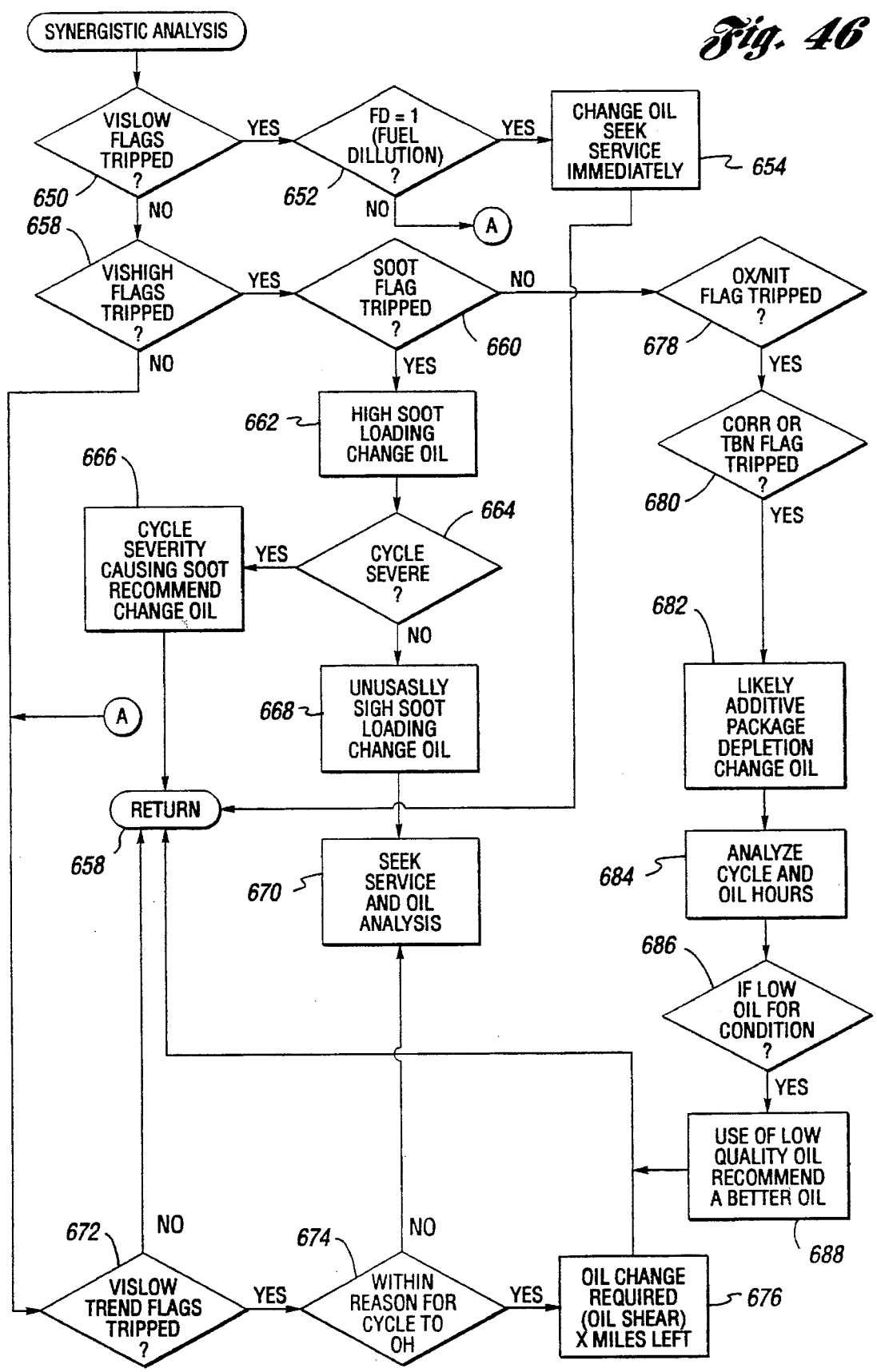

Referring now to FIG. 46, a method for synergistic oil quality analysis according to the present invention is illustrated. Step 650 determines whether any flags have been set indicating a low viscosity. A positive result at step 650 results in a test for the fuel dilution flag at step 652. If the fuel dilution flag has not been set, control passes to step 672. If fuel dilution is indicated, the synergistic analysis indicates that the user should change the oil and seek service immediately. Control then returns to the calling program via step 656. The various indicated messages, for example those indicated by steps 654, 666, and 688, during synergistic analysis may be conveyed to the user in any of a number of conventional fashions. In a preferred embodiment, appropriate messages are presented to the user or operator on the optional data hub display. Error or fault codes corresponding to a detected fault, warning, or other condition of interest may also be stored or communicated to the user or other vehicle systems and subsystems. Various results from program subroutines can be used to confirm other conclusions.

Step 658 of FIG. 46 examines status flags to determine if a high viscosity is indicated. A positive result at step 658 leads to step 660 where a status flag is examined to determine whether a high soot concentration has been detected. If so, step 662 generates an appropriate recommendation to change the oil. If step 664 detects severe duty cycle, step 666 generates a message recommending better oil before returning to the calling program via step 656. If a severe duty cycle is not detected, step 668 and 670 generate a message alerting the user to the unusually high soot loading for the duty cycle and recommending a more extensive oil analysis.

With continuing reference to FIG. 46, if neither low nor high viscosity flags are set as determined by steps 650 and 658, respectively, step 672 inspects the viscosity trend status flag. If the viscosity trend flag is clear, control returns to the calling program via step 656. Otherwise, step 674 determines whether the viscosity reading is within a marginal range based on the current duty cycle and engine hours. If not, step 670 recommends a more comprehensive oil analysis and service assistance. If the viscosity measurement is within reason (but following an unacceptable trend as determined by step 672), then step 676 recommends an oil change in the near future by modifying the remaining miles calculated by the ROLE as a result of the oil shear.

If the soot flag has not been set as determined by step 660, step 678 examines a flag to determine whether high levels of oxidation or nitration are present. Step 680 then examines the corrosion and TBN flags. If the result of steps 678 and 680 are positive, oil additive package depletion is indicated and an oil change is recommended at step 682. Otherwise control returns via step 656 to the calling program. Step 684 then performs a cycle analysis using the number of oil hours to determine the relative quality of the oil. If the oil hours are relatively low based on the recent operating conditions as determined by step 686, an appropriate message is conveyed to the operator at step 688. Otherwise, control returns to the calling program via step 656 without generating a message since the oil life is reasonable for current conditions.

Figures 47, 48:
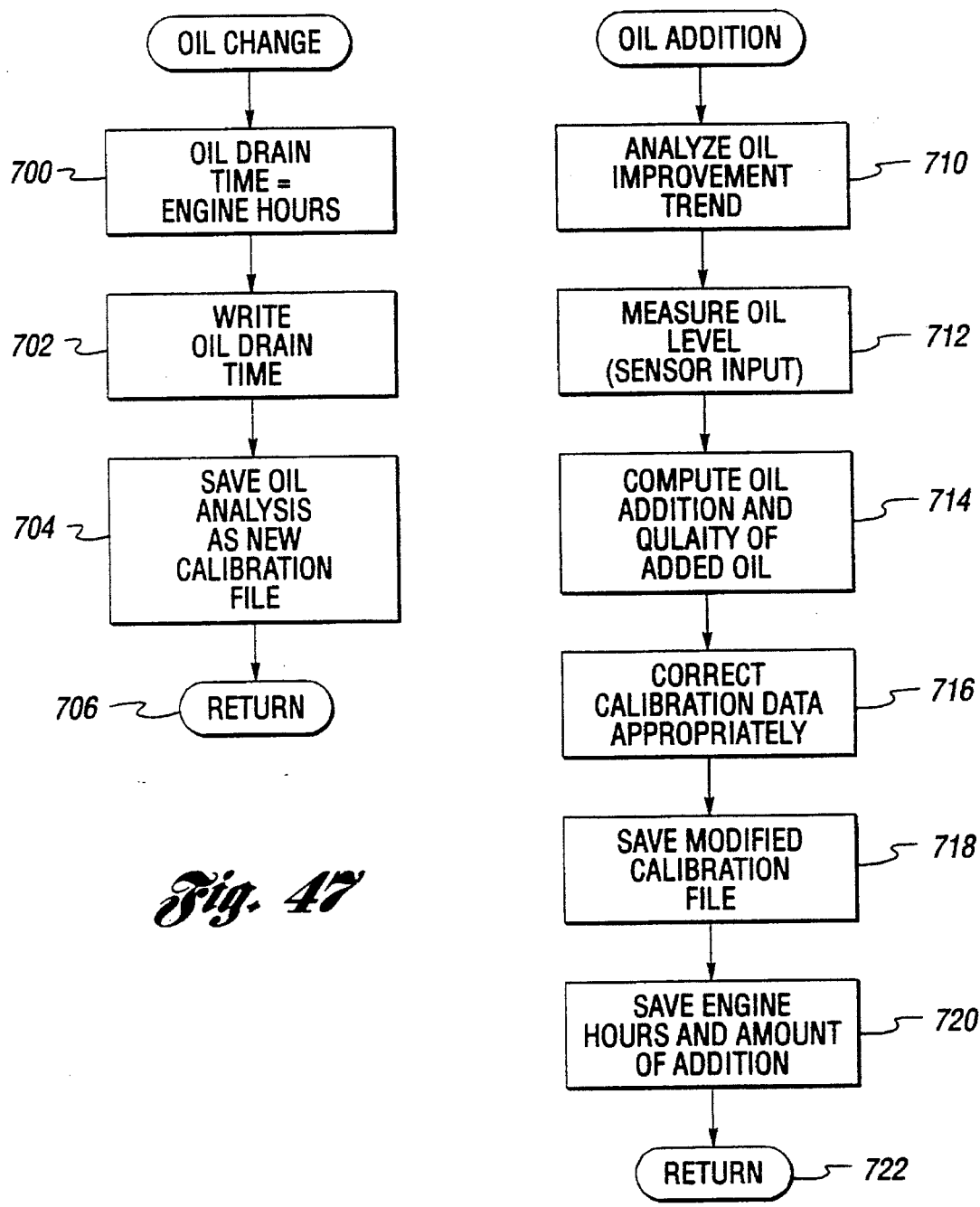

FIG. 47 illustrates the steps involved in recording information after an oil drain has been either explicitly indicated or automatically detected by the system. Step 700 sets the value for the oil drain to the current elapsed engine running hours. Step 702 stores the oil drain time within non-volatile memory. Step 704 archives the oil analysis statistics within non-volatile memory for use in future historical analysis. This information can also be accessed by service personnel via the engine control logic or the data hub.

FIG. 48 illustrates the steps for detecting and accommodating make-up oil addition according to the present invention. Step 710 analyzes the trend in various oil quality statistics, i.e. the change in quality measurements and standard deviations, to determine whether these measurements have improved during recent engine operation. Step 712 obtains a current oil level measurement for the sump oil from an appropriate sensor. Step 714 computes the amount of oil added based on the change in measurements obtained from the oil lever sensor, and the quality of the added oil based on the change in oil quality measurements. Step 716 then corrects the baseline calibration curve based on the amount and quality of the oil added to the sump. The modified calibration curve is saved at step 718 and step 720 saves the current elapsed engine operating hours and the amount of the oil addition on non-volatile memory. Step 722 then returns control to the calling program Although a preferred embodiment has been described, it will be understood that the invention is capable of numerous modifications, rearrangements and substitutions of parts. For example, particular oil-borne contaminants have substantially unique, frequency-dependent dielectric properties that may be identified by incremental or sweep variations in the sensor 20 input signal frequency. Useful data may also be acquired by measuring the phase shift of a sensor 20 signal in the microwave frequency range. It will also be understood that the words used are descriptive rather than limiting, and that the various changes may be made without departing from the spirit and scope of the invention as claimed below.

What is claimed is:

1. An apparatus for monitoring the condition of and detecting at least one physical property of contaminants in flowing lubricating oil, the apparatus comprising:

a sensor having at least two electrically conductive elements exposed to said oil, said oil separating said conductive elements as an insulating dielectric medium therebetween to form a capacitor;

monitor means for monitoring the capacitance of said sensor during discrete testing intervals and determining the condition of and at least one physical property of contaminants in said oil based upon the change in sensor capacitance over said discrete testing intervals;

at least two electromagnet windings positioned proximately to said sensor for inducing a magnetic field about said sensor, the magnetic field affecting the migration of magnetically responsive contaminants of said oil into said sensor; and switching means for manipulating electric power of said electromagnet windings so as to remove substantially all magnetic flux from proximity of the sensor and release accumulated debris into the flowing lubricating oil between said discrete testing intervals.

2. An apparatus as described by claim 1 wherein said electromagnet windings are radially concentric.

3. An apparatus as described by claim 2 wherein said radially concentric windings are separated by cylindrical core structure.

4. An apparatus for monitoring the condition of flowing lubrication oil, the apparatus comprising:

enclosure means for confining a volume of test subject lubricating oil;

conduit means for supplying said enclosure means with a flow stream of lubricating oil;

a sensor having at least two electrically conductive elements exposed to said oil at a boundary area respective to said enclosure means, said oil separating said conductive elements as an insulating dielectric medium therebetween to form a capacitor, said sensor being located within said enclosure means at a position for selective flushing of accumulated contaminants from said conductive elements by said oil flow stream; and monitor means for monitoring the capacitance of said sensor at discrete intervals so as to determine the condition of the subject lubricating oil based upon the change in sensor capacitance over said discrete time intervals.

5. An apparatus as described by claim 4 further comprising at least two electromagnet windings positioned proximately to said sensor for inducing a magnetic field within said enclosure means and through said sensor for affecting the migration of magnetically responsive contaminants relative to said sensor.

6. An apparatus as described by claim 4 wherein said discrete intervals of monitoring include an interval between capacitance measurements before and after flushing of accumulated contaminants.

7. An apparatus as described by claim 4 wherein said discrete intervals of monitoring are delineated between recurring moments within an operating duty cycle.

8. An apparatus as described by claim 7 wherein said radially concentric windings are separated by cylindrical core structure.

9. An apparatus as described by claim 4 wherein said conduit means is connected in a lubrication oil circulation circuit.

10. An apparatus as described by claim 4 wherein said sensor is located within said enclosure means to be continuously flushed of accumulated contaminants by oil circulation.

11. An apparatus as described by claim 4 wherein said conduit means includes valve means for controlling a flow rate of the oil flow steam.

12. An apparatus as described by claim 11 further comprising control logic in communication with said valve means for controlling the flow rate.

13. An internal combustion engine having an engine oil circulation system, an electronic engine controller, and an engine oil analyzing system in communication with the engine controller, the engine oil analyzing system comprising:
- a housing attached to the engine and having a measurement chamber in fluid communication with the engine oil circulation system;
- a capacitive sensor disposed within said housing, said sensor characterized by at least two conductive elements having a space therebetween for accommodating engine oil which functions as a dielectric;
- control logic including memory in communication with said sensor for providing power to said sensor, measuring frequency response of said sensor, and analyzing changes in the frequency response of said sensor over time; and
- an electromagnet proximate said sensor for selectively creating a magnetic field within the measurement chamber, said electromagnet being controlled by said control logic.

14. The invention of claim 13 wherein said housing includes an internal engine oil flow path in open communication with the engine oil circulation system so as to allow at least a portion of the engine oil circulating within said engine to be circulated through said housing; and
- wherein the internal engine oil flow path intersects a measurement chamber characterized by substantially stagnant oil flow relative to the engine oil flow path, the measurement chamber including a lower base portion open to the exterior of said sensor housing for receiving said capacitive sensor.

15. The invention of claim 13 wherein the measurement chamber is in the form of a cylinder and wherein said sensor is disposed coaxially with the measurement chamber.

16. The invention of claim 13 wherein the measurement chamber is cylindraceous and wherein said sensor is concentrically interposed between the measurement chamber and said electromagnet.

17. The invention of claim 13 wherein the oil flow path includes an entrance portion leading to an inlet port of the measurement chamber and an exit portion leading from an exit port of the measurement chamber, said oil flow path entrance portion being geometrically characterized as a NASA bend.

18. The invention of claim 13 wherein the oil flow path includes an entrance portion leading to an inlet port of said measurement chamber and an exit portion leading from an exit port of the measurement chamber and wherein both of said entrance and exit portions are geometrically characterized as NASA bends so as to provide substantially laminar engine oil flow through said entrance and exit portions and across said sensor.

19. The invention of claim 13 wherein said housing includes a cylindrical hub portion, a neck portion radially offset from said hub portion, and an enclosure portion connected to said neck portion and defining said measurement chamber;
- said hub portion being cylindraceous and having an axis parallel to the axis of said measurement chamber and being attached to the engine intermediate an engine oil filter such that engine oil is continuously circulated through said hub portion to and from the engine oil filter.

20. The invention of claim 19 wherein said hub includes a plurality of helical vanes for facilitating increased oil flow across said sensor so as to promote displacement of accumulations away from said sensor.

21. The invention of claim 19 wherein said neck portion includes an oil flow path generally vertically disposed and in open communication with an inlet port of the measurement chamber at one end and with an exit port of the measurement chamber at its other end, and including therebetween a venturi section to provide a pressure drop within the exit oil flow path so as to induce oil flow across said sensor.

22. The invention of claim 13 wherein the oil flow path includes an entrance portion leading to an inlet port of said measurement chamber and an exit portion leading from an exit port of the measurement chamber, said exit portion having a venturi in open communication with the exit portion for creating a pressure drop across the measurement chamber and inducing oil flow across said sensor.

23. The invention of claim 13 wherein said sensor includes four quadrants and wherein the measurement chamber includes an oil inlet port adjacent a first quadrant and an oil exit port adjacent a fourth quadrant, the oil inlet and exit ports being substantially parallel to one another such that oil entering the measurement chamber traverses said sensor in a substantially circular motion so as to displace accumulations from said sensor.

24. The invention of claim 13 wherein said sensor includes first and second sensor grids, said first sensor grid being exposed to said measurement chamber, said second sensor grid being enclosed within a second enclosure member separated from the measurement chamber by a flexible diaphragm so as to accommodate a reference substance.

25. The invention of claim 24 wherein said sensor comprises a plurality of sensor grids including first and second sensor grids disposed at opposite ends of the measurement chamber, the measurement chamber being located downstream from an engine oil filter, the plurality also including a third sensor grid enclosed within a second enclosure member located upstream from the engine oil filter so as to facilitate comparison of measurements before and after filtering.

26. The invention of claim 13 further comprising:
- a channel for adding oil to the engine oil circulation system, said channel including a collection elbow portion so as to facilitate collection of a sample of added engine oil;
- a sample measurement chamber in fluid communication with the collection elbow portion; and
- a second capacitive sensor exposed to said sample measurement chamber so as to facilitate real-time analysis of added engine oil.

27. The invention as described in claim 13 further comprising a viscosity sensor in communication with the control logic for determining viscosity of the engine oil.

28. The invention as described in claim 13 wherein said sensor includes temperature sensing circuitry for providing a signal to the engine controller indicative of oil temperature surrounding said sensor.

29. An engine oil analyzing system for use with an internal combustion engine having an electronic engine controller, the engine including an engine oil circulation system having a port adapted to receive an engine oil filter, the engine oil analyzing system comprising:
- a generally cylindrical housing adapted to engage the port and establish fluid communication with the engine oil circulation system;
- a perforated annular sleeve disposed within said housing and concentric thereto;

an annular filter element disposed about said annular sleeve within said housing;

a generally annular baffle member disposed concentrically about said filter element within said housing so as to divert engine oil radially outward into an annular measurement chamber; and at least one capacitive sensor exposed to at least a portion of the annular measurement chamber, each of the at least one sensor including at least two conductive elements having a space therebetween for accommodating engine oil which functions as a dielectric.

30. The invention as described in claim 29 further comprising:

at least one electromagnet proximate at least one of said at least one capacitive sensor for selectively creating a magnetic field within the measurement chamber, said at least one electromagnet being controlled by said electronic engine controller.

31. The invention of claim 30 further comprising:

at least one permanent magnet proximate at least one of said at least one capacitive sensor for creating a magnetic field within the measurement chamber.

32. An internal combustion engine having an engine oil circulation system, an electronic engine controller, and an engine oil analyzing system in communication with the engine controller, the engine oil analyzing system comprising:

a housing attached to the engine and having a measurement chamber in fluid communication with the engine oil circulation system;

a capacitive sensor disposed within said housing, said sensor characterized by at least two conductive elements having a space therebetween for accommodating engine oil which functions as a dielectric; and control logic including memory in communication with said sensor for providing power to said sensor, measuring frequency response of said sensor, and analyzing changes in the frequency response of said sensor over time.

* * * * *

UNITED STATES PATENT AND TRADEMARK OFFICE
CERTIFICATE OF CORRECTION

PATENT NO. : 5,604,441
DATED : February 18, 1997
INVENTOR(S) : Charles E. Freese, v, et. al.

It is certified that error appears in the above-indentified patent and that said Letters Patent is hereby corrected as shown below:

| | |
|---|---|
| Column 10, Line 33, | Delete "analized" and insert "analyzed". |
| Column 12, Line 53, | Delete "Wear" and insert "wear". |
| Column 26, Line 65, | After "cycle" insert -- "is"--. |
| Column 26, Line 67, | After "analysis" insert -- "is"-- |
| Column 31, Line 32, | After "via" insert "a service tool which interfaces with the system via". |
| Column 31, Line 48, | Delete "on" and insert "in". |

Signed and Sealed this

Twenty-fifth Day of August, 1998

Attest:

BRUCE LEHMAN

*Attesting Officer*   *Commissioner of Patents and Trademarks*